United States Patent
Inberg et al.

(10) Patent No.: US 10,907,152 B2
(45) Date of Patent: Feb. 2, 2021

(54) COMPOSITIONS AND METHODS FOR CONTROLLING ARTHROPOD PARASITE AND PEST INFESTATIONS

(71) Applicants: MONSANTO TECHNOLOGY LLC, St. Louis, MO (US); BEEOLOGICS, INC., St. Louis, MO (US)

(72) Inventors: Alex Inberg, Ballwin, MO (US); Mahak Kapoor, Chesterfield, MO (US)

(73) Assignee: MONSANTO TECHNOLOGY LLC, St. Louis, MO (US)

(*) Notice: Subject to any disclaimer, the term of this patent is extended or adjusted under 35 U.S.C. 154(b) by 154 days.

(21) Appl. No.: 15/571,697

(22) PCT Filed: May 3, 2016

(86) PCT No.: PCT/US2016/030579
§ 371 (c)(1),
(2) Date: Nov. 3, 2017

(87) PCT Pub. No.: WO2016/179180
PCT Pub. Date: Nov. 10, 2016

(65) Prior Publication Data
US 2019/0203206 A1     Jul. 4, 2019

Related U.S. Application Data

(60) Provisional application No. 62/156,751, filed on May 4, 2015.

(51) Int. Cl.
| | | |
|---|---|---|
| *C12N 15/113* | (2010.01) | |
| *A01N 57/16* | (2006.01) | |
| *A01K 51/00* | (2006.01) | |

(52) U.S. Cl.
CPC ............ *C12N 15/113* (2013.01); *A01K 51/00* (2013.01); *A01N 57/16* (2013.01); *C12N 2310/14* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,469,863 A | 9/1984 | Ts'o et al. |
| 4,476,301 A | 10/1984 | Imbach et al. |
| 5,023,243 A | 6/1991 | Tullis |
| 5,034,506 A | 7/1991 | Summerton et al. |
| 5,166,315 A | 11/1992 | Summerton et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,214,134 A | 5/1993 | Weis et al. |
| 5,216,141 A | 6/1993 | Benner |
| 5,235,033 A | 8/1993 | Summerton et al. |
| 5,264,423 A | 11/1993 | Cohen et al. |
| 5,264,562 A | 11/1993 | Matteucci |
| 5,264,564 A | 11/1993 | Matteucci |
| 5,276,019 A | 1/1994 | Cohen et al. |
| 5,278,302 A | 1/1994 | Caruthers et al. |
| 5,286,717 A | 2/1994 | Cohen et al. |
| 5,321,131 A | 6/1994 | Agrawal et al. |
| 5,399,676 A | 3/1995 | Froehler |
| 5,405,938 A | 4/1995 | Summerton et al. |
| 5,405,939 A | 4/1995 | Suhadolnik et al. |
| 5,453,496 A | 9/1995 | Caruthers et al. |
| 5,455,233 A | 10/1995 | Spielvogel et al. |
| 5,466,677 A | 11/1995 | Baxter et al. |
| 5,470,967 A | 11/1995 | Huie et al. |
| 5,476,925 A | 12/1995 | Letsinger et al. |
| 5,489,677 A | 2/1996 | Sanghvi et al. |
| 5,519,126 A | 5/1996 | Hecht |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,561,225 A | 10/1996 | Maddry et al. |
| 5,563,253 A | 10/1996 | Agrawal et al. |
| 5,571,799 A | 11/1996 | Tkachuk et al. |
| 5,587,361 A | 12/1996 | Cook et al. |
| 5,593,874 A | 1/1997 | Brown et al. |
| 5,596,086 A | 1/1997 | Matteucci et al. |
| 5,602,240 A | 2/1997 | De Mesmaeker et al. |

(Continued)

FOREIGN PATENT DOCUMENTS

| | | |
|---|---|---|
| EP | 0 375 408 A1 | 6/1990 |
| EP | 3 066 200 A1 | 9/2016 |
| WO | WO 2015/001336 A2 | 1/2015 |

OTHER PUBLICATIONS

Aoki et al., "In Vivo Transfer Efficiency of Antisense Oligonucleotides into the Myocardium Using HVJ—Liposome Method," Biochem Biophys Res Commun, 231:540-545 (1997).
Beal et al., "Second Structural Motif for Recognition of DNA by Oligonucleotide-Directed Triple-Helix Formation," Science, 251:1360-1363 (1992).
Bhargava et al., "Long double-stranded RNA-mediated RNA interference as a tool to achieve site-specific silencing of hypothalamic neuropeptides," Brain Research Protocols, 13:115-125 (2004).
Breaker et al., "A DNA enzyme with Mg2+-dependent RNA phosphoesterase activity," Chemistry and Biology, 2:655-660 (1995).

(Continued)

*Primary Examiner* — Tracy Vivlemore
(74) *Attorney, Agent, or Firm* — Arnold & Porter Kaye Scholer LLP; Amanda Carmany-Rampey; David R. Marsh

(57) ABSTRACT

This application provides and discloses anti-parasitic, anti-pest or insecticidal nucleic acid molecules and their calmodulin target genes for the control of arthropod parasites and pests. In particular, this application provides and discloses insecticidal nucleic acid molecules that target *Varroa* calmodulin gene sequences. This application further provides methods and compositions for the control and treatment of parasites and pests in *Apis mellifera* (honey bee) hives.

18 Claims, 11 Drawing Sheets
Specification includes a Sequence Listing.

(56) References Cited

U.S. PATENT DOCUMENTS

| | | | |
|---|---|---|---|
| 5,608,046 | A | 3/1997 | Cook et al. |
| 5,610,289 | A | 3/1997 | Cook et al. |
| 5,618,704 | A | 4/1997 | Sanghvi et al. |
| 5,623,070 | A | 4/1997 | Cook et al. |
| 5,625,050 | A | 4/1997 | Beaton et al. |
| 5,633,360 | A | 5/1997 | Bischofberger et al. |
| 5,663,312 | A | 9/1997 | Chaturvedula |
| 5,677,437 | A | 10/1997 | Teng et al. |
| 5,677,439 | A | 10/1997 | Weis et al. |
| 5,714,331 | A | 2/1998 | Buchardt et al. |
| 5,719,262 | A | 2/1998 | Buchardt et al. |
| 5,721,138 | A | 2/1998 | Lawn |
| 6,303,374 | B1 | 10/2001 | Zhang et al. |
| 6,348,185 | B1 | 2/2002 | Piwnica-Worms |
| 2002/0123476 | A1 | 9/2002 | Emanuele et al. |
| 2003/0017068 | A1 | 1/2003 | Larrain et al. |
| 2003/0096980 | A1 | 5/2003 | Froehler et al. |
| 2012/0128218 | A1 | 5/2012 | Amyot et al. |
| 2012/0258646 | A1 | 10/2012 | Sela et al. |
| 2012/0316220 | A1 | 12/2012 | Ward et al. |

OTHER PUBLICATIONS

Database Accession No. BT006855, "*Homo sapiens* calmodulin 3 (phosphorylase kinase, delta) mRNA" pp. 1-2 (2003).
Diallo et al., "Long Endogenous dsRNAs Can Induce Complete Gene Silencing in Mammalian Cells and Primary Cultures," Oligonucleotides, 13:381-392 (2003).
Extended European Search Report dated Jan. 14, 2019, in European Patent Application No. 16789940.0.
Foley et al., "The distribution of *Aspergillus* spp. Opportunistic parasites in hives and their pathogenicity to honey bees," Veterinary Microbiology, 169:203-210 (2014).
Garbian et al., "Bidirectional Transfer of RNAi between Honey Bee and Varroa destructor: Varroa Gene Silencing Reduces Varroa Population," 8(12):1-9:e1003035 (2012).
GenBank Accession No. EW913311.1, G894P5149RL18.T0 Ixodes scapularis Pooled Non-infected Normalized Library Ixodes scapularis cDNA, mRNA sequence, p. 1 (2007).
GenBank Accession No. GD053132.1, KS13012F07 KS13 Capsicum annuum cDNA, mRNA sequence, pp. 1-2 (2009).
Heath et al., "RNA Interference Technology to Control Pest Sea Lampreys—A Proof-of-Concept," PLOS One, 9(2):e88387:1-9 (2014).
Heneberg et al., "Assemblage of filamentous fungi associated with aculeate hymenopteran brood in reed galls," Journal of Invertebrate Pathology, 133:95-106 (2016).
International Search Report and Written Opinion dated Oct. 17, 2016, in International Application No. PCT/US2016/030579.
Kronenwett et al., "Oligodeoxyribonucleotide Uptake in Primary Human Hematopoietic Cells is Enhanced by Cationic Lipids and Depends on the Hematopoietic Cells Subset," Blood, 91(3):852-862 (1998).
Luft, "Making sense out of antisense oligodeoxynucleotide delivery: getting there is half the fun," J Mol Med, 76:75-76 (1998).
Matveeva et al., "Prediction of antisense oligonucleotide efficacy by in vitro methods," Nature Biotechnology, 16:1374-1375 (1998).
Moser et al., "Sequence-Specific Cleavage of Double Helical DNA by Triple Helix Formation," Science, 238:645-646 (1987).
Paddison et al., "Stable suppression of gene expression by RNAi in mammalian cells," Proc. Natl Acad. Sci. USA, 99(3):1443-1448 (2002).
Rajur et al., "Covalent Protein—Oligonucleotide Conjugates for Efficient Delivery of Antisense Molecules," Bioconjug Chem., 8:935-940 (1997).
Reither et al., "Specificity of DNA triple helix formation analyzed by a FRET assay," BMC Biochemistry, 3:27 (2002).
Santoro et al., "A general purpose RNA-cleaving DNA enzyme," Proc. Natl. Acad. Sci. USA, 94:4262-4266 (1997).
Seidman et al., "The potential for gene repair via triple helix formation," J Clin Invest., 112(4):487-494 (2003).
Standifer et al.,"Supplemental Feeding of Honey Bee Colonies," Agriculture Information Bullentin No. 413, USDA, pp. 1-8 (1977).
Strat et al., "Specific and nontoxic silencing in mammalian cells with expressed long dsRNAs," Nucleic Acids Research, 34(13):3803-3810 (2006).
Tran et al., "Control of specific gene expression in mammalian cells by co-expression of long complementary RNAs," FEBS Lett.;573(1-3):127-134 (2004).
Walton et al., "Thermodynamic and Kinetic Characterization of Antisense Oligodeoxynucleotide Binding to a Structured mRNA," Biophysical Journal, 82:366-377 (2002).

COMPOSITIONS AND METHODS FOR CONTROLLING ARTHROPOD PARASITE AND PEST INFESTATIONS

CROSS-REFERENCE TO RELATED APPLICATIONS AND INCORPORATION OF SEQUENCE LISTING

This application is a U.S. National Stage Application of International Application No. PCT/US2016/030579, filed May 3, 2016, which claims priority to U.S. Provisional Application No. 62/156,751, filed May 4, 2015, both of which are incorporated by reference in their entireties herein. A sequence listing contained in the file named P34304US01_SEQ.txt which is 67,313 bytes (measured in MS-Windows®) and created on Nov. 3, 2017, comprises 94 nucleotide sequences, is filed electronically herewith and incorporated by reference in its entirety.

FIELD OF THE DISCLOSURE

Methods and compositions for controlling parasite and pest infestations of arthropods are provided. Also provided are methods and compositions for controlling *Varroa* mite infestation in bees.

BACKGROUND

Arthropods of various species are increasingly cultured on a commercial scale. Insects and their grubs are nutritious and are eaten both raw and cooked in many cultures. Crustaceans such as crabs, lobsters, crayfish, shrimp and prawns are farmed on a large commercial scale and are an important part of the human diet. In addition to the culture of arthropod species for food, arthropods are also cultured as part of pest management strategies, including for the biological control of other arthropods, for example the culture parasitic wasps for the control of roaches and fire ants. Arthropods may also serve as the source of raw materials such as dyes, drugs, medicines, and antibiotics. Growing with the increasing importance of arthropod culture, are various pests and parasites that destroy the arthropod colonies or greatly reduce the yields of products obtained from arthropod culture. Accordingly, there is an increasing need for methods to control arthropod pests and parasites.

Among the most important species of cultured arthropods is the honey bee. Honey bees, *Apis mellifera*, are required for the effective pollination of crops and are therefore critical to world agriculture. Honey bees also produce economically important products, including honey and bees wax. Honey bees are susceptible to a number of parasites and pathogens, including the ectoparasitic mite, *Varroa destructor*.

*Varroa* (*Varroa destructor*) mites are the number one parasite of managed honey bees (*Apis mellifera*) and the biggest global threat to commercial beekeeping (Rosenkranz et al. 2010). An adult mite typically enters the worker and drone brood cells before they are capped, primed by honeybee brood pheromone. The mite submerges into the brood food that the bees put inside the cell in anticipation of capping, most probably to avoid being recognized and removed by nurse bees. Following capping of the brood cells by the nurse bees, the mite adheres to the larva and starts to ingest bee larval hemolymph. This process primes oogenesis in the mites, and is followed several days later in laying of male and female eggs. Eventually, the adult *Varroa* exit the cell and cling onto the emerging bees. *Varroa* directly damages the honeybees in multiple ways, most notably by draining resources, adversely affecting the innate honey bee immune system, and by being a very effective vector of viruses (Di Prisco et al. 2011), some of which are known to replicate in the mite, thus dramatically increasing the viral load.

A safe, efficacious and long-lasting solution to the *Varroa* problem is an ongoing challenge that has yet to be met. Currently, beekeepers use a plethora of methods to control *Varroa* levels that include various chemical miticides, most of which have lost efficacy and are toxic and/or leave residues in wax and honey. Other methods include application of oxalic or formic acid, monoterpenes (thymol) and a variety of other management practices, with highly variable outcomes, including toxicity to the treated colonies. Breeding of bees for resistance to *Varroa*, such as selection for Hygienic behavior which results in the removal of infested brood, has provided a limited practical success.

Colony Collapse Disorder (CCD) of honeybees is threatening to annihilate U.S. and world agriculture. Indeed, in the recent outbreak of CCD in the U. S in the winter of 2006-2007, an estimated 25% or more of the 2.4 million honeybee hives were lost because of CCD. An estimated 23% of beekeeping operations in the United States suffered from CCD over the winter of 2006-2007, affecting an average of 45% of the beekeepers operations. In the winter of 2007-2008, the CCD action group of the USDA-ARS estimated that a total of 36% of all hives from commercial operations were destroyed by CCD.

CCD is characterized by the rapid loss from a colony of its adult bee population, with dead adult bees usually found at a distance from the colony. At the final stages of collapse, a queen is attended only by a few newly emerged adult bees. Collapsed colonies often have considerable capped brood and food reserves. The phenomenon of CCD was first reported in 2006; however, beekeepers noted unique colony declines consistent with CCD as early as 2004. Various factors such as mites and infectious agents, weather patterns, electromagnetic (cellular antennas) radiation, pesticides, poor nutrition and stress have been postulated as causes. To date, control of CCD has focused on *Varroa* mite control, sanitation and removal of affected hives, treating for opportunistic infections (such as *Nosema*) and improved nutrition. No effective preventative measures have been developed to date.

*Varroa* mites parasitize pupae and adult bees and reproduce in the pupal brood cells. The mites use their mouths to puncture the exoskeleton and feed on the bee's hemolymph. These wound sites in the exoskeleton harbor bacterial infections, such as Melissococcus pluton, which causes European foulbrood. In addition, to their parasitic effects, *Varroa* mites are suspected of acting as vectors for a number of honey bee pathogens, including deformed wing virus (DWV), Kashmir bee virus (KBV), acute bee paralysis virus (ABPV) and black queen cell virus (BQCV), and may weaken the immune systems of their hosts, leaving them vulnerable to infections. If left untreated *Varroa* infestations typically result in colony-level mortality.

Current methods of treating *Varroa* infestations are proving to be ineffective as the mites develop resistance to existing miticides. In addition, the use of such miticides may introduce injurious chemicals into honey that is intended for human consumption.

SUMMARY OF THE INVENTION

The present disclosure provides for, and includes, selective insecticide compositions comprising an anti-parasitic, anti-pest or insecticidal nucleic acid molecule having a sequence that is essentially complementary or essentially identical to a region of a calmodulin gene sequence or an RNA transcribed therefrom. In some aspects, the composition further comprises an excipient.

Several embodiments relate to an anti-parasitic, anti-pest or insecticidal nucleic acid molecule that is essentially complementary or essentially identical to a region of a *Varroa* calmodulin gene sequence, or an RNA transcribed therefrom and does not comprise a sequence of 19 or more contiguous nucleotides that are 100% identical or complementary to a gene sequence of a non-target organism. In some embodiments, the anti-parasitic, anti-pest or insecticidal nucleic acid molecule comprises deletion of one or more nucleic acids in comparison to a reference *Varroa* calmodulin gene sequence selected from SEQ ID NOs: 1-4, 6, 23, 26-35, 69-89 and 93 such that the anti-parasitic, anti-pest or insecticidal nucleic acid molecule does not comprise a sequence of 19 or more contiguous nucleotides that are 100% identical or complementary to a gene sequence of a non-target organism. In some embodiments, the non-target organism gene sequence is an ortholog of the *Varroa* calmodulin gene sequence. In some embodiments, the non-target organism gene sequence is an homolog of the *Varroa* calmodulin gene sequence. In some embodiments, the non-target organism gene sequence is unrelated to the *Varroa* calmodulin gene sequence. In one aspect, the anti-parasitic, anti-pest or insecticidal nucleic acid molecule has at least one nucleotide deleted in said region in comparison to the targeted calmodulin gene sequence. In some embodiments, the anti-parasitic, anti-pest or insecticidal nucleic acid molecule has at least two, at least three, or at least four nucleotides deleted in said region in comparison to the targeted calmodulin gene sequence. In some embodiments, the at least two, at least three, or at least four deleted nucleotides are contiguous in the targeted calmodulin gene sequence. In other embodiments, the at least two, at least three, or at least four deleted nucleotides are not contiguous in the targeted calmodulin gene sequence. In some embodiments, the anti-parasitic, anti-pest or insecticidal nucleic acid comprises a sequence essentially identical or essentially complementary to a sequence selected from SEQ ID NOs: 90-92 and 94.

In one aspect, the nucleic acid molecule in the selective insecticide composition is a dsRNA. In some aspects, the dsRNA is an siRNA.

In one aspect, the anti-parasitic, anti-pest or insecticidal nucleic acid molecule has at least 80%, 85%, 90%, 95%, 96%, 97%, 98%, 99% or 100% sequence identity to a sequence selected from SEQ ID NOs:1-4, 6, 23, 26-35, 69-89 and 93. In another aspect, the anti-parasitic, anti-pest or insecticidal nucleic acid molecule has at least 80%, 85%, 90%, 95%, 96%, 97%, 98%, 99%, or 100% sequence identity to a sequence selected from SEQ ID NOs: 90-92 and 94. In some aspects, the anti-parasitic, anti-pest or insecticidal nucleic acid molecule comprises at least 18 contiguous nucleotides of a sequence selected from SEQ ID NOs: 1-4, 6, 23, 26-35, and 69-93. In some aspects, the anti-parasitic, anti-pest or insecticidal nucleic acid does not comprise a sequence of 19 or more contiguous nucleotides that are 100% identical or complementary to a gene sequence of a non-target organism. In some aspects, the anti-parasitic, anti-pest or insecticidal nucleic acid molecule consists of a sequence selected from SEQ ID NOs: 1-4, 6, 23, 26-35, and 69-93.

In one aspect, the selective insecticide composition further comprises one or more anti-parasitic, anti-pest or insecticidal nucleic acid molecules that are essentially complementary or essentially identical to a first region of a calmodulin gene sequence. In some aspects, the one or more nucleic acid molecules comprise a second nucleic acid sequence complementary to a second region of a calmodulin gene sequence. In some embodiments, the anti-parasitic, anti-pest or insecticidal nucleic acid does not comprise a sequence of 19 or more contiguous nucleotides that are 100% identical or complementary to a gene sequence of a non-target organism. In some embodiments, the anti-parasitic, anti-pest or insecticidal nucleic acid molecule has at least one, at least two, at least three, or at least four nucleotide deletions in said first region and/or second region in comparison to a target calmodulin gene sequence. In some embodiments, the target calmodulin gene sequence is essentially identical or essentially complementary to a sequences selected from SEQ ID NOs: 1-4, 6, 23, 26-35, 69-89 and 93, or a fragment thereof. In some embodiments, the at least two, at least three, or at least four deleted nucleotides are contiguous in the target calmodulin gene sequence. In other embodiments, the at least two, at least three, or at least four deleted nucleotides are not contiguous in the target calmoduline gene sequence. In some embodiments, the anti-parasitic, anti-pest or insecticidal nucleic acid comprises a sequence essentially identical or essentially complementary to a sequence selected from SEQ ID NOs: 90-92.

In one aspect, the selective insecticide composition is bee-ingestible, bee-absorbable, mite-ingestible, or mite-absorbable.

In one aspect, the excipient is selected from the group consisting of protein, pollen, carbohydrate, polymer, liquid solvent, sugar syrup, sugar solid, and semi-solid feed. In some aspects, the liquid solvent is selected from the group consisting of sucrose solution and corn syrup solution. In some aspects, the protein is selected from the group consisting of pollen and soy protein. In another aspect, the excipient is a solid selected from sugar, a sugar substitute, or a sugar supplement. In some aspects, the sugar solid comprises sugar microparticles impregnated with dsRNA nucleic acid.

In one aspect, the instant application discloses bee-ingestible compositions comprising a bee feed and a nucleic acid molecule having a sequence that is essentially identical or essentially complementary to one or more regions of a calmodulin gene sequence, or an RNA transcribed therefrom. In some embodiments, the nucleic acid molecule is essentially complementary or essentially identical to a region of a *Varroa* calmodulin gene sequence, or an RNA transcribed therefrom, and does not comprise a sequence of 19 or more contiguous nucleotides that are 100% identical or complementary to a gene sequence of a non-target organism. In some embodiments, the nucleic acid molecule has at least one, at least two, at least three, or at least four nucleotides deleted in said one or more regions in comparison to a target *Varroa* calmoduline gene sequence. In some embodiments, the target *Varroa* calmoduline gene sequence is essentially complementary or essentially identical to a sequence selected from SEQ ID NOs: 1-4, 6, 23, 26-35, 69-89 and 93, or a fragment thereof. In some embodiments, the at least two, at least three, or at least four deleted nucleotides are contiguous in the targeted calmoduline gene sequence. In other embodiments, the at least two, at least three, or at least four deleted nucleotides are not contiguous in the targeted calmoduline gene sequence. In some embodiments, the nucleic acid molecule comprises a sequence essentially identical or essentially complementary to a sequence selected from SEQ ID NOs: 90-92 and 94. In some aspects, the bee feed comprises a bee food selected from the group consisting of corn syrup, a pollen substitute, pollen, a pollen patty, and a fondant. In some aspects, the bee feed further comprises one or more of a mineral salt, an essential oil, Brewers Yeast, yeast extract, trehalose, tryptone, dry milk, lecithin, and Vitamin C. Examples of essential oils include, but are not limited to, wintergreen oil, spearmint oil, peppermint oil, lemongrass oil and tea tree oil.

In another aspect, the instant application discloses a nucleic acid construct encoding an anti-parasitic, anti-pest or insecticidal nucleic acid sequence that is essentially identical or complementary to a region of a calmodulin gene sequence, or an RNA transcribed therefrom, operably linked to a promoter sequence functional in a host cell and capable of producing a dsRNA when introduced into said host cell. In some embodiments, the anti-parasitic, anti-pest or insecticidal nucleic acid is essentially complementary or essentially identical to a region of a targeted calmodulin gene sequence, or an RNA transcribed therefrom and does not comprise a sequence of 19 or more contiguous nucleotides that are 100% identical or complementary to a gene sequence of a non-target organism. In some embodiments, the anti-parasitic, anti-pest or insecticidal nucleic acid sequence comprises a deletion of at least one, at least two, at least three, or at least four nucleotides in comparison to a targeted calmoduline gene sequence. In some embodiments, the targeted calmoduline gene sequence is essentially identical or essentially complementary to a sequence selected from SEQ ID NOs: 1-4, 6, 23, 26-35, 69-89 and 93, or a fragment thereof. In some embodiments, the at least two, at least three, or at least four deleted nucleotides are contiguous in the targeted calmoduline gene sequence. In other embodiments, the at least two, at least three, or at least four deleted nucleotides are not contiguous in the targeted calmoduline gene sequence. In some embodiments, the anti-parasitic, anti-pest or insecticidal nucleic acid comprises a sequence essentially identical or essentially complementary to a sequence selected from SEQ ID NOs: 90-92 and 94. In some aspects, the nucleic acid construct further comprises at least one regulatory element selected from the group consisting of translation leader sequences, introns, enhancers, stem-loop structures, repressor binding sequences, termination sequences, pausing sequences, and polyadenylation recognition sequences. In some aspects, the host cell is a bacterial or yeast cell.

In another aspect, the instant application discloses a method of providing a composition to a honeybee, comprising providing the bee an effective amount of a composition comprising an anti-parasitic, anti-pest or insecticidal nucleic acid that is essentially identical or essentially complementary to one or more regions of a calmodulin gene sequence, or an RNA transcribed therefrom, whereby the nucleic acid is present in honeybee tissue. In some embodiments, the anti-parasitic, anti-pest or insecticidal nucleic acid is essentially complementary or essentially identical to a region of a targeted calmodulin gene sequence, or an RNA transcribed therefrom and does not comprise a sequence of 19 or more contiguous nucleotides that are 100% identical or complementary to a gene sequence of a non-target organism. In some embodiments, the non-target organism is a honeybee. In some embodiments, the anti-parasitic, anti-pest or insecticidal nucleic acid comprises deletion of at least one, at least two, at least three, or at least four nucleotides in said one or more regions in comparison to a targeted calmoduline gene sequence. In some embodiments, the targeted calmoduline gene sequence is essentially identical or essentially complementary to a sequence selected from SEQ ID NOs: 1-4, 6, 23, 26-35, 69-89 and 93, or a fragment thereof. In some embodiments, the at least two, at least three, or at least four deleted nucleotides are contiguous in the targeted calmoduline gene sequence. In other embodiments, the at least two, at least three, or at least four deleted nucleotides are not contiguous in the targeted calmoduline gene sequence. In some embodiments, the anti-parasitic, anti-pest or insecticidal nucleic acid comprises a sequence essentially identical or essentially complementary to a sequence selected from SEQ ID NOs: 90-92 and 94. In another aspect, the instant application discloses a method of treating or preventing disease in a honeybee colony, comprising providing an effective amount of a composition comprising an anti-parasitic, anti-pest or insecticidal nucleic acid that is essentially identical or essentially complementary to one or more regions of a calmodulin gene sequence to a honeybee whereby the nucleic acid is present in honeybee tissue. In some aspects, the calmodulin gene sequence is a *Varroa destructor* calmodulin gene sequence. In some embodiments, the anti-parasitic, anti-pest or insecticidal nucleic acid is essentially complementary or essentially identical to a region of a *Varroa* calmodulin gene sequence, or an RNA transcribed therefrom and does not comprise a sequence of 19 or more contiguous nucleotides that are 100% identical or complementary to a gene sequence of a non-target organism. In some embodiments, the anti-parasitic, anti-pest or insecticidal nucleic acid comprises deletion of at least one, at least two, at least three, or at least four nucleotides in one or more regions in comparison to a targeted calmoduline gene sequence. In some embodiments, the targeted calmoduline gene sequence is essentially complementary or essentially identical to a nucleic acid sequence selected from SEQ ID NOs: 1-4, 6, 23, 26-35, 69-89 and 93, or a fragment thereof. In some embodiments, the at least two, at least three, or at least four deleted nucleotides are contiguous in the targeted calmoduline gene sequence. In other embodiments, the at least two, at least three, or at least four deleted nucleotides are not contiguous in the targeted calmoduline gene sequence.

In another aspect, the instant application discloses a method of reducing parasitation of a bee by *Varroa destructor*, comprising providing the bee an effective amount of an anti-parasitic, anti-pest or insecticidal nucleic acid composition, wherein the nucleic acid is essentially identical or essentially complementary to one or more regions of a *Varroa destructor* calmodulin gene sequence, or an RNA transcribed therefrom, thereby reducing the parasitation of the bee by *Varroa destructor*. In some embodiments, the anti-parasitic, anti-pest or insecticidal nucleic acid comprises a sequence essentially identical or essentially complementary to a sequence selected from SEQ ID NOs: 90-92 and 94.

In another aspect, the instant application discloses a method of reducing the parasite load of a honeybee hive, comprising providing said hive an effective amount of an anti-parasitic, anti-pest or insecticidal nucleic acid that is essentially identical or essentially complementary to one or more regions of a parasite calmodulin gene sequence, or an RNA transcribed therefrom, whereby the parasite load of said hive is reduced. In some embodiments, the anti-parasitic, anti-pest or insecticidal nucleic acid does not comprise a sequence of 19 or more contiguous nucleotides that are 100% identical or complementary to a gene sequence of a non-target organism. In some embodiments, the anti-parasitic, anti-pest or insecticidal nucleic acid molecule comprises deletion of at least one, at least two, at least three, or at least four nucleotides in one or more regions in comparison to a targeted parasite calmoduline gene sequence. In some embodiments, the targeted parasite calmoduline gene sequence is essentially complementary or essentially identical to a nucleic acid sequence selected from SEQ ID NOs: 1-4, 6, 23, 26-35, 69-89 and 93. In some embodiments, the at least two, at least three, or at least four deleted nucleotides are contiguous in the targeted calmoduline gene sequence. In other embodiments, the at least two, at least three, or at least four deleted nucleotides are not contiguous in the targeted calmoduline gene sequence. In some embodiments, the anti-parasitic, anti-pest or insecticidal nucleic acid comprises a sequence essentially identical or essentially complementary to a sequence selected from SEQ ID NOs: 90-92 and 94.

In another aspect, the instant application discloses a method of selectively treating an arthropod species for parasites, comprising delivering an effective amount of an anti-parasitic, anti-pest or insecticidal nucleic acid that is essentially identical or essentially complementary to one or more regions of a parasite calmodulin gene sequence, or an RNA transcribed therefrom, to an arthropod species. In some embodiments, the anti-parasitic, anti-pest or insecticidal nucleic acid does not comprise a sequence of 19 or more contiguous nucleotides that are 100% identical or complementary to a gene sequence of a non-target organism. In some embodiments, the anti-parasitic, anti-pest or insecticidal nucleic acid has at least one, at least two, at least three, or at least four nucleotides deleted in one or more regions in comparison to a targeted arthropod calmoduline gene sequence. In some embodiments, the targeted arthropod calmoduline gene sequence is essentially complementary or essential identical to a sequence selected from SEQ ID NOs: 1-4, 6, 23, 26-35, 69-89 and 93, or a fragment thereof. In some embodiments, the at least two, at least three, or at least four deleted nucleotides are contiguous in the targeted calmoduline gene sequence. In other embodiments, the at least two, at least three, or at least four deleted nucleotides are not contiguous in the targeted calmoduline gene sequence. In some embodiments, the anti-parasitic, anti-pest or insecticidal nucleic acid comprises a sequence essentially identical or essentially complementary to a sequence selected from SEQ ID NOs: 90-92 and 94.

In another aspect, the instant application provides for, and discloses a method of treating or preventing Colony Collapse Disorder in a honeybee colony, comprising providing an effective amount of a composition to a honeybee colony comprising an anti-parasitic, anti-pest or insecticidal nucleic acid molecule having a sequence that is essentially identical to or essentially complementary to one or more regions of a *Varroa destructor* calmodulin gene sequence whereby the level of *Varroa destructor* infestation is reduced or prevented. In some embodiments, the anti-parasitic, anti-pest or insecticidal nucleic acid does not comprise a sequence of 19 or more contiguous nucleotides that are 100% identical or complementary to a gene sequence of a non-target organism. In some embodiments, the anti-parasitic, anti-pest or insecticidal nucleic acid has at least one, at least two, at least three, or at least four nucleotides deleted in one or more regions in comparison to a targeted calmoduline gene sequence. In some embodiments, the targeted arthropod calmoduline gene sequence is essentially complementary or essential identical to a sequence selected from SEQ ID NOs: 1-4, 6, 23, 26-35, 69-89 and 93, or a fragment thereof. In some embodiments, the at least two, at least three, or at least four deleted nucleotides are contiguous in the targeted calmoduline gene sequence. In other embodiments, the at least two, at least three, or at least four deleted nucleotides are not contiguous in the targeted calmoduline gene sequence.

DETAILED DESCRIPTION

Figure 1:
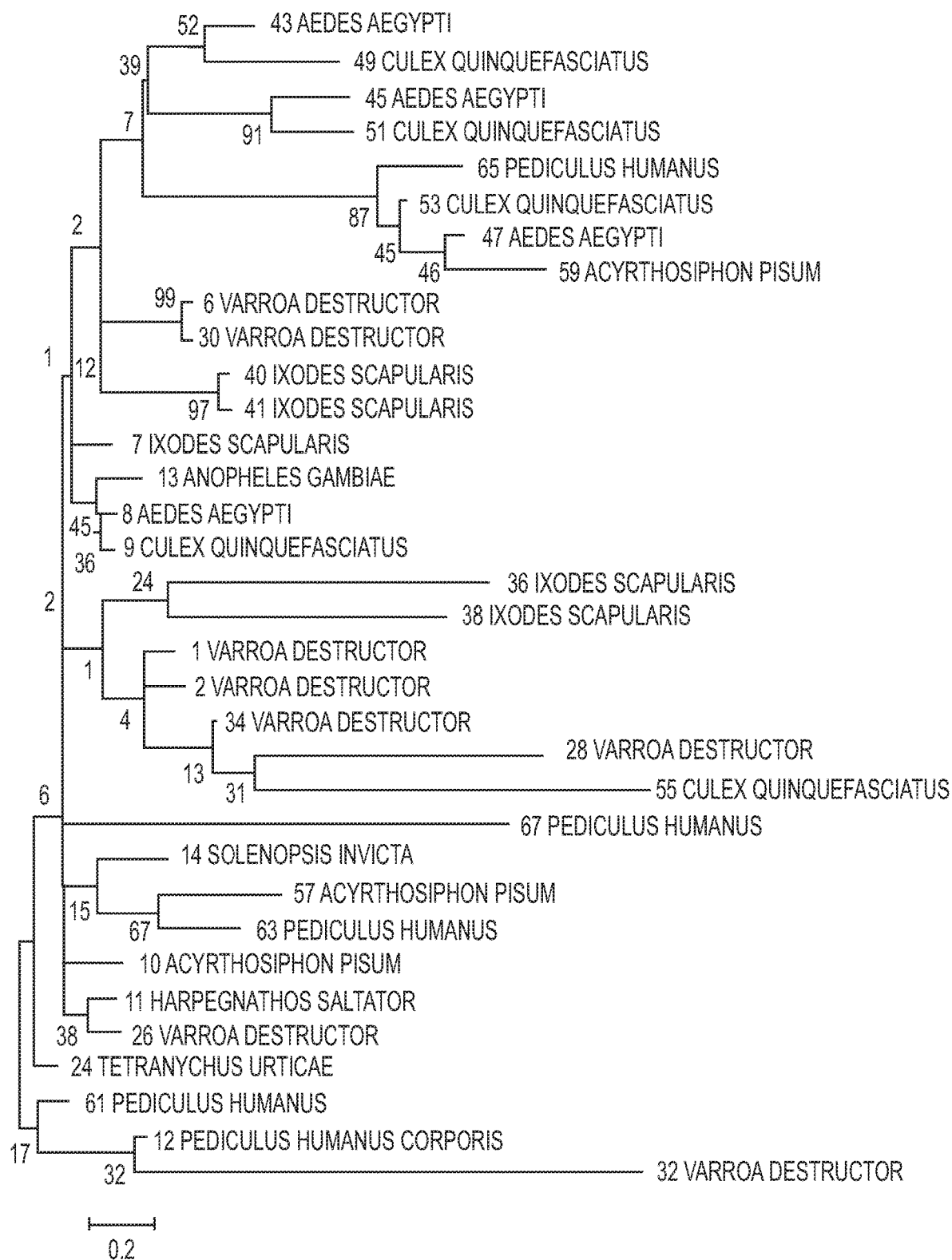
FIG. 1 presents a phylogenetic tree for Calmodulin (CAM) genes from different species. The number immediately preceding the species name corresponds to a Sequence Identification Number (SEQ ID NO).

Unless defined otherwise, technical and scientific terms as used herein have the same meaning as commonly understood by one of ordinary skill in the art. One skilled in the art will recognize many methods can be used in the practice of the present disclosure. Indeed, the present disclosure is in no way limited to the methods and materials described. Any references cited herein are incorporated by reference in their entireties. For purposes of the present disclosure, the following terms are defined below.

It is understood that any Sequence Identification Number (SEQ ID NO) disclosed in the instant application can refer to either a DNA sequence or a RNA sequence, depending on the context where that SEQ ID NO is mentioned, even if that SEQ ID NO is expressed only in a DNA sequence format or a RNA sequence format. For example, SEQ ID NO: 1 is expressed in a DNA sequence format (e.g., reciting T for thymine), but it can refer to either a DNA sequence that corresponds to a mature *Varroa destructor* calmodulin nucleic acid sequence, or the RNA sequence of a mature *Varroa destructor* calmodulin molecule nucleic acid sequence. Similarly, though SEQ ID NO: 3 is expressed in a RNA sequence format (e.g., reciting U for uracil), depending on the actual type of molecule being described, SEQ ID NO: 3 can refer to either the sense or antisense strand of a dsRNA, or the sequence of a DNA molecule that corresponds to the RNA sequence shown. In any event, both DNA and RNA molecules having the sequences disclosed with any substitutes are envisioned.

As used herein the term "about" refers to ±10%.

As used herein, the singular form "a", "an" and "the" include plural references unless the context clearly dictates otherwise. For example, the term "a compound" or "at least one compound" may include a plurality of compounds, including mixtures thereof.

As used herein, "essentially identical" or "essentially complementary" refers to a nucleic acid (or at least one strand of a double-stranded nucleic acid or portion thereof, or a portion of a single strand nucleic acid) that hybridizes under physiological conditions to the endogenous gene, an RNA transcribed therefrom, or a fragment thereof, to effect regulation or suppression of the endogenous gene. For example, in some aspects, a nucleic acid has 100 percent sequence identity or at least about 83, 84, 85, 86, 87, 88, 89, 90, 91, 92, 93, 94, 95, 96, 97, 98, or 99 percent sequence identity when compared to a region of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or more contiguous nucleotides in the target gene or RNA transcribed from the target gene. In some aspects, a nucleic acid has 100 percent sequence complementarity or at least about 83, 84, 85, 86, 87, 88, 89, 90, 91, 92, 93, 94, 95, 96, 97, 98, or 99 percent sequence complementarity when compared to a region of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or more contiguous nucleotides in the target gene or RNA transcribed from the target gene. In some aspects, a nucleic acid has 100 percent sequence identity with or complementarity to one allele or one family member of a given target gene (coding or non-coding sequence of a gene). In some aspects, a nucleic acid has at least about 83, 84, 85, 86, 87, 88, 89, 90, 91, 92, 93, 94, 95, 96, 97, 98, or 99 percent sequence identity with or complementarity to multiple alleles or family members of a given target gene. In some aspects, a nucleic acid has 100 percent sequence identity with or complementarity to multiple alleles or family members of a given target gene.

In some aspects, the nucleic acid is essentially identical or essentially complementary to at least about 10, 15, 20, 25, 30, 35, 40, 45, 50, 55, 60, 65, 70 or more contiguous nucleotides of an endogenous calmodulin gene of a targeted pest, or an RNA transcribed therefrom. In some aspects, the nucleic acid does not comprise a sequence of 19 or more contiguous nucleotides that are 100% identical or complementary to a gene sequence of a non-target organism. In some aspects, the nucleic acid comprises at least one nucleotide deletion in comparison to a targeted calmoduline gene sequence selected from SEQ ID NOs: 1-4, 6, 23, 26-35, 69-89 and 93. In an aspect, the nucleic acid sequence has at least one nucleotide deleted compared an endogenous reference calmoduline gene sequence of a targeted pest, or an RNA transcribed therefrom such that the nucleic acid does not comprise a sequence of 19 or more contiguous nucleotides that are 100% identical or complementary to a gene sequence of a non-target organism. The nucleic acid may be a single-stranded DNA, a single-stranded RNA, a double-stranded RNA, a double-stranded DNA, or a double-stranded DNA/RNA hybrid. In some aspects, the targeted calmodulin gene sequence is a *Varroa destructor* calmodulin gene sequence. In an aspect, the targeted calmodulin gene sequence is a calmodulin gene sequence selected from SEQ ID NO: 1. In an aspect, the targeted calmodulin gene sequence is a calmodulin gene sequence selected from SEQ ID NO: 2. In an aspect, the targeted calmodulin gene sequence is a calmodulin gene sequence selected from SEQ ID NO: 3. In an aspect, the targeted calmodulin gene sequence is a calmodulin gene sequence selected from SEQ ID NO: 4. In an aspect, the targeted calmodulin gene sequence is a calmodulin gene sequence selected from SEQ ID NO: 69. In an aspect, the targeted calmodulin gene sequence is a calmodulin gene sequence selected from SEQ ID NO: 70. In an aspect, the targeted calmodulin gene sequence is a calmodulin gene sequence selected from SEQ ID NOs: 71-87. In an aspect, the targeted calmodulin gene sequence is a calmodulin gene sequence selected from SEQ ID NO: 88. In an aspect, the targeted calmodulin gene sequence is a calmodulin gene sequence selected from SEQ ID NO: 89. In an aspect, the targeted calmodulin gene sequence is a calmodulin gene sequence selected from SEQ ID NO: 93. In an aspect, the nucleic acid has at least one nucleotide deleted compared to an endogenous calmoduline gene sequence of a targeted pest, or an RNA transcribed therefrom. In an aspect, the nucleic acid has at least two, at least three, at least four, at five, at least six, at least seven, at least eight, at least nine, or at least ten nucleotides deleted compared to an endogenous calmodulin gene sequence of a targeted pest, or an RNA transcribed therefrom. In some aspects, the at least two, at least three, at least four, at five, at least six, at least seven, at least eight, at least nine, or at least ten deleted nucleotides are contiguous in targeted endogenous calmoduline gene sequences. In other aspects, the at least two, at least three, at least four, at five, at least six, at least seven, at least eight, at least nine, or at least ten deleted nucleotides are not contiguous in the targeted endogenous calmoduline gene sequences. In one aspect, the targeted calmodulin gene sequence is essentially complementary or essentially identical to a sequence selected from SEQ ID NOs: 1-4, 6, 23, 26-35, 69-89 and 93. In one aspect, the nucleic acid comprises a sequence selected from SEQ ID NOs: 90-92 and 94.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition. In an aspect according to the present disclosure, a composition may be used to treat an organism or colony of organisms for the effects of parasitation. In an aspect, a nucleic acid composition may be used to treat a host organism or colony for parasites. In an aspect, the host organism is a bee and the parasite is the mite, *Varroa destructor*.

As used herein, the phrase "RNA silencing" refers to a group of regulatory mechanisms (e.g. RNA interference (RNAi), transcriptional gene silencing (TGS), post-transcriptional gene silencing (PTGS), quelling, co-suppression, and translational repression) mediated by RNA molecules which result in the inhibition or "silencing" of the expression of a corresponding protein-coding gene or bee pathogen RNA sequence. RNA silencing has been observed in many types of organisms, including plants, animals, and fungi. In aspects according the present disclosure, nucleic acid compositions provide for RNA silencing. In certain aspects, the nucleic acid compositions provide for RNA silencing and mortality in a parasite.

As used herein, the term "RNA silencing agent" refers to a nucleic acid which is substantially homologous or complementary to a polynucleotide sequence of a target gene or an RNA expressed from the target gene or a fragment thereof and is capable of inhibiting or "silencing" the expression of a target gene. RNA silencing agents are generally described in relation to the target sequence against which the RNA silencing agent is directed. The target sequence can include, but is not limited to, a promoter region, 5' untranslated regions, transcript encoding regions that can include intronic regions, 3' untranslated regions, or combinations of these regions. In some embodiments, the target sequence can include coding or non-coding sequence or both. In some embodiments, the target sequence is identical to or complementary to a messenger RNA, e.g., in embodiments where the target sequence is a cDNA. In some embodiments, the target sequence is a native calmodulin gene sequence that is endogenously expressed in a target pest. In some embodiments, the target sequence is a calmoduline gene sequence selected from SEQ ID NOs: 1-4, 6, 23, 26-35, 69-89 and 93, or a part thereof. In some embodiments, the reference calmodulin gene sequence comprises at least 18 contiguous nucleotides, at least 19 contiguous nucleotides, at least 20 contiguous nucleotides, at least 21 contiguous nucleotides, at least 22 contiguous nucleotides or more of a sequence selected from SEQ ID NOs: 1-4, 6, 23, 26-35, 69-89 and 93.

In certain aspects, the RNA silencing agent is capable of preventing complete processing (e.g., the full translation and/or expression) of an mRNA molecule through a post-transcriptional silencing mechanism. RNA silencing agents can be single- or double-stranded RNA or single- or double-stranded DNA or double-stranded DNA/RNA hybrids or modified analogues thereof. In some aspects, the RNA silencing agents are selected from the group consisting of (a) a single-stranded RNA molecule (ssRNA), (b) a ssRNA molecule that self-hybridizes to form a double-stranded RNA molecule, (c) a double-stranded RNA molecule (dsRNA), (d) a single-stranded DNA molecule (ssDNA), (e) a ssDNA molecule that self-hybridizes to form a double-stranded DNA molecule, and (f) a single-stranded DNA molecule including a modified Pol III gene that is transcribed to an RNA molecule, (g) a double-stranded DNA molecule (dsDNA), (h) a double-stranded DNA molecule including a modified Pol III promoter that is transcribed to an RNA molecule, (i) a double-stranded, hybridized RNA/DNA molecule, or combinations thereof. In some aspects these polynucleotides include chemically modified nucleotides or non-canonical nucleotides. In some aspects, the RNA silencing agents are noncoding RNA molecules, for example RNA duplexes comprising paired strands, as well as precursor RNAs from which such small non-coding RNAs can be generated. In some aspects, the RNA silencing agents are dsRNAs such as siRNAs, miRNAs and shRNAs.

In one aspect, the RNA silencing agent is capable of inducing RNA interference. In another aspect, the RNA silencing agent is capable of mediating translational repression. In an aspect, the RNA silencing agent is capable of inhibiting the expression of a calmodulin gene. In another aspect, the RNA silencing agent is capable of being used in methods to inhibit the expression of a target gene and thereby kill a target organism. In certain aspects, the target gene is a calmodulin gene and the target organism is *Varroa destructor*.

RNA interference refers to the process of sequence-specific post-transcriptional gene silencing in animals mediated by small RNAs. The corresponding process in plants is commonly referred to as post-transcriptional gene silencing or RNA silencing and is also referred to as quelling in fungi. While not being limited to any particular theory, the process of post-transcriptional gene silencing is thought to be an evolutionarily-conserved cellular defense mechanism used to prevent the expression of foreign genes and is commonly shared by diverse flora and phyla.

Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA. In aspects according to the present disclosure, a nucleic acid composition results in RNA interference in a target organism. In certain aspects, the nucleic acid composition results in RNA interference in *Varroa destructor* when present in the host organism, the bee. According to aspects of the present disclosure, a selective insecticide may cause RNA interference in the targeted organism, while having no RNA interference activity in non-target organisms.

As used herein, "small RNA" refers to any RNA molecule that is at least 15 base pairs in length, generally 15-30 nucleotides long, preferably 20-24 nucleotides long. In aspects according to the present disclosure, a "small RNA" is greater than 50 base pairs in length. In an aspect, the small RNA is greater than 50 base pairs in length but less than about 500 base pairs. In an aspect, the small RNA is greater than 100 base pairs in length but less than about 500 base pairs. In an aspect, the small RNA is greater than 200 base pairs in length but less than about 500 base pairs. A small RNA can be either double-stranded or single-stranded. Small RNA includes, without limitation, miRNA (microRNA), ta-siRNA(trans activating siRNA), siRNA, activating RNA (RNAa), nat-siRNA (natural anti-sense siRNA), hc-siRNA (heterochromatic siRNA), cis-acting siRNA, lmiRNA (long miRNA), lsiRNA (long siRNA) and easiRNA (epigenetically activated siRNA) and their respective precursors. In some embodiments, siRNA molecules of the disclosure are miRNA molecules, ta-siRNA molecules and RNAa molecules and their respective precursors. A small RNA may be processed in vivo by an organism to an active form. According to aspects of the present disclosure, a selective insecticide may be a small RNA.

In aspects according to the present disclosure, a small RNA is provided directly in a composition. In other aspects, a small RNA is produced by in vivo by an organism from either a DNA or an RNA precursor. In some aspects, the small RNA is produced as a product of a transgene in an organism, for example a yeast or bacterial cell. In certain aspects, a small RNA produced as a product of a transgene is produced as a precursor that is processed in vivo after ingestion or absorption by an organism. In other aspects, a small RNA produced as a product of a transgene is produced as a precursor that is processed in vivo after ingestion or absorption by an organism.

In some aspects, the RNA silencing agent may be an artificial microRNA. As used herein, an "artificial microRNA" (amiRNA) is a type of miRNA which is derived by replacing native miRNA duplexes from a natural miRNA precursor. Generally, an artificial miRNA is a non-naturally-existing miRNA molecule produced from a pre-miRNA molecule scaffold engineered by exchanging a miRNA sequence of a naturally-existing pre-miRNA molecule for a sequence of interest which corresponds to the sequence of an artificial miRNA. In aspects according to the present disclosure a nucleic acid composition may be an amiRNA composition.

Various studies demonstrate that long dsRNAs can be used to silence gene expression without inducing the stress response or causing significant off-target effects—see for example (Strat et al., Nucleic Acids Research, 2006, Vol. 34, No. 13 3803-3810; Bhargava A et al. Brain Res. Protoc. 2004; 13:115-125; Diallo M., et al., Oligonucleotides. 2003; 13:381-392; Paddison P. J., et al., Proc. Natl Acad. Sci. USA. 2002; 99:1443-1448; Tran N., et al., FEBS Lett. 2004; 573:127-134). The present disclosure provides for, and includes, methods and compositions having long dsRNAs.

As used herein, with respect to a nucleic acid sequence, nucleic acid molecule, or a gene, the term "natural" or "native" means that the respective sequence or molecule is present in a wild-type organism, that has not been genetically modified or manipulated by man. A small RNA molecule naturally targeting a target gene means a small RNA molecule present in a wild-type organism, the cell has not been genetically modified or manipulated by man which is targeting a target gene naturally occurring in the respective organism.

As used herein, the terms "homology" and "identity" when used in relation to nucleic acids, describe the degree of similarity between two or more nucleotide sequences. The percentage of "sequence identity" between two sequences is determined by comparing two optimally aligned sequences over a comparison window, such that the portion of the sequence in the comparison window may comprise additions or deletions (gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. A sequence that is identical at every position in comparison to a reference sequence is said to be identical to the reference sequence and vice-versa. An alignment of two or more sequences may be performed using any suitable computer program. For example, a widely used and accepted computer program for performing sequence alignments is CLUSTALW v1.6 (Thompson, et al. Nucl. Acids Res., 22: 4673-4680, 1994).

As used herein, the terms "exogenous polynucleotide" and "exogenous nucleic acid molecule" relative to an organisms refer to a heterologous nucleic acid sequence which is not naturally expressed within that organism. An exogenous nucleic acid molecule may be introduced into an organism in a stable or transient manner. An exogenous nucleic acid molecule may comprise a nucleic acid sequence which is identical or partially homologous to an endogenous nucleic acid sequence of the organism or a pest or pathogen of that organism. In certain aspects, an "exogenous polynucleotide" and "exogenous nucleic acid molecule" may refer to a parasite nucleic acid sequence expressed or present in a host, either transiently or stably. The present disclosure provides for, and includes, compositions comprising exogenous polynucleotides and exogenous nucleic acid molecules and methods for introducing them into a target organism. In some aspects, the present disclosure provides for, and includes, compositions comprising exogenous polynucleotides and exogenous nucleic acid molecules and methods for introducing them into a non-target organism that is a host to the target organism.

As used herein, a "control organism" means an organism that does not contain the recombinant DNA, small RNA, or other nucleic acid (e.g., protein, miRNA, small RNA-resistant target mRNA, dsRNA, target mimic) that provides for control of a pest or parasite. Control organisms are generally from same species and of the same developmental stage which is grown under the same growth conditions as the treated organism. Similarly, a "control colony" means a colony of organisms that do not contain the recombinant DNA, small RNA, or other nucleic acid (e.g., protein, miRNA, small RNA-resistant target mRNA, target mimic) that provides for control of a pest or parasite. Control colonies of organisms are generally from same species and of the same developmental stage which are grown under the same growth conditions as the treated colony of organisms. As a non-limiting example, a control organism could be a bee provided with a composition that does not contain a nucleic acid of the present disclosure. In another non-limiting example, a control organism could be a bee provided with a composition that contains a nucleic acid that does not act a an RNA silencer in either a bee or a parasite, such as SEQ ID NO: 5.

As used herein, the terms "improving," "improved," "increasing," and "increased" refer to at least about 2%, at least about 3%, at least about 4%, at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, or greater increase in an organism or colony population, in increased productivity of an organism or colony (e.g., increased honey productions), increase growth rate of an organism or colony, or increased reproductive rate as compared to a control organism or colony. The present disclosure provides for methods of improving the health of an organism or colony by providing a selective insecticidal composition.

As used herein, "a reduction" of the level of an agent such as a protein or mRNA means that the level is reduced relative to an organism or colony lacking a nucleic acid capable of reducing the agent. Also as used herein, "a reduction" in reference to parasitation or parasite load, means that the level is reduced relative to an organism or colony lacking a nucleic acid, such as a dsRNA molecule, capable of reducing the viability, fecundity or number of the parasite. The present disclosure provides for, and includes, methods and compositions for reducing the level of a protein or mRNA and reducing the level or number of parasites.

As used herein, the term "at least a partial reduction" of the level of an agent, such as a protein or mRNA, means that the level is reduced at least 25% relative to an organism or colony lacking a nucleic acid, such as a dsRNA molecule, capable of reducing the agent. Also as used herein, "at least a partial reduction" in reference to parasitation or parasite load, means that the level is reduced at least 25% relative to an organism or colony lacking a nucleic acid, such as a dsRNA molecule, capable of reducing the viability, fecundity or number of the parasite. The present disclosure provides for, and includes, methods and compositions for at least partially reducing the level of a protein or mRNA and at least partially reducing the level or number of parasites.

As used herein, "a substantial reduction" of the level of an agent such as a protein or mRNA means that the level is reduced relative to an organism or colony lacking a nucleic acid, such as a dsRNA molecule, capable of reducing the agent, where the reduction of the level of the agent is at least 75%. Also as used herein, "a substantial reduction" in reference to parasitation or parasite load, means that the level is reduced at least 75% relative to an organism or colony lacking a nucleic acid, such as a dsRNA molecule, capable of reducing the viability, fecundity or number of the parasite. The present disclosure provides for, and includes, methods and compositions for substantially reducing the level of a protein or mRNA and substantially reducing the level or number of parasites.

As used herein, "an effective elimination" of an agent such as a protein or mRNA is relative to an organism or colony lacking a dsRNA molecule capable of reducing the agent, where the reduction of the level of the agent is greater than 95%. An agent, such as a dsRNA molecule, is preferably capable of providing at least a partial reduction, more preferably a substantial reduction, or most preferably effective elimination of another agent such as a protein or mRNA, or a parasite, wherein the agent leaves the level of a second agent, or host organism, essentially unaffected, substantially unaffected, or partially unaffected. Also as used herein, "an effective elimination" in reference to parasitation or parasite load, means that the level is reduced at least 95% relative to an organism or colony lacking a nucleic acid, such as a dsRNA molecule, capable of reducing the viability, fecundity or number of the parasite. The present disclosure provides for, and includes, methods and compositions for the effective elimination of a protein or mRNA and effectively eliminating parasites.

As used herein, the terms "suppress," "repress," and "downregulate" when referring to the expression or activity of a nucleic acid molecule in an organism are used equivalently herein and mean that the level of expression or activity of the nucleic acid molecule in a cell of an organism after applying a method of the present disclosure is lower than its expression or activity in the cell of an organism before applying the method, or compared to a control organism lacking a nucleic acid molecule of the disclosure. The present disclosure provides for, and includes, methods and compositions for suppressing, repressing and down-regulating the level of a protein or mRNA and suppressing, repressing and down-regulating the level or number of parasites.

The terms "suppressed," "repressed" and "downregulated" as used herein are synonymous and mean herein lower, preferably significantly lower, expression or activity of a targeted nucleic acid molecule. Also as used herein, "suppressed," "repressed" and "downregulated" in reference to parasitation or parasite load, means that the level of parasitation or parasite load is lower, preferably significantly lower, relative to an organism or colony lacking a nucleic acid, such as a dsRNA molecule, capable of reducing the viability, fecundity or number of the parasite. The present disclosure provides for, and includes, methods and compositions for suppressing, repressing and down-regulating the expression or activity of a protein or mRNA and suppressing, repressing and down-regulating the activity of parasites.

As used herein, a "suppression," "repression," or "down-regulation" of the level or activity of an agent such as a protein, mRNA, or RNA means that the level or activity is reduced relative to a substantially identical cell, organism or colony grown under substantially identical conditions, lacking a nucleic acid molecule of the disclosure, for example, lacking the region complementary to a dsRNA or siRNA, the recombinant construct or recombinant vector of the disclosure. As used herein, "suppression," "repression," or "down-regulation" of the level or activity of an agent, such as, for example, a preRNA, mRNA, rRNA, tRNA, snoRNA, snRNA expressed by the target gene, and/or of the protein product encoded by it, means that the amount is reduced by 10% or more, for example, 20% or more, preferably 30% or more, more preferably 50% or more, even more preferably 70% or more, most preferably 80% or more, for example, 90%, relative to a cell, organism or colony lacking a recombinant nucleic acid molecule of the disclosure. The present disclosure provides for, and includes, methods and compositions for suppression, repression and downregulation of an agent such as a protein, mRNA, RNA, or parasite compared to an untreated organism or colony.

As used herein, the term "arthropod" refers to both adult and pupa of invertebrate animals having an exoskeleton (external skeleton), a segmented body, and jointed appendages. Arthropods are members of the phylum Arthropoda and includes the insects, arachnids, and crustaceans. Arthropods according to the present disclosure, include but are not limited to *Apis mellifera, Apis cerana, Trigona minima, Halictidae, Bombus* sp., fleas, flies, lice, ticks, mites, and beneficial insects. The present disclosure provides for, and includes, methods and compositions for treating arthropods as either a host or as a parasite or pest.

In an aspect, an arthropod may be an insect. In certain aspects, an insect may be a bee. As used herein, the term "bee" refers to both an adult bee and pupal cells thereof. According to one aspect, the bee is in a hive. An adult bee is defined as any of several winged, hairy-bodied, usually stinging insects of the superfamily Apoidea in the order Hymenoptera, including both solitary and social species and characterized by sucking and chewing mouthparts for gathering nectar and pollen. Examples of bee species include, but are not limited to, *Apis, Bombus, Trigona, Osmia* and the like. In one aspect, bees include, but are not limited to bumblebees (*Bombus terrestris*), honeybees (*Apis mellifera*) (including foragers and hive bees) and *Apis cerana*. The present disclosure provides for, and includes, methods and compositions for treating bees as a host for parasites, such as *Varroa* mites.

According to one aspect, a bee is part of a colony. The term "colony" refers to a population of bees comprising dozens to typically several tens of thousands of bees that cooperate in nest building, food collection, and brood rearing. A colony normally has a single queen, the remainder of the bees being either "workers" (females) or "drones" (males). The social structure of the colony is maintained by the queen and workers and depends on an effective system of communication. Division of labor within the worker caste primarily depends on the age of the bee but varies with the needs of the colony. Reproduction and colony strength depend on the queen, the quantity of food stores, and the size of the worker force. Honeybees can also be subdivided into the categories of "hive bees", usually for the first part of a workers lifetime, during which the "hive bee" performs tasks within the hive, and "forager bee", during the latter part of the bee's lifetime, during which the "forager" locates and collects pollen and nectar from outside the hive, and brings the nectar or pollen into the hive for consumption and storage. The present disclosure provides for, and includes, methods and compositions for treating insects colonies.

As used herein, the term "pest" refers to both adult and immature forms of an organism that is invasive or prolific, detrimental, troublesome, noxious, destructive, a nuisance to either plants or animals, or ecosystems. A parasite is a type of pest. It is possible for an organism to be a pest in one setting but beneficial, domesticated, or acceptable in another.

As used herein, the term "parasite" refers to both adult and immature forms of organisms that directly benefit at the expense of another, host, organism, for example by feeding on the blood or fluids of the host, living intracellularly in a host organism cell, or living within a body of a host organism. Parasites include organisms that are animals, fungi, bacterial or plants and are identified by their negative or detrimental interaction with a host. In some aspects, a parasite as used herein may in turn serve as a host to a second parasite. In some aspects, a parasite and host may be of the same type of organism (e.g., an arthropod host and an arthropod parasite).

Parasites include, but are not limited to, Acari (ticks, mites), Hippoboscoidea (flies), Ichneumonoidea (parasitic wasps), Oestridae (bot flies), Phthiraptera (lice), Siphonaptera (fleas), Tantulocarida, Pea crab, and Sacculina. As used herein, a pest may include both parasitic and non-parasitic life stages. The present disclosure provides for, and includes, methods and compositions for treating parasites. In an aspect, the parasite may be *Varroa destructor*.

As provided for, and included, in the present disclosure, parasites and/or pests include *Varroa destructor, Ixodes scapularis, Solenopsis invicta, Tetranychus urticae, Aedes aegypti, Culex quinquefasciatus, Acyrthosiphon pisum*, and *Pediculus humanus*. In aspects according to the present disclosure, selective insecticides may be selective for *Varroa destructor, Ixodes scapularis, Solenopsis invicta, Tetranychus urticae, Aedes aegypti, Culex quinquefasciatus, Acyrthosiphon pisum*, and *Pediculus humanus* and inactive, or significantly less active, against a non-target organism, such as the host organism.

As used herein, the term "excipient" refers to any inactive substance in a formulation having an active ingredient such as an anti-parasitic, anti-pest or insecticidal nucleic acid, including without limitation dsRNA, small RNAs, miRNAs and antisense RNAs. In some embodiments, an excipient includes substances that may provide additional functionality to a composition that is distinct to the anti-parasitic, anti-pest, or insecticidal nucleic acids. Excipient functions include, but are not limited to "bulking agents," "fillers," "diluents," and "carriers." Bulking up allows convenient and accurate dispensation of compositions of the present disclosure. Excipients can also serve to facilitate ingestion of the compositions by organisms and include various carbohydrates, proteins, fatty acids, pollens, and pollen substitutes. Excipients can also serve to facilitate absorption of compositions by organisms an include, for example, both aqueous and non-aqueous solutions of active ingredients. Non-limiting examples of excipients include corn syrup, sugar syrup, sugar solid, sugar semi-solids, pollen, soy protein, pollen and protein mixtures. Excipients may further comprise attractants, buffers and nutrient supplements. Compositions of the present disclosure may be coated with, encapsulated in, dissolved in, mixed with, or otherwise combined with an excipient. As used herein, the term excipient may refer to a mixture of inactive substances.

This application provides and discloses anti-parasitic, anti-pest or insecticidal nucleic acid molecules that are substantially homologous or complementary to a polynucleotide sequence of a calmodulin target gene or an RNA expressed from the calmodulin target gene or a fragment thereof and functions to suppress the expression of the calmodulin target gene or produce a knock-down phenotype. In some aspects, the anti-parasitic, anti-pest or insecticidal nucleic acid does not comprise a sequence of 19 or more contiguous nucleotides that are 100% identical or complementary to a gene sequence of a non-target organism. In some aspects, the anti-parasitic, anti-pest or insecticidal nucleic acid molecule comprises deletion of one or more nucleic acids in comparison to a calmodulin target gene such that the anti-parasitic, anti-pest or insecticidal nucleic acid molecule does not comprise a sequence of 19 or more contiguous nucleotides that are 100% identical or complementary to a gene sequence of a non-target organism. The anti-parasitic, anti-pest or insecticidal nucleic acid molecules are capable of inhibiting or "silencing" the expression of a calmodulin target gene in a target species. In some embodiments, the anti-parasitic, anti-pest or insecticidal nucleic acid molecules do not affect expression of a calmodulin gene in a non-target organism, yet are capable of inhibiting or "silencing" the expression of a calmodulin target gene in a target species. The anti-parasitic, anti-pest or insecticidal nucleic acid molecules are generally described in relation to their "target sequence." In some embodiments, the target sequence is selected from SEQ ID NOs. 1, 2 and 6-77. In some embodiments, the anti-parasitic, anti-pest or insecticidal nucleic acid molecules comprises at least one, at least two, at least three, or at least four nucleotides deleted in comparison to the target sequence. In some embodiments, the at least one, at least two, at least three, or at least four deleted nucleotides are contiguous in the target sequence. In other embodiments, the at least one, at least two, at least three, or at least four deleted nucleotides are not contiguous in the target sequence. The anti-parasitic, anti-pest or insecticidal nucleic acid molecules may be single-stranded DNA (ssDNA), single-stranded RNA (ssRNA), double-stranded RNA (dsRNA), double-stranded DNA (dsDNA), or double-stranded DNA/RNA hybrids. The nucleic acid molecules may comprise naturally-occurring nucleotides, modified nucleotides, nucleotide analogues or any combination thereof. In some embodiments, a anti-parasitic, anti-pest or insecticidal nucleic acid molecule may be incorporated within a larger polynucleotide, for example in a pri-miRNA molecule. In some embodiments, a anti-parasitic, anti-pest or insecticidal nucleic acid molecule may be processed into a small interfering RNA (siRNA). In some embodiments, nucleic acid molecules are provided or disclosed that are selectively anti-parasitical or miticidal, and methods of modulating expression or activity of their target genes to reduce or eliminate parasites from a colony or population. In some embodiments, nucleic acid molecules are provided or disclosed that are selectively anti-parasitical or miticidal, modulating expression or activity of the *Varroa* calmodulin gene to reduce or eliminate *Varroa* parasites from a colony or population of bees without affecting calmodulin gene in non-target organisms.

In aspects according to the present disclosure, a anti-parasitic, anti-pest or insecticidal nucleic acid molecule comprises a nucleotide sequence having at least 80%, 85%, 88%, 90%, 92%, 95%, 96%, 97%, 98%, 99% or 100% sequence identity to a sequence or a portion of a sequence selected from the group consisting of SEQ ID NOs: 1 to 94. In certain aspects, the nucleic acid molecule is selected from the group consisting of ssDNA, ssRNA, dsRNA, dsDNA, or DNA/RNA hybrids. Several embodiments relate to a dsRNA comprising a nucleotide sequence having at least 80%, 85%, 88%, 90%, 92%, 95%, 96%, 97%, 98%, or 99% sequence identity to a sequence or a portion of a sequence selected from the group consisting of SEQ ID NOs: 1 to 94. Several embodiments relate to a dsRNA comprising a nucleotide sequence having at least 100% sequence identity to a sequence or a portion of a sequence selected from the group consisting of SEQ ID NOs: 1 to 94. In another aspect, a DNA encoding at least one nucleic acid, such as a ssRNA or dsRNA, comprises a nucleotide sequence or a portion of a nucleotide sequence selected from the group consisting of SEQ ID NOs: 1 to 94, or having at least 80%, 85%, 88%, 90%, 92%, 95%, 96%, 97%, 98%, or 99% sequence identity to SEQ ID NOs: 1 to 94 or a portion thereof is provided. In yet another aspect, a recombinant DNA encoding at least one nucleic acid, such as a ssRNA or dsRNA, comprises a nucleotide sequence or a portion of a nucleotide sequence selected from the group consisting of SEQ ID NOs: 1 to 94, a heterologous promoter and a transcription terminator sequence are provided. In another aspect, the present disclosure provides a recombinant DNA encoding at least one nucleic acid, such as a ssRNA or dsRNA, that comprises a nucleotide sequence having at least 80%, 85%, 88%, 90%, 92%, 95%, 96%, 97%, 98%, 99% or 100% sequence identity to a sequence or a portion of a sequence selected from the group consisting of SEQ ID NOs: 1 to 94, and further comprising a heterologous promoter and a transcription terminator.

In aspects according to the present disclosure, a composition comprises an anti-parasitic, anti-pest or insecticidal nucleic acid molecule having 100 percent sequence identity to a region of 10 to 17 or more contiguous nucleotides in the target gene or RNA transcribed from the target gene. In an aspect, a composition comprises an anti-parasitic, anti-pest or insecticidal nucleic acid molecule having 100 percent sequence identity to a region of 18 to 25, or more contiguous nucleotides in the target gene or RNA transcribed from the target gene. In an aspect, a composition comprises an anti-parasitic, anti-pest or insecticidal nucleic acid molecule having 100 percent sequence identity to a region of 20 to 30, or more contiguous nucleotides in the target gene or RNA transcribed from the target gene. In an aspect, a composition comprises an anti-parasitic, anti-pest or insecticidal nucleic acid molecule having 100 percent sequence identity to a region of 25 to 35, or more contiguous nucleotides in the target gene or RNA transcribed from the target gene. In an aspect, a composition comprises an anti-parasitic, anti-pest or insecticidal nucleic acid molecule having 100 percent sequence identity to a region of 30 to 40, or more contiguous nucleotides in the target gene or RNA transcribed from the target gene. In an aspect, a composition comprises an anti-parasitic, anti-pest or insecticidal nucleic acid molecule having 100 percent sequence identity to a region of 40 to 50, or more contiguous nucleotides in the target gene or RNA transcribed from the target gene. In an aspect, a composition comprises an anti-parasitic, anti-pest or insecticidal nucleic acid molecule having 100 percent sequence identity to a region of 50 to 60, or more contiguous nucleotides in the target gene or RNA transcribed from the target gene. In an aspect, a composition comprises an anti-parasitic, anti-pest or insecticidal nucleic acid molecule having 100 percent sequence identity to a region of 45 to 60, or more contiguous nucleotides in the target gene or RNA transcribed from the target gene. In an aspect, a composition comprises an anti-parasitic, anti-pest or insecticidal nucleic acid molecule having 100 percent sequence identity to a region up to 60 contiguous nucleotides in the target gene or RNA transcribed from the target gene. In an aspect, a composition comprises an anti-parasitic, anti-pest or insecticidal nucleic acid molecule having 100 percent sequence identity to a region up to 50 contiguous nucleotides in the target gene or RNA transcribed from the target gene. In an aspect, a composition comprises an anti-parasitic, anti-pest or insecticidal nucleic acid molecule having 100 percent sequence identity to a region up to 40 contiguous nucleotides in the target gene or RNA transcribed from the target gene. In an aspect, a composition comprises an anti-parasitic, anti-pest or insecticidal nucleic acid molecule having 100 percent sequence identity to a region of at least 25 contiguous nucleotides in the target gene or RNA transcribed from the target gene. In an aspect, a composition comprises an anti-parasitic, anti-pest or insecticidal nucleic acid molecule having 100 percent sequence identity to a region of at least 35 contiguous nucleotides in the target gene or RNA transcribed from the target gene. In an aspect, a composition comprises an anti-parasitic, anti-pest or insecticidal nucleic acid molecule having 100 percent sequence identity to a region of at least 40 contiguous nucleotides in the target gene or RNA transcribed from the target gene. In an aspect, a composition comprises an anti-parasitic, anti-pest or insecticidal nucleic acid molecule having 100 percent sequence identity to a region of at least 50 contiguous nucleotides in the target gene or RNA transcribed from the target gene. In an aspect, a composition comprises an anti-parasitic, anti-pest or insecticidal nucleic acid molecule having 100 percent sequence identity to a region of at least 60 contiguous nucleotides in the target gene or RNA transcribed from the target gene. In an aspect, a target gene may be a gene comprising SEQ ID NO: 1 to 89 or 93. In an aspect, a target gene may be a gene comprising SEQ ID NO: 1. In an aspect, a target gene may be a gene comprising SEQ ID NO: 2. In an aspect, a target gene may be a gene comprising SEQ ID NO: 3. In an aspect, a target gene may be a gene comprising SEQ ID NO: 4. In an aspect, a target gene may be a gene comprising SEQ ID NO: 69. In an aspect, a target gene may be a gene comprising SEQ ID NO: 70. In an aspect, a target gene may be a gene comprising SEQ ID NO: 88. In an aspect, a target gene may be a gene comprising SEQ ID NO: 89. In an aspect, a target gene may be a gene comprising a sequence selected from SEQ ID NOs:71-87. In an aspect, a target gene may be a gene comprising a sequence selected from SEQ ID NOs:6-68.

In aspects according to the present disclosure, a composition comprises an anti-parasitic, anti-pest or insecticidal nucleic acid molecule having 99 percent sequence identity to a region of 10 to 17 or more contiguous nucleotides in the target gene or RNA transcribed from the target gene. In an aspect, a composition comprises an anti-parasitic, anti-pest or insecticidal nucleic acid molecule having 99 percent sequence identity to a region of 18 to 25, or more contiguous nucleotides in the target gene or RNA transcribed from the target gene. In an aspect, a composition comprises an anti-parasitic, anti-pest or insecticidal nucleic acid molecule having 99 percent sequence identity to a region of 20 to 30, or more contiguous nucleotides in the target gene or RNA transcribed from the target gene. In an aspect, a composition comprises an anti-parasitic, anti-pest or insecticidal nucleic acid molecule having 99 percent sequence identity to a region of 25 to 35, or more contiguous nucleotides in the target gene or RNA transcribed from the target gene. In an aspect, a composition comprises an anti-parasitic, anti-pest or insecticidal nucleic acid molecule having 99 percent sequence identity to a region of 30 to 40, or more contiguous nucleotides in the target gene or RNA transcribed from the target gene. In an aspect, a composition comprises an anti-parasitic, anti-pest or insecticidal nucleic acid molecule having 99 percent sequence identity to a region of 40 to 50, or more contiguous nucleotides in the target gene or RNA transcribed from the target gene. In an aspect, an anti-parasitic, anti-pest or insecticidal composition comprises a nucleic acid molecule having 99 percent sequence identity to a region of 50 to 60, or more contiguous nucleotides in the target gene or RNA transcribed from the target gene. In an aspect, a composition comprises an anti-parasitic, anti-pest or insecticidal nucleic acid molecule having 99 percent sequence identity to a region of 45 to 60, or more contiguous nucleotides in the target gene or RNA transcribed from the target gene. In an aspect, a composition comprises an anti-parasitic, anti-pest or insecticidal nucleic acid molecule having 99 percent sequence identity to a region up to 60 contiguous nucleotides in the target gene or RNA transcribed from the target gene. In an aspect, a composition comprises an anti-parasitic, anti-pest or insecticidal nucleic acid molecule having 99 percent sequence identity to a region up to 50 contiguous nucleotides in the target gene or RNA transcribed from the target gene. In an aspect, a composition comprises an anti-parasitic, anti-pest or insecticidal nucleic acid molecule having 99 percent sequence identity to a region up to 40 contiguous nucleotides in the target gene or RNA transcribed from the target gene. In an aspect, a composition comprises an anti-parasitic, anti-pest or insecticidal nucleic acid molecule having 99 percent sequence identity to a region of at least 25 contiguous nucleotides in the target gene or RNA transcribed from the target gene. In an aspect, a composition comprises an anti-parasitic, anti-pest or insecticidal nucleic acid molecule having 99 percent sequence identity to a region of at least 35 contiguous nucleotides in the target gene or RNA transcribed from the target gene. In an aspect, a composition comprises an anti-parasitic, anti-pest or insecticidal nucleic acid molecule having 99 percent sequence identity to a region of at least 40 contiguous nucleotides in the target gene or RNA transcribed from the target gene. In an aspect, a composition comprises an anti-parasitic, anti-pest or insecticidal nucleic acid molecule having 99 percent sequence identity to a region of at least 50 contiguous nucleotides in the target gene or RNA transcribed from the target gene. In an aspect, a composition comprises an anti-parasitic, anti-pest or insecticidal nucleic acid molecule having 99 percent sequence identity to a region of at least 60 contiguous nucleotides in the target gene or RNA transcribed from the target gene. In some aspects, an anti-parasitic, anti-pest or insecticidal nucleic acid has at least 98 percent sequence identity to a region of the target gene. In an aspect, an anti-parasitic, anti-pest or insecticidal nucleic acid has at least 97 percent sequence identity to a region of the target gene. In some aspects, an anti-parasitic, anti-pest or insecticidal nucleic acid has at least 96 percent sequence identity to a region of the target gene. In an aspect, an anti-parasitic, anti-pest or insecticidal nucleic acid has at least 95 percent sequence identity to a region of the target gene. In some aspects, an anti-parasitic, anti-pest or insecticidal nucleic acid has at least 94 percent sequence identity to a region of the target gene.

In an aspect, an anti-parasitic, anti-pest or insecticidal nucleic acid has at least 93 percent sequence identity to a region of the target gene. In some aspects, an anti-parasitic, anti-pest or insecticidal nucleic acid has at least 92 percent sequence identity to a region of the target gene. In an aspect, an anti-parasitic, anti-pest or insecticidal nucleic acid has at least 91 percent sequence identity to a region of the target gene. In an aspect, an anti-parasitic, anti-pest or insecticidal nucleic acid has at least about 83, 84, 85, 86, 87, 88, 89, 90 percent identity to a region of the target gene as provided above. In an aspect, a target gene may be a gene comprising SEQ ID NO: 1 to 89 or 93. In an aspect, a target gene may be a gene comprising SEQ ID NO: 1. In an aspect, a target gene may be a gene comprising SEQ ID NO: 2. In an aspect, a target gene may be a gene comprising SEQ ID NO: 3. In an aspect, a target gene may be a gene comprising SEQ ID NO: 4. In an aspect, a target gene may be a gene comprising SEQ ID NO: 69. In an aspect, a target gene may be a gene comprising SEQ ID NO: 70. In an aspect, a target gene may be a gene comprising SEQ ID NO: 88. In an aspect, a target gene may be a gene comprising SEQ ID NO: 89. In an aspect, a target gene may be a gene comprising sequence selected from SEQ ID NOs:71-87. In an aspect, a target gene may be a gene comprising a sequence selected from SEQ ID NOs:6-68.

In aspects according to the present disclosure, a composition comprises an anti-parasitic, anti-pest or insecticidal nucleic acid molecule having 100 percent sequence identity to a region of 10 to 17 or more contiguous nucleotides in to one allele or one family member of a given target gene (coding or non-coding sequence of a gene). In an aspect, a composition comprises an anti-parasitic, anti-pest or insecticidal nucleic acid molecule having 100 percent sequence identity to a region of 18 to 25, or more contiguous nucleotides to one allele or one family member of a given target gene). In an aspect, a composition comprises an anti-parasitic, anti-pest or insecticidal nucleic acid molecule having 100 percent sequence identity to a region of 20 to 30, or more contiguous nucleotides to one allele or one family member of a given target gene. In an aspect, a composition comprises an anti-parasitic, anti-pest or insecticidal nucleic acid molecule having 100 percent sequence identity to a region of 25 to 35, or more contiguous nucleotides to one allele or one family member of a given target gene. In an aspect, a composition comprises an anti-parasitic, anti-pest or insecticidal nucleic acid molecule having 100 percent sequence identity to a region of 30 to 40, or more contiguous nucleotides to one allele or one family member of a given target gene. In an aspect, a composition comprises an anti-parasitic, anti-pest or insecticidal nucleic acid molecule having 100 percent sequence identity to a region of 40 to 50, or more contiguous nucleotides to one allele or one family member of a given target gene. In an aspect, a composition comprises an anti-parasitic, anti-pest or insecticidal nucleic acid molecule having 100 percent sequence identity to a region of 50 to 60, or more contiguous nucleotides to one allele or one family member of a given target gene. In an aspect, a composition comprises an anti-parasitic, anti-pest or insecticidal nucleic acid molecule having 100 percent sequence identity to a region of 45 to 60, or more contiguous nucleotides to one allele or one family member of a given target gene. In an aspect, a composition comprises an anti-parasitic, anti-pest or insecticidal nucleic acid molecule having 100 percent sequence identity to a region up to 60 contiguous nucleotides to one allele or one family member of a given target gene. In an aspect, a composition comprises an anti-parasitic, anti-pest or insecticidal nucleic acid molecule having 100 percent sequence identity to a region up to 50 contiguous nucleotides to one allele or one family member of a given target gene. In an aspect, a composition comprises an anti-parasitic, anti-pest or insecticidal nucleic acid molecule having 100 percent sequence identity to a region up to 40 contiguous nucleotides to one allele or one family member of a given target gene. In an aspect, a composition comprises an anti-parasitic, anti-pest or insecticidal nucleic acid molecule having 100 percent sequence identity to a region of at least 25 contiguous nucleotides to one allele or one family member of a given target gene. In an aspect, a composition comprises an anti-parasitic, anti-pest or insecticidal nucleic acid molecule having 100 percent sequence identity to a region of at least 35 contiguous nucleotides to one allele or one family member of a given target gene. In an aspect, a composition comprises an anti-parasitic, anti-pest or insecticidal nucleic acid molecule having 100 percent sequence identity to a region of at least 40 contiguous nucleotides to one allele or one family member of a given target gene. In an aspect, a composition comprises an anti-parasitic, anti-pest or insecticidal nucleic acid molecule having 100 percent sequence identity to a region of at least 50 contiguous nucleotides to one allele or one family member of a given target gene. In an aspect, a composition comprises an anti-parasitic, anti-pest or insecticidal nucleic acid molecule having 100 percent sequence identity to a region of at least 60 contiguous nucleotides to one allele or one family member of a given target gene. In an aspect, a target gene may be a gene comprising SEQ ID NO: 1 to 89. In an aspect, a target gene may be a gene comprising SEQ ID NO: 1. In an aspect, a target gene may be a gene comprising SEQ ID NO: 2. In an aspect, a target gene may be a gene comprising SEQ ID NO: 3. In an aspect, a target gene may be a gene comprising SEQ ID NO: 4. In an aspect, a target gene may be a gene comprising SEQ ID NO: 69. In an aspect, a target gene may be a gene comprising SEQ ID NO: 70. In an aspect, a target gene may be a gene comprising SEQ ID NO: 88. In an aspect, a target gene may be a gene comprising SEQ ID NO: 89. In an aspect, a target gene may be a gene comprising a sequence selected from SEQ ID NOs:71-87. In an aspect, a target gene may be a gene comprising a sequence selected from SEQ ID NOs:6-68. In an aspect, a target gene may be a gene comprising SEQ ID NO: 93.

In aspects according to the present disclosure, a composition comprises an anti-parasitic, anti-pest or insecticidal nucleic acid molecule having 99 percent sequence identity to a region of 10 to 17 or more contiguous nucleotides to one allele or one family member of a given target gene. In an aspect, a composition comprises an anti-parasitic, anti-pest or insecticidal nucleic acid molecule having 99 percent sequence identity to a region of 18 to 25, or more contiguous nucleotides to one allele or one family member of a given target gene. In an aspect, a composition comprises an anti-parasitic, anti-pest or insecticidal nucleic acid molecule having 99 percent sequence identity to a region of 20 to 30, or more contiguous nucleotides to one allele or one family member of a given target gene. In an aspect, a composition comprises an anti-parasitic, anti-pest or insecticidal nucleic acid molecule having 99 percent sequence identity to a region of 25 to 35, or more contiguous nucleotides to one allele or one family member of a given target gene. In an aspect, a composition comprises an anti-parasitic, anti-pest or insecticidal nucleic acid molecule having 99 percent sequence identity to a region of 30 to 40, or more contiguous nucleotides to one allele or one family member of a given target gene. In an aspect, a composition comprises an anti-parasitic, anti-pest or insecticidal nucleic acid molecule having 99 percent sequence identity to a region of 40 to 50, or more contiguous nucleotides to one allele or one family member of a given target gene. In an aspect, a composition comprises an anti-parasitic, anti-pest or insecticidal nucleic acid molecule having 99 percent sequence identity to a region of 50 to 60, or more contiguous nucleotides to one allele or one family member of a given target gene. In an aspect, a composition comprises an anti-parasitic, anti-pest or insecticidal nucleic acid molecule having 99 percent sequence identity to a region of 45 to 60, or more contiguous nucleotides to one allele or one family member of a given target gene. In an aspect, a composition comprises an anti-parasitic, anti-pest or insecticidal nucleic acid molecule having 99 percent sequence identity to a region up to 60 contiguous nucleotides to one allele or one family member of a given target gene. In an aspect, a composition comprises an anti-parasitic, anti-pest or insecticidal nucleic acid molecule having 99 percent sequence identity to a region up to 50 contiguous nucleotides to one allele or one family member of a given target gene. In an aspect, a composition comprises an anti-parasitic, anti-pest or insecticidal nucleic acid molecule having 99 percent sequence identity to a region up to 40 contiguous nucleotides to one allele or one family member of a given target gene. In an aspect, a composition comprises an anti-parasitic, anti-pest or insecticidal nucleic acid molecule having 99 percent sequence identity to a region of at least 25 contiguous nucleotides to one allele or one family member of a given target gene. In an aspect, a composition comprises an anti-parasitic, anti-pest or insecticidal nucleic acid molecule having 99 percent sequence identity to a region of at least 35 contiguous nucleotides to one allele or one family member of a given target gene. In an aspect, a composition comprises an anti-parasitic, anti-pest or insecticidal nucleic acid molecule having 99 percent sequence identity to a region of at least 40 contiguous nucleotides to one allele or one family member of a given target gene. In an aspect, a composition comprises an anti-parasitic, anti-pest or insecticidal nucleic acid molecule having 99 percent sequence identity to a region of at least 50 contiguous nucleotides to one allele or one family member of a given target gene. In an aspect, a composition comprises an anti-parasitic, anti-pest or insecticidal nucleic acid molecule having 99 percent sequence identity to a region of at least 60 contiguous nucleotides to one allele or one family member of a given target gene. In some aspects, an anti-parasitic, anti-pest or insecticidal nucleic acid has at least 98 percent sequence identity to a region of the target gene. In an aspect, an anti-parasitic, anti-pest or insecticidal nucleic acid has at least 97 percent sequence identity to a region of the target gene. In some aspects, an anti-parasitic, anti-pest or insecticidal nucleic acid has at least 96 percent sequence identity to a region of the target gene. In an aspect, an anti-parasitic, anti-pest or insecticidal nucleic acid has at least 95 percent sequence identity to a region of the target gene. In some aspects, an anti-parasitic, anti-pest or insecticidal nucleic acid has at least 94 percent sequence identity to a region of the target gene. In an aspect, an anti-parasitic, anti-pest or insecticidal nucleic acid has at least 93 percent sequence identity to a region of the target gene. In some aspects, an anti-parasitic, anti-pest or insecticidal nucleic acid has at least 92 percent sequence identity to a region of the target gene. In an aspect, an anti-parasitic, anti-pest or insecticidal nucleic acid has at least 91 percent sequence identity to a region of the target gene. In an aspect, an anti-parasitic, anti-pest or insecticidal nucleic acid has at least about 83, 84, 85, 86, 87, 88, 89, 90 percent identity to a region of the target gene as provided above. In an aspect, a target gene may be a gene comprising SEQ ID NO: 1 to 89. In an aspect, a target gene may be a gene comprising SEQ ID NO: 1. In an aspect, a target gene may be a gene comprising SEQ ID NO: 2. In an aspect, a target gene may be a gene comprising SEQ ID NO: 3. In an aspect, a target gene may be a gene comprising SEQ ID NO: 4. In an aspect, a target gene may be a gene comprising SEQ ID NO: 69. In an aspect, a target gene may be a gene comprising SEQ ID NO: 70. In an aspect, a target gene may be a gene comprising SEQ ID NO: 88. In an aspect, a target gene may be a gene comprising SEQ ID NO: 89. In an aspect, a target gene may be a gene comprising a sequence selected from SEQ ID NOs:71-87. In an aspect, a target gene may be a gene comprising a sequence selected from SEQ ID NOs:6-68. In an aspect, a target gene may be a gene comprising SEQ ID NO: 93.

In aspects according to the present disclosure, a composition comprises an anti-parasitic, anti-pest or insecticidal nucleic acid molecule having 100 percent sequence identity to a region of 10 to 17 or more contiguous nucleotides of identity with or complementarity to multiple alleles or family members of a given target gene. In an aspect, a composition comprises an anti-parasitic, anti-pest or insecticidal nucleic acid molecule having 100 percent sequence identity to a region of 18 to 25, or more contiguous nucleotides to one allele or one family member of a given target gene. In an aspect, a composition comprises an anti-parasitic, anti-pest or insecticidal nucleic acid molecule having 100 percent sequence identity to a region of 20 to 30, or more contiguous nucleotides of identity with or complementarity to multiple alleles or family members of a given target gene. In an aspect, a composition comprises an anti-parasitic, anti-pest or insecticidal nucleic acid molecule having 100 percent sequence identity to a region of 25 to 35, or more contiguous nucleotides of identity with or complementarity to multiple alleles or family members of a given target gene. In an aspect, a composition comprises an anti-parasitic, anti-pest or insecticidal nucleic acid molecule having 100 percent sequence identity to a region of 30 to 40, or more contiguous nucleotides of identity with or complementarity to multiple alleles or family members of a given target gene. In an aspect, a composition comprises an anti-parasitic, anti-pest or insecticidal nucleic acid molecule having 100 percent sequence identity to a region of 40 to 50, or more contiguous nucleotides of identity with or complementarity to multiple alleles or family members of a given target gene. In an aspect, a composition comprises an anti-parasitic, anti-pest or insecticidal nucleic acid molecule having 100 percent sequence identity to a region of 50 to 60, or more contiguous nucleotides of identity with or complementarity to multiple alleles or family members of a given target gene. In an aspect, a composition comprises an anti-parasitic, anti-pest or insecticidal nucleic acid molecule having 100 percent sequence identity to a region of 45 to 60, or more contiguous nucleotides of identity with or complementarity to multiple alleles or family members of a given target gene. In an aspect, a composition comprises an anti-parasitic, anti-pest or insecticidal nucleic acid molecule having 100 percent sequence identity to a region up to 60 contiguous nucleotides of identity with or complementarity to multiple alleles or family members of a given target gene. In an aspect, a composition comprises an anti-parasitic, anti-pest or insecticidal nucleic acid molecule having 100 percent sequence identity to a region up to 50 contiguous nucleotides of identity with or complementarity to multiple alleles or family members of a given target gene. In an aspect, a composition comprises an anti-parasitic, anti-pest or insecticidal nucleic acid molecule having 100 percent sequence identity to a region up to 40 contiguous nucleotides of identity with or complementarity to multiple alleles or family members of a given target gene. In an aspect, a composition comprises an anti-parasitic, anti-pest or insecticidal nucleic acid molecule having 100 percent sequence identity to a region of at least 25 contiguous nucleotides of identity with or complementarity to multiple alleles or family members of a given target gene. In an aspect, a composition comprises an anti-parasitic, anti-pest or insecticidal nucleic acid molecule having 100 percent sequence identity to a region of at least 35 contiguous nucleotides of identity with or complementarity to multiple alleles or family members of a given target gene. In an aspect, a composition comprises an anti-parasitic, anti-pest or insecticidal nucleic acid molecule having 100 percent sequence identity to a region of at least 40 contiguous nucleotides of identity with or complementarity to multiple alleles or family members of a given target gene. In an aspect, a composition comprises an anti-parasitic, anti-pest or insecticidal nucleic acid molecule having 100 percent sequence identity to a region of at least 50 contiguous nucleotides of identity with or complementarity to multiple alleles or family members of a given target gene. In an aspect, a composition comprises an anti-parasitic, anti-pest or insecticidal nucleic acid molecule having 100 percent sequence identity to a region of at least 60 contiguous nucleotides of identity with or complementarity to multiple alleles or family members of a given target gene. In an aspect, a target gene may be a gene comprising SEQ ID NO: 1 to 89. In an aspect, a target gene may be a gene comprising SEQ ID NO: 1. In an aspect, a target gene may be a gene comprising SEQ ID NO: 2. In an aspect, a target gene may be a gene comprising SEQ ID NO: 3. In an aspect, a target gene may be a gene comprising SEQ ID NO: 4. In an aspect, a target gene may be a gene comprising SEQ ID NO: 69. In an aspect, a target gene may be a gene comprising SEQ ID NO: 70. In an aspect, a target gene may be a gene comprising SEQ ID NO: 88. In an aspect, a target gene may be a gene comprising SEQ ID NO: 89. In an aspect, a target gene may be a gene comprising a sequence selected from SEQ ID NOs:71-87. In an aspect, a target gene may be a gene comprising a sequence selected from SEQ ID NOs:6-68. In an aspect, a target gene may be a gene comprising SEQ ID NO: 93.

In aspects according to the present disclosure, a composition comprises an anti-parasitic, anti-pest or insecticidal nucleic acid molecule having 99 percent sequence identity to a region of 10 to 17 or more contiguous nucleotides of identity with or complementarity to multiple alleles or family members of a given target gene. In an aspect, a composition comprises an anti-parasitic, anti-pest or insecticidal nucleic acid molecule having 99 percent sequence identity to a region of 18 to 25, or more contiguous nucleotides of identity with or complementarity to multiple alleles or family members of a given target gene. In an aspect, a composition comprises an anti-parasitic, anti-pest or insecticidal nucleic acid molecule having 99 percent sequence identity to a region of 20 to 30, or more contiguous nucleotides of identity with or complementarity to multiple alleles or family members of a given target gene. In an aspect, a composition comprises an anti-parasitic, anti-pest or insecticidal nucleic acid molecule having 99 percent sequence identity to a region of 25 to 35, or more contiguous nucleotides of identity with or complementarity to multiple alleles or family members of a given target gene. In an aspect, a composition comprises an anti-parasitic, anti-pest or insecticidal nucleic acid molecule having 99 percent sequence identity to a region of 30 to 40, or more contiguous nucleotides of identity with or complementarity to multiple alleles or family members of a given target gene. In an aspect, a composition comprises an anti-parasitic, anti-pest or insecticidal nucleic acid molecule having 99 percent sequence identity to a region of 40 to 50, or more contiguous nucleotides of identity with or complementarity to multiple alleles or family members of a given target gene. In an aspect, a composition comprises an anti-parasitic, anti-pest or insecticidal nucleic acid molecule having 99 percent sequence identity to a region of 50 to 60, or more contiguous nucleotides of identity with or complementarity to multiple alleles or family members of a given target gene. In an aspect, a composition comprises an anti-parasitic, anti-pest or insecticidal nucleic acid molecule having 99 percent sequence identity to a region of 45 to 60, or more contiguous nucleotides of identity with or complementarity to multiple alleles or family members of a given target gene. In an aspect, a composition comprises an anti-parasitic, anti-pest or insecticidal nucleic acid molecule having 99 percent sequence identity to a region up to 60 contiguous nucleotides of identity with or complementarity to multiple alleles or family members of a given target gene. In an aspect, a composition comprises an anti-parasitic, anti-pest or insecticidal nucleic acid molecule having 99 percent sequence identity to a region up to 50 contiguous nucleotides of identity with or complementarity to multiple alleles or family members of a given target gene. In an aspect, a composition comprises an anti-parasitic, anti-pest or insecticidal nucleic acid molecule having 99 percent sequence identity to a region up to 40 contiguous nucleotides of identity with or complementarity to multiple alleles or family members of a given target gene. In an aspect, a composition comprises an anti-parasitic, anti-pest or insecticidal nucleic acid molecule having 99 percent sequence identity to a region of at least 25 contiguous nucleotides of identity with or complementarity to multiple alleles or family members of a given target gene. In an aspect, a composition comprises an anti-parasitic, anti-pest or insecticidal nucleic acid molecule having 99 percent sequence identity to a region of at least 35 contiguous nucleotides of identity with or complementarity to multiple alleles or family members of a given target gene. In an aspect, a composition comprises an anti-parasitic, anti-pest or insecticidal nucleic acid molecule having 99 percent sequence identity to a region of at least 40 contiguous nucleotides of identity with or complementarity to multiple alleles or family members of a given target gene. In an aspect, a composition comprises an anti-parasitic, anti-pest or insecticidal nucleic acid molecule having 99 percent sequence identity to a region of at least 50 contiguous nucleotides of identity with or complementarity to multiple alleles or family members of a given target gene. In an aspect, a composition comprises an anti-parasitic, anti-pest or insecticidal nucleic acid molecule having 99 percent sequence identity to a region of at least 60 contiguous nucleotides of identity with or complementarity to multiple alleles or family members of a given target gene. In some aspects, an anti-parasitic, anti-pest or insecticidal nucleic acid has at least 98 percent sequence identity to a region of a target gene. In an aspect, an anti-parasitic, anti-pest or insecticidal nucleic acid has at least 97 percent sequence identity to a region of a target gene. In some aspects, an anti-parasitic, anti-pest or insecticidal nucleic acid has at least 96 percent sequence identity to a region of a target gene. In an aspect, an anti-parasitic, anti-pest or insecticidal nucleic acid has at least 95 percent sequence identity to a region of a target gene. In some aspects, an anti-parasitic, anti-pest or insecticidal nucleic acid has at least 94 percent sequence identity to a region of a target gene. In an aspect, an anti-parasitic, anti-pest or insecticidal nucleic acid has at least 93 percent sequence identity to a region of a target gene. In some aspects, an anti-parasitic, anti-pest or insecticidal nucleic acid has at least 92 percent sequence identity to a region of a target gene. In an aspect, an anti-parasitic, anti-pest or insecticidal nucleic acid has at least 91 percent sequence identity to a region of a target gene. In an aspect, an anti-parasitic, anti-pest or insecticidal nucleic acid has at least about 83, 84, 85, 86, 87, 88, 89, 90 percent identity to a region of a target gene as provided above. In an aspect, a target gene may be a gene comprising SEQ ID NO: 1 to 89. In an aspect, a target gene may be a gene comprising SEQ ID NO: 1. In an aspect, a target gene may be a gene comprising SEQ ID NO: 2. In an aspect, a target gene may be a gene comprising SEQ ID NO: 3. In an aspect, a target gene may be a gene comprising SEQ ID NO: 4. In an aspect, a target gene may be a gene comprising SEQ ID NO: 69. In an aspect, a target gene may be a gene comprising SEQ ID NO: 70. In an aspect, a target gene may be a gene comprising SEQ ID NO: 88. In an aspect, a target gene may be a gene comprising SEQ ID NO: 89. In an aspect, a target gene may be a gene comprising a sequence selected from SEQ ID NOs:71-87. In an aspect, a target gene may be a gene comprising a sequence selected from SEQ ID NOs:6-68. In an aspect, a target gene may be a gene comprising SEQ ID NO: 93.

In aspects according to the present disclosure, a composition comprises an anti-parasitic, anti-pest or insecticidal nucleic acid molecule having 100 percent sequence identity to a region of 10 to 17 or more contiguous nucleotides in the target gene or RNA transcribed from the target gene, wherein the anti-parasitic, anti-pest or insecticidal nucleic acid molecule does not comprise a sequence that is 100% identical or complementary to 5, 6, 7, 8, 9, 10, 11, 12, 13, 14, 15, 16, 17, 18, 19, 20, 21, 22, 23, 24, 25 or more contiguous nucleotides of gene sequence of a non-target organism. In an aspect, a composition comprises an anti-parasitic, anti-pest or insecticidal nucleic acid molecule having 100 percent sequence identity to a region of 18 to 25, or more contiguous nucleotides in the target gene or RNA transcribed from the target gene, wherein the anti-parasitic, anti-pest or insecticidal nucleic acid molecule does not comprise a sequence that is 100% identical or complementary to 5, 6, 7, 8, 9, 10, 11, 12, 13, 14, 15, 16, 17, 18, 19, 20, 21, 22, 23, 24, 25 or more contiguous nucleotides of gene sequence of a non-target organism. In an aspect, a composition comprises an anti-parasitic, anti-pest or insecticidal nucleic acid molecule having 100 percent sequence identity to a region of 20 to 30, or more contiguous nucleotides in the target gene or RNA transcribed from the target gene, wherein the anti-parasitic, anti-pest or insecticidal nucleic acid molecule does not comprise a sequence that is 100% identical or complementary to 5, 6, 7, 8, 9, 10, 11, 12, 13, 14, 15, 16, 17, 18, 19, 20, 21, 22, 23, 24, 25 or more contiguous nucleotides of gene sequence of a non-target organism. In an aspect, a composition comprises an anti-parasitic, anti-pest or insecticidal nucleic acid molecule having 100 percent sequence identity to a region of 25 to 35, or more contiguous nucleotides in the target gene or RNA transcribed from the target gene, wherein the anti-parasitic, anti-pest or insecticidal nucleic acid molecule does not comprise a sequence that is 100% identical or complementary to 5, 6, 7, 8, 9, 10, 11, 12, 13, 14, 15, 16, 17, 18, 19, 20, 21, 22, 23, 24, 25 or more contiguous nucleotides of gene sequence of a non-target organism. In an aspect, a composition comprises an anti-parasitic, anti-pest or insecticidal nucleic acid molecule having 100 percent sequence identity to a region of 30 to 40, or more contiguous nucleotides in the target gene or RNA transcribed from the target gene, wherein the anti-parasitic, anti-pest or insecticidal nucleic acid molecule does not comprise a sequence that is 100% identical or complementary to 5, 6, 7, 8, 9, 10, 11, 12, 13, 14, 15, 16, 17, 18, 19, 20, 21, 22, 23, 24, 25 or more contiguous nucleotides of gene sequence of a non-target organism. In an aspect, a composition comprises an anti-parasitic, anti-pest or insecticidal nucleic acid molecule having 100 percent sequence identity to a region of 40 to 50, or more contiguous nucleotides in the target gene or RNA transcribed from the target gene, wherein the anti-parasitic, anti-pest or insecticidal nucleic acid molecule does not comprise a sequence that is 100% identical or complementary to 5, 6, 7, 8, 9, 10, 11, 12, 13, 14, 15, 16, 17, 18, 19, 20, 21, 22, 23, 24, 25 or more contiguous nucleotides of gene sequence of a non-target organism. In an aspect, a composition comprises an anti-parasitic, anti-pest or insecticidal nucleic acid molecule having 100 percent sequence identity to a region of 50 to 60, or more contiguous nucleotides in the target gene or RNA transcribed from the target gene, wherein the anti-parasitic, anti-pest or insecticidal nucleic acid molecule does not comprise a sequence that is 100% identical or complementary to 5, 6, 7, 8, 9, 10, 11, 12, 13, 14, 15, 16, 17, 18, 19, 20, 21, 22, 23, 24, 25 or more contiguous nucleotides of gene sequence of a non-target organism. In an aspect, a composition comprises an anti-parasitic, anti-pest or insecticidal nucleic acid molecule having 100 percent sequence identity to a region of 45 to 60, or more contiguous nucleotides in the target gene or RNA transcribed from the target gene, wherein the anti-parasitic, anti-pest or insecticidal nucleic acid molecule does not comprise a sequence that is 100% identical or complementary to 5, 6, 7, 8, 9, 10, 11, 12, 13, 14, 15, 16, 17, 18, 19, 20, 21, 22, 23, 24, 25 or more contiguous nucleotides of gene sequence of a non-target organism. In an aspect, a composition comprises an anti-parasitic, anti-pest or insecticidal nucleic acid molecule having 100 percent sequence identity to a region up to 60 contiguous nucleotides in the target gene or RNA transcribed from the target gene, wherein the anti-parasitic, anti-pest or insecticidal nucleic acid molecule does not comprise a sequence that is 100% identical or complementary to 5, 6, 7, 8, 9, 10, 11, 12, 13, 14, 15, 16, 17, 18, 19, 20, 21, 22, 23, 24, 25 or more contiguous nucleotides of gene sequence of a non-target organism. In an aspect, a composition comprises an anti-parasitic, anti-pest or insecticidal nucleic acid molecule having 100 percent sequence identity to a region up to 50 contiguous nucleotides in the target gene or RNA transcribed from the target gene, wherein the anti-parasitic, anti-pest or insecticidal nucleic acid molecule does not comprise a sequence that is 100% identical or complementary to 5, 6, 7, 8, 9, 10, 11, 12, 13, 14, 15, 16, 17, 18, 19, 20, 21, 22, 23, 24, 25 or more contiguous nucleotides of gene sequence of a non-target organism. In an aspect, a composition comprises an anti-parasitic, anti-pest or insecticidal nucleic acid molecule having 100 percent sequence identity to a region up to 40 contiguous nucleotides in the target gene or RNA transcribed from the target gene, wherein the anti-parasitic, anti-pest or insecticidal nucleic acid molecule does not comprise a sequence that is 100% identical or complementary to 5, 6, 7, 8, 9, 10, 11, 12, 13, 14, 15, 16, 17, 18, 19, 20, 21, 22, 23, 24, 25 or more contiguous nucleotides of gene sequence of a non-target organism. In an aspect, a composition comprises an anti-parasitic, anti-pest or insecticidal nucleic acid molecule having 100 percent sequence identity to a region of at least 25 contiguous nucleotides in the target gene or RNA transcribed from the target gene, wherein the anti-parasitic, anti-pest or insecticidal nucleic acid molecule does not comprise a sequence that is 100% identical or complementary to 5, 6, 7, 8, 9, 10, 11, 12, 13, 14, 15, 16, 17, 18, 19, 20, 21, 22, 23, 24, 25 or more contiguous nucleotides of gene sequence of a non-target organism. In an aspect, a composition comprises an anti-parasitic, anti-pest or insecticidal nucleic acid molecule having 100 percent sequence identity to a region of at least 35 contiguous nucleotides in the target gene or RNA transcribed from the target gene, wherein the anti-parasitic, anti-pest or insecticidal nucleic acid molecule does not comprise a sequence that is 100% identical or complementary to 5, 6, 7, 8, 9, 10, 11, 12, 13, 14, 15, 16, 17, 18, 19, 20, 21, 22, 23, 24, 25 or more contiguous nucleotides of gene sequence of a non-target organism. In an aspect, a composition comprises an anti-parasitic, anti-pest or insecticidal nucleic acid molecule having 100 percent sequence identity to a region of at least 40 contiguous nucleotides in the target gene or RNA transcribed from the target gene, wherein the anti-parasitic, anti-pest or insecticidal nucleic acid molecule does not comprise a sequence that is 100% identical or complementary to 5, 6, 7, 8, 9, 10, 11, 12, 13, 14, 15, 16, 17, 18, 19, 20, 21, 22, 23, 24, 25 or more contiguous nucleotides of gene sequence of a non-target organism. In an aspect, a composition comprises an anti-parasitic, anti-pest or insecticidal nucleic acid molecule having 100 percent sequence identity to a region of at least 50 contiguous nucleotides in the target gene or RNA transcribed from the target gene, wherein the anti-parasitic, anti-pest or insecticidal nucleic acid molecule does not comprise a sequence that is 100% identical or complementary to 5, 6, 7, 8, 9, 10, 11, 12, 13, 14, 15, 16, 17, 18, 19, 20, 21, 22, 23, 24, 25 or more contiguous nucleotides of gene sequence of a non-target organism. In an aspect, a composition comprises an anti-parasitic, anti-pest or insecticidal nucleic acid molecule having 100 percent sequence identity to a region of at least 60 contiguous nucleotides in the target gene or RNA transcribed from the target gene, wherein the anti-parasitic, anti-pest or insecticidal nucleic acid molecule does not comprise a sequence that is 100% identical or complementary to 5, 6, 7, 8, 9, 10, 11, 12, 13, 14, 15, 16, 17, 18, 19, 20, 21, 22, 23, 24, 25 or more contiguous nucleotides of gene sequence of a non-target organism. In an aspect, a target gene may be a gene comprising SEQ ID NO: 1 to 89 or 93. In an aspect, a target gene may be a gene comprising SEQ ID NO: 1. In an aspect, a target gene may be a gene comprising SEQ ID NO: 2. In an aspect, a target gene may be a gene comprising SEQ ID NO: 3. In an aspect, a target gene may be a gene comprising SEQ ID NO: 4. In an aspect, a target gene may be a gene comprising SEQ ID NO: 69. In an aspect, a target gene may be a gene comprising SEQ ID NO: 70. In an aspect, a target gene may be a gene comprising SEQ ID NO: 88. In an aspect, a target gene may be a gene comprising SEQ ID NO: 89. In an aspect, a target gene may be a gene comprising a sequence selected from SEQ ID NOs:71-87. In an aspect, a target gene may be a gene comprising a sequence selected from SEQ ID NOs:6-68.

In aspects according to the present disclosure, a composition comprises an anti-parasitic, anti-pest or insecticidal nucleic acid molecule having 99 percent sequence identity to a region of 10 to 17 or more contiguous nucleotides in the target gene or RNA transcribed from the target gene, wherein the anti-parasitic, anti-pest or insecticidal nucleic acid molecule does not comprise a sequence that is 100% identical or complementary to 5, 6, 7, 8, 9, 10, 11, 12, 13, 14, 15, 16, 17, 18, 19, 20, 21, 22, 23, 24, 25 or more contiguous nucleotides of gene sequence of a non-target organism. In an aspect, a composition comprises an anti-parasitic, anti-pest or insecticidal nucleic acid molecule having 99 percent sequence identity to a region of 18 to 25, or more contiguous nucleotides in the target gene or RNA transcribed from the target gene, wherein the anti-parasitic, anti-pest or insecticidal nucleic acid molecule does not comprise a sequence that is 100% identical or complementary to 5, 6, 7, 8, 9, 10, 11, 12, 13, 14, 15, 16, 17, 18, 19, 20, 21, 22, 23, 24, 25 or more contiguous nucleotides of gene sequence of a non-target organism. In an aspect, a composition comprises an anti-parasitic, anti-pest or insecticidal nucleic acid molecule having 99 percent sequence identity to a region of 20 to 30, or more contiguous nucleotides in the target gene or RNA transcribed from the target gene, wherein the anti-parasitic, anti-pest or insecticidal nucleic acid molecule does not comprise a sequence that is 100% identical or complementary to 5, 6, 7, 8, 9, 10, 11, 12, 13, 14, 15, 16, 17, 18, 19, 20, 21, 22, 23, 24, 25 or more contiguous nucleotides of gene sequence of a non-target organism. In an aspect, a composition comprises an anti-parasitic, anti-pest or insecticidal nucleic acid molecule having 99 percent sequence identity to a region of 25 to 35, or more contiguous nucleotides in the target gene or RNA transcribed from the target gene, wherein the anti-parasitic, anti-pest or insecticidal nucleic acid molecule does not comprise a sequence that is 100% identical or complementary to 5, 6, 7, 8, 9, 10, 11, 12, 13, 14, 15, 16, 17, 18, 19, 20, 21, 22, 23, 24, 25 or more contiguous nucleotides of gene sequence of a non-target organism. In an aspect, a composition comprises an anti-parasitic, anti-pest or insecticidal nucleic acid molecule having 99 percent sequence identity to a region of 30 to 40, or more contiguous nucleotides in the target gene or RNA transcribed from the target gene, wherein the anti-parasitic, anti-pest or insecticidal nucleic acid molecule does not comprise a sequence that is 100% identical or complementary to 5, 6, 7, 8, 9, 10, 11, 12, 13, 14, 15, 16, 17, 18, 19, 20, 21, 22, 23, 24, 25 or more contiguous nucleotides of gene sequence of a non-target organism. In an aspect, a composition comprises an anti-parasitic, anti-pest or insecticidal nucleic acid molecule having 99 percent sequence identity to a region of 40 to 50, or more contiguous nucleotides in the target gene or RNA transcribed from the target gene, wherein the anti-parasitic, anti-pest or insecticidal nucleic acid molecule does not comprise a sequence that is 100% identical or complementary to 5, 6, 7, 8, 9, 10, 11, 12, 13, 14, 15, 16, 17, 18, 19, 20, 21, 22, 23, 24, 25 or more contiguous nucleotides of gene sequence of a non-target organism. In an aspect, an anti-parasitic, anti-pest or insecticidal composition comprises a nucleic acid molecule having 99 percent sequence identity to a region of 50 to 60, or more contiguous nucleotides in the target gene or RNA transcribed from the target gene, wherein the anti-parasitic, anti-pest or insecticidal nucleic acid molecule does not comprise a sequence that is 100% identical or complementary to 5, 6, 7, 8, 9, 10, 11, 12, 13, 14, 15, 16, 17, 18, 19, 20, 21, 22, 23, 24, 25 or more contiguous nucleotides of gene sequence of a non-target organism. In an aspect, a composition comprises an anti-parasitic, anti-pest or insecticidal nucleic acid molecule having 99 percent sequence identity to a region of 45 to 60, or more contiguous nucleotides in the target gene or RNA transcribed from the target gene, wherein the anti-parasitic, anti-pest or insecticidal nucleic acid molecule does not comprise a sequence that is 100% identical or complementary to 5, 6, 7, 8, 9, 10, 11, 12, 13, 14, 15, 16, 17, 18, 19, 20, 21, 22, 23, 24, 25 or more contiguous nucleotides of gene sequence of a non-target organism. In an aspect, a composition comprises an anti-parasitic, anti-pest or insecticidal nucleic acid molecule having 99 percent sequence identity to a region up to 60 contiguous nucleotides in the target gene or RNA transcribed from the target gene, wherein the anti-parasitic, anti-pest or insecticidal nucleic acid molecule does not comprise a sequence that is 100% identical or complementary to 5, 6, 7, 8, 9, 10, 11, 12, 13, 14, 15, 16, 17, 18, 19, 20, 21, 22, 23, 24, 25 or more contiguous nucleotides of gene sequence of a non-target organism. In an aspect, a composition comprises an anti-parasitic, anti-pest or insecticidal nucleic acid molecule having 99 percent sequence identity to a region up to 50 contiguous nucleotides in the target gene or RNA transcribed from the target gene, wherein the anti-parasitic, anti-pest or insecticidal nucleic acid molecule does not comprise a sequence that is 100% identical or complementary to 5, 6, 7, 8, 9, 10, 11, 12, 13, 14, 15, 16, 17, 18, 19, 20, 21, 22, 23, 24, 25 or more contiguous nucleotides of gene sequence of a non-target organism. In an aspect, a composition comprises an anti-parasitic, anti-pest or insecticidal nucleic acid molecule having 99 percent sequence identity to a region up to 40 contiguous nucleotides in the target gene or RNA transcribed from the target gene, wherein the anti-parasitic, anti-pest or insecticidal nucleic acid molecule does not comprise a sequence that is 100% identical or complementary to 5, 6, 7, 8, 9, 10, 11, 12, 13, 14, 15, 16, 17, 18, 19, 20, 21, 22, 23, 24, 25 or more contiguous nucleotides of gene sequence of a non-target organism. In an aspect, a composition comprises an anti-parasitic, anti-pest or insecticidal nucleic acid molecule having 99 percent sequence identity to a region of at least 25 contiguous nucleotides in the target gene or RNA transcribed from the target gene, wherein the anti-parasitic, anti-pest or insecticidal nucleic acid molecule does not comprise a sequence that is 100% identical or complementary to 5, 6, 7, 8, 9, 10, 11, 12, 13, 14, 15, 16, 17, 18, 19, 20, 21, 22, 23, 24, 25 or more contiguous nucleotides of gene sequence of a non-target organism. In an aspect, a composition comprises an anti-parasitic, anti-pest or insecticidal nucleic acid molecule having 99 percent sequence identity to a region of at least 35 contiguous nucleotides in the target gene or RNA transcribed from the target gene, wherein the anti-parasitic, anti-pest or insecticidal nucleic acid molecule does not comprise a sequence that is 100% identical or complementary to 5, 6, 7, 8, 9, 10, 11, 12, 13, 14, 15, 16, 17, 18, 19, 20, 21, 22, 23, 24, 25 or more contiguous nucleotides of gene sequence of a non-target organism. In an aspect, a composition comprises an anti-parasitic, anti-pest or insecticidal nucleic acid molecule having 99 percent sequence identity to a region of at least 40 contiguous nucleotides in the target gene or RNA transcribed from the target gene, wherein the anti-parasitic, anti-pest or insecticidal nucleic acid molecule does not comprise a sequence that is 100% identical or complementary to 5, 6, 7, 8, 9, 10, 11, 12, 13, 14, 15, 16, 17, 18, 19, 20, 21, 22, 23, 24, 25 or more contiguous nucleotides of gene sequence of a non-target organism. In an aspect, a composition comprises an anti-parasitic, anti-pest or insecticidal nucleic acid molecule having 99 percent sequence identity to a region of at least 50 contiguous nucleotides in the target gene or RNA transcribed from the target gene, wherein the anti-parasitic, anti-pest or insecticidal nucleic acid molecule does not comprise a sequence that is 100% identical or complementary to 5, 6, 7, 8, 9, 10, 11, 12, 13, 14, 15, 16, 17, 18, 19, 20, 21, 22, 23, 24, 25 or more contiguous nucleotides of gene sequence of a non-target organism. In an aspect, a composition comprises an anti-parasitic, anti-pest or insecticidal nucleic acid molecule having 99 percent sequence identity to a region of at least 60 contiguous nucleotides in the target gene or RNA transcribed from the target gene, wherein the anti-parasitic, anti-pest or insecticidal nucleic acid molecule does not comprise a sequence that is 100% identical or complementary to 5, 6, 7, 8, 9, 10, 11, 12, 13, 14, 15, 16, 17, 18, 19, 20, 21, 22, 23, 24, 25 or more contiguous nucleotides of gene sequence of a non-target organism. In some aspects, an anti-parasitic, anti-pest or insecticidal nucleic acid has at least 98 percent sequence identity to a region of the target gene, wherein the anti-parasitic, anti-pest or insecticidal nucleic acid molecule does not comprise a sequence that is 100% identical or complementary to 5, 6, 7, 8, 9, 10, 11, 12, 13, 14, 15, 16, 17, 18, 19, 20, 21, 22, 23, 24, 25 or more contiguous nucleotides of gene sequence of a non-target organism. In an aspect, an anti-parasitic, anti-pest or insecticidal nucleic acid has at least 97 percent sequence identity to a region of the target gene, wherein the anti-parasitic, anti-pest or insecticidal nucleic acid molecule does not comprise a sequence that is 100% identical or complementary to 5, 6, 7, 8, 9, 10, 11, 12, 13, 14, 15, 16, 17, 18, 19, 20, 21, 22, 23, 24, 25 or more contiguous nucleotides of gene sequence of a non-target organism. In some aspects, an anti-parasitic, anti-pest or insecticidal nucleic acid has at least 96 percent sequence identity to a region of the target gene, wherein the anti-parasitic, anti-pest or insecticidal nucleic acid molecule does not comprise a sequence that is 100% identical or complementary to 5, 6, 7, 8, 9, 10, 11, 12, 13, 14, 15, 16, 17, 18, 19, 20, 21, 22, 23, 24, 25 or more contiguous nucleotides of gene sequence of a non-target organism. In an aspect, an anti-parasitic, anti-pest or insecticidal nucleic acid has at least 95 percent sequence identity to a region of the target gene, wherein the anti-parasitic, anti-pest or insecticidal nucleic acid molecule does not comprise a sequence that is 100% identical or complementary to 5, 6, 7, 8, 9, 10, 11, 12, 13, 14, 15, 16, 17, 18, 19, 20, 21, 22, 23, 24, 25 or more contiguous nucleotides of gene sequence of a non-target organism. In some aspects, an anti-parasitic, anti-pest or insecticidal nucleic acid has at least 94 percent sequence identity to a region of the target gene, wherein the anti-parasitic, anti-pest or insecticidal nucleic acid molecule does not comprise a sequence that is 100% identical or complementary to 5, 6, 7, 8, 9, 10, 11, 12, 13, 14, 15, 16, 17, 18, 19, 20, 21, 22, 23, 24, 25 or more contiguous nucleotides of gene sequence of a non-target organism. In an aspect, an anti-parasitic, anti-pest or insecticidal nucleic acid has at least 93 percent sequence identity to a region of the target gene, wherein the anti-parasitic, anti-pest or insecticidal nucleic acid molecule does not comprise a sequence that is 100% identical or complementary to 5, 6, 7, 8, 9, 10, 11, 12, 13, 14, 15, 16, 17, 18, 19, 20, 21, 22, 23, 24, 25 or more contiguous nucleotides of gene sequence of a non-target organism. In some aspects, an anti-parasitic, anti-pest or insecticidal nucleic acid has at least 92 percent sequence identity to a region of the target gene, wherein the anti-parasitic, anti-pest or insecticidal nucleic acid molecule does not comprise a sequence that is 100% identical or complementary to 5, 6, 7, 8, 9, 10, 11, 12, 13, 14, 15, 16, 17, 18, 19, 20, 21, 22, 23, 24, 25 or more contiguous nucleotides of gene sequence of a non-target organism. In an aspect, an anti-parasitic, anti-pest or insecticidal nucleic acid has at least 91 percent sequence identity to a region of the target gene, wherein the anti-parasitic, anti-pest or insecticidal nucleic acid molecule does not comprise a sequence that is 100% identical or complementary to 5, 6, 7, 8, 9, 10, 11, 12, 13, 14, 15, 16, 17, 18, 19, 20, 21, 22, 23, 24, 25 or more contiguous nucleotides of gene sequence of a non-target organism. In an aspect, an anti-parasitic, anti-pest or insecticidal nucleic acid has at least about 83, 84, 85, 86, 87, 88, 89, 90 percent identity to a region of the target gene as provided above, wherein the anti-parasitic, anti-pest or insecticidal nucleic acid molecule does not comprise a sequence that is 100% identical or complementary to 5, 6, 7, 8, 9, 10, 11, 12, 13, 14, 15, 16, 17, 18, 19, 20, 21, 22, 23, 24, 25 or more contiguous nucleotides of gene sequence of a non-target organism. In an aspect, a target gene may be a gene comprising SEQ ID NO: 1 to 89 or 93. In an aspect, a target gene may be a gene comprising SEQ ID NO: 1. In an aspect, a target gene may be a gene comprising SEQ ID NO: 2. In an aspect, a target gene may be a gene comprising SEQ ID NO: 3. In an aspect, a target gene may be a gene comprising SEQ ID NO: 4. In an aspect, a target gene may be a gene comprising SEQ ID NO: 69. In an aspect, a target gene may be a gene comprising SEQ ID NO: 70. In an aspect, a target gene may be a gene comprising SEQ ID NO: 88. In an aspect, a target gene may be a gene comprising SEQ ID NO: 89. In an aspect, a target gene may be a gene comprising sequence selected from SEQ ID NOs:71-87.

In some embodiments, an anti-parasitic, anti-pest or insecticidal nucleic acid has at least one nucleotide deleted in comparison to a target gene sequence. In one aspect, the anti-parasitic, anti-pest or insecticidal nucleic acid does not contain a sequence of 5, 6, 7, 8, 9, 10, 11, 12, 13, 14, 15, 16, 17, 18, 19, 20, 21, 22, 23, 24, 25 or more consecutive nucleotides that is identical or complementary to a gene sequence in a non-targeting organism. In one embodiment, the non-targeting organism is a bee. In another embodiment, the non-targeting organism is a human. In another embodiment, the non-targeting organism is a monarch butterfly. In some embodiments, the anti-parasitic, anti-pest or insecticidal nucleic acid has at least one, at least two, at least three, at least four, at least five, at least six, at least seven, at least eight, at least nine, at least ten, at least eleven, at least twelve, at least thirteen, at least fourteen, at least fifteen, or more nucleotides deleted in comparison to a target sequence. In some embodiments, the at least two, at least three, at least four, at least five, or at least six nucleotides deleted are contiguous in the reference calmodulin gene sequence. In other embodiments, the at least one, at least two, at least three, at least four, at least five, at least six, at least seven, at least eight, at least nine, at least ten, at least eleven, at least twelve, at least thirteen, at least fourteen, at least fifteen, or more deleted nucleotides are not contiguous in the target sequence. In an aspect, the target sequence may be selected from SEQ ID NO: 1 to 89, 93 or a portion thereof. In an aspect, a target sequence may be a gene comprising SEQ ID NO: 1 or a portion thereof. In an aspect, a target sequence may be a gene comprising SEQ ID NO: 2 or a portion thereof. In an aspect, a target sequence may be a gene comprising SEQ ID NO: 3 or a portion thereof. In an aspect, a target sequence may be a gene comprising SEQ ID NO: 4 or a portion thereof. In an aspect, a target sequence may be a gene comprising SEQ ID NO: 69 or a portion thereof. In an aspect, a target sequence may be a gene comprising SEQ ID NO: 70 or a portion thereof. In an aspect, a target sequence may be a gene comprising SEQ ID NO: 88 or a portion thereof. In an aspect, a target sequence may be a gene comprising SEQ ID NO: 89 or a portion thereof. In an aspect, a target sequence may be a gene comprising a sequence selected from SEQ ID NOs:71-87 or a portion thereof. In some embodiments, the anti-parasitic, anti-pest or insecticidal nucleic acid comprises a sequence that has at least about 80, 81, 82, 83, 84, 85, 86, 87, 88, 89, 90, 91, 92, 93, 94, 95, 96, 97, 98, 99 or 100 percent sequence identity to a sequence selected from SEQ ID NOs:90-92 or 94, or a part thereof. In some embodiments, the anti-parasitic, anti-pest or insecticidal nucleic acid comprises the reverse complement of a sequence that has at least about 80, 81, 82, 83, 84, 85, 86, 87, 88, 89, 90, 91, 92, 93, 94, 95, 96, 97, 98, 99 or 100 percent sequence identity to a sequence selected from SEQ ID NOs:90-92 or 94, or a part thereof. In some embodiments, the anti-parasitic, anti-pest or insecticidal nucleic acid comprises at least 18 contiguous nucleotides of a sequence selected from SEQ ID NOs: 90-92 or 94. In some embodiments, the anti-parasitic, anti-pest or insecticidal nucleic acid comprises a sequence selected from SEQ ID NOs:90-92 or 94, or a part thereof. In some embodiments, the anti-parasitic, anti-pest or insecticidal nucleic acid comprises a sequence selected from SEQ ID NOs:90-92 and 94, and the reverse complement of a sequence selected from SEQ ID NOs:90-92 and 94.

This application provides and discloses compositions comprising an anti-parasitic, anti-pest or insecticidal nucleic acid molecule and an excipient substance. In an aspect, the excipient can be a combination of one or more inactive components. In some aspects, the excipient comprises a sugar. Examples of sugars include hexoses, disaccharides, trisaccharides and higher sugars. Excipient sugars include, for example, fructose, glucose, sucrose, trehalose, lactose, galactose, ribose. In other aspects the excipient comprises a sugar and a solvent. In other aspects, the excipient comprises a protein. In an aspect, the protein is a soy protein. In other aspects the excipient may be pollen. In aspects according to the present disclosure, the excipient may be a bee food. In some aspects, the excipient comprises Tryptone. In some aspects, the excipient comprises yeast extract. In some aspects, the excipient comprises an essential oil.

Bee feeding is common practice amongst bee-keepers, for providing both nutritional and other, for example, supplemental needs. Bees typically feed on honey and pollen, but have been known to ingest non-natural feeds as well. Bees can be fed various foodstuffs including, but not limited to Wheast (a dairy yeast grown on cottage cheese), soybean flour, yeast (e.g. brewer's yeast, torula yeast) and yeast products products-fed singly or in combination and soybean flour fed as a dry mix or moist cake inside the hive or as a dry mix in open feeders outside the hive. Also useful is sugar, or a sugar syrup. The addition of 10 to 12 percent pollen to a supplement fed to bees improves palatability. The addition of 25 to percent pollen improves the quality and quantity of essential nutrients that are required by bees for vital activity. Cane or beet sugar, isomerized corn syrup, and type-50 sugar syrup are satisfactory substitutes for honey in the natural diet of honey bees. The last two can be supplied only as a liquid to bees. Liquid feed can be supplied to bees inside the hive by, for example, any of the following methods: friction-top pail, combs within the brood chamber, division board feeder, boardman feeder, etc. Dry sugar may be fed by placing a pound or two on the inverted inner cover. A supply of water must be available to bees at all times. In one aspect, pan or trays in which floating supports-such as wood chips, cork, or plastic sponge—are present are envisaged. Detailed descriptions of supplemental feeds for bees can be found in, for example, USDA publication by Standifer, et al. 1977, entitled "Supplemental Feeding of Honey Bee Colonies" (USDA, Agriculture Information Bulletin No. 413).

In aspects according to the present disclosure, an anti-parasitic, anti-pest or insecticidal nucleic acid, for example a dsRNA, is absorbable. As used herein "absorbable," refers to mechanisms the provide for the uptake of a nucleic acid that is not by ingestion. In an aspect, an anti-parasitic, anti-pest or insecticidal nucleic acid may be absorbed through the skin of an organism, or the exoskeleton of an arthropod. In an aspect, an absorbable nucleic acid is dissolved in an excipient. In other aspects, an absorbable nucleic acid is suspended in an excipient. Excipients for solvation or suspension may be aqueous or non-aqueous. In some aspects, the anti-parasitic, anti-pest or insecticidal nucleic acid is absorbed by a host organism and transferred to a parasitic organism by feeding. In other aspects, the anti-parasitic, anti-pest or insecticidal nucleic acid is absorbed by a host organism and transferred to a parasitic organism by absorption. In an aspect, an anti-parasitic, anti-pest or insecticidal nucleic acid of the present disclosure is absorbed directly by the parasite.

In aspects according to the present disclosure an anti-parasitic, anti-pest or insecticidal nucleic acid, for example a dsRNA, is combined with an excipient. In an aspect, the nucleic acid may be provided as a ratio of nucleic acid to excipient. In an aspect, the ratio may be one part nucleic acid to 4 parts excipient. In an aspect the ratio of nucleic acid to excipient may be 1:1, 1:2, 1:5, or 1:10. In other aspects, the ratio of nucleic acid to excipient may be 1:20, 1:25, 1:30, 1:40, or more. In an aspect, ratio of nucleic acid to excipient may be 1:50. In aspects according to the present disclosure, the ratio may be determined as a volume to volume (v/v) ratio, a weight:weight (w/w) ratio. In certain aspects, the ratio may be expressed as a weight:volume (w/v) ratio. In certain aspects, a nucleic acid and an excipient may be a dsRNA and an excipient.

In aspects according to the present disclosure, the composition may comprise a weight of an anti-parasitic, anti-pest or insecticidal nucleic acid combined with an excipient. In an aspect, the nucleic acid may comprise a percentage of the total weight of the composition. In an aspect, the nucleic acid may comprise about 0.1% by weight of the composition. In an aspect, the nucleic acid may comprise about 0.2% by weight of the composition. In an aspect, the nucleic acid may comprise about 0.3% by weight of the composition. In another aspect, the nucleic acid may comprise about 0.4% by weight of the composition. In an aspect, the nucleic acid may comprise up to 0.5% by weight of the composition. In an aspect, the nucleic acid may comprise up to 0.6% by weight of the composition. In an aspect, the nucleic acid may comprise up to 0.7% by weight of the composition. In an aspect, the nucleic acid may comprise up to 0.8% by weight of the composition. In another aspect, the nucleic acid may comprise up to 1.0% by weight of the composition. In other aspects, the nucleic acid may comprise up to 1.5% by weight of the composition. In yet other aspects, the nucleic acid may comprise up to 2.0% by weight, or 2.5% by weight of the composition. In certain aspects, a nucleic acid and an excipient may be a dsRNA and an excipient.

The present disclosure provides for, and includes, compositions having from 0.1% to 5% by weight of one or more anti-parasitic, anti-pest or insecticidal nucleic acids. In other aspects, a composition may comprise from 0.1 to 4%, 0.1 to 3%, 0.1 to 2%, 0.1 to 1%, 0.1 to 2%, 0.1 to 3%, or 0.1 to 4% by weight nucleic acid. In an aspect, a composition may comprise from 0.2% to 5% by weight nucleic acid. In other aspects, a composition may comprise from 0.2 to 4%, 0.2 to 3%, 0.2 to 2%, 0.2 to 1%, 0.2 to 2%, 0.2 to 3%, or 0.2 to 4% by weight nucleic acid. In other aspects, a composition may comprise up to 1%, up to 2%, up to 3%, up to 4%, or up to 5% nucleic acid. In other aspects, a composition may comprise up to 7.5%, up to 10%, or up to 15% nucleic acid. In certain aspects, a nucleic acid and an excipient may be a dsRNA and an excipient.

The present disclosure provides for, and includes, compositions having from 0.1 to 10 mg/ml of one ore more anti-parasitic, anti-pest or insecticidal nucleic acids. In other aspects, a composition may comprise from 0.1 to 1.0 mg/ml, 0.1 to 2.0 mg/ml, 0.1 to 2.5 mg/ml, 0.1 to 5 mg/ml, 0.1 to 10 mg/ml, 0.1 to 15 mg/ml, or 0.1 to 20 mg/ml nucleic acid. In certain aspects, a composition may comprise at least 0.1 μg/ml nucleic acid. In certain other aspects, a composition may comprise at least 1.0 μg/ml nucleic acid. In yet other aspects, a composition may comprise at least 10 μg/ml nucleic acid. In an aspect, a composition may comprise from 0.5 to 10 mg/ml nucleic acid. In other aspects, a composition may comprise from 0.5 to 1.0 mg/ml, 0.5 to 2.0 mg/ml, 0.5 to 2.5 mg/ml, 0.5 to 5 mg/ml, 0.5 to 10 mg/ml, 0.5 to 15 mg/ml, or 0.5 to 20 mg/ml nucleic acid. In an aspect, a composition may comprise from 1.0 to 10 mg/ml nucleic acid. In other aspects, a composition may comprise from 1.0 to 2.0 mg/ml, 1.0 to 2.5 mg/ml, 1.0 to 5 mg/ml, 1.0 to 10 mg/ml, 1.0 to 15 mg/ml, or 1.0 to 20 mg/ml nucleic acid. In certain aspects, the anti-parasitic, anti-pest or insecticidal nucleic acid in the composition comprises a dsRNA.

The present disclosure, provides for, and includes selective insecticide compositions and methods of using selective insecticide compositions.

As used herein, a "selective insecticide composition," is a composition that is more effective for one or more arthropod species and is less effective for one or more different arthropod species. A selective insecticide composition includes compositions that kill adults or immature arthropods and includes compositions that are larvicides and ovicides. A selective insecticide may be a systemic insecticides incorporated by treated food, including the blood or hemolymph obtained from a host organisms. A selective insecticide may be a contact insecticides are toxic to certain insects brought into direct contact, and are non-toxic or minimally toxic to certain other insects. In some embodiments, a selective insecticide composition is anti-pest. In some embodiments, a selective insecticide composition is anti-parasitic. In some embodiments, a selective insecticide composition is a miticide. In some embodiments, a selective insecticide composition is toxic to a targeted parasitic or pest insect and non-toxic or minimally toxic to non-target organisms. Examples of non-target organisms include, but are not limited to beneficial insects, nematodes, birds, mammals, and plants. In some embodiments, a selective insecticide composition is toxic to a parasitic insect, for example *Varroa* mite, and non-toxic or minimally toxic to the host organism, for example bees. In some embodiments, a selective insecticide composition is toxic to one or more pest or parasitic insects selected from the group consisting of: *Varroa destructor, Ixodes scapularis, Solenopsis invicta, Tetranychus urticae, Aedes aegypti, Culex quinquefasciatus, Acyrthosiphon pisum,* and *Pediculus humanus.*

In certain aspects according to the present disclosure, a selective insecticide may be incorporated into a bacteria or yeast by genetic modification (for example, a transgenic bacteria or yeast engineered to express a nucleic acid of the present disclosure). A selective insecticide introduced by genetic modification of a bacteria or yeast may act directly on the pest organism, or indirectly by being ingested by a host of the pest organism.

In an aspect according to the present disclosure, a selective insecticide may be a more effective insecticide against one or more first insects than against one or more second insects. In an aspect, a selective insecticide may be toxic to a first insect and have no effect on a second insect. In an aspect, a selective insecticide may be toxic to a first insect and require significantly higher concentrations or amounts to have an effect on a second insect. In an aspect, a selective insecticide may be 2 times or more toxic to a first insect compared to a second insect. In an aspect, a selective insecticide may be 4 times or more toxic to a first insect compared to a second insect. In an aspect, a selective insecticide may be 5 times or more toxic to a first insect compared to a second insect. In an aspect, a selective insecticide may be 10 times or more toxic to a first insect compared to a second insect.

In an aspect, a selective insecticide may inhibit the growth, development or fecundity of a first insect and have no effect on a second insect. In an aspect, a selective insecticide may inhibit the growth, development or fecundity a first insect and require significantly higher concentrations or amounts to have a similar effect on a second insect. In an aspect, a selective insecticide may require 2 times or more of the active ingredient to inhibit the growth, development or fecundity of a second insect. In an aspect, a selective insecticide may require 4 times or more of the active ingredient to inhibit the growth, development or fecundity of a second insect. In an aspect, a selective insecticide may require 5 times or more of the active ingredient to inhibit the growth, development or fecundity of a second insect. In an aspect, a selective insecticide may require 10 times or more of the active ingredient to inhibit the growth, development or fecundity of a second insect.

Several embodiments relate to a method of altering an anti-parasitic, anti-pest or insecticidal nucleic acid molecule to reduce or eliminate regions of sequence complentarity or identity to a gene sequence of a non-target organism. In some embodiments, potential anti-parasitic, anti-pest or insecticidal nucleic acid sequences are compared to an appropriate genomic database of one or more non-target organisms (non-limited examples of non-target organisms include human, bee, monarch butterfly, mouse, rat etc.) using any sequence alignment software, such as the BLAST software available from the NCBI server (available on the internet at www.ncbi.nlm.nih.gov/BLAST/). In some embodiments, putative anti-parasitic, anti-pest or insecticidal nucleic acid molecules which exhibit significant homology to gene sequences of one or more non-target organisms are filtered out. In some embodiments, the nucleotide sequence of putative anti-parasitic, anti-pest or insecticidal nucleic acid molecules which exhibit regions of sequence complentarity or identity to a gene sequence of a non-target organism are changes in order to reduce, eliminate or disrupt such regions of sequence complentarity or identity. In some embodiments, one or more nucleotides are changed, added, or deleted compared to the target sequence to disrupt sequences having 5, 6, 7, 8, 9, 10, 11, 12, 13, 14, 15, 16, 17, 18, 19, 20, 21, 22, 23, 24, 25, 26, 27, 28, 29, 30 or more contiguous nucleotides that are identical or complementary to a gene sequence of a non-target organism. In some embodiments, 1, 2, 3, 4, 5, 6, 7, 8, 9, 10 or more nucleotides are changed, added, or deleted compared to the target sequence such that the anti-parasitic, anti-pest or insecticidal nucleic acid molecule does not comprise a sequence of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more contiguous nucleotides that are identical or complementary to a gene sequence of a non-target organism.

The present disclosure further includes, and provides for, methods of treating or preventing Colony Collapse Disorder in a honeybee colony, comprising providing an effective amount of a composition comprising a nucleic acid that is essentially identical or essentially complementary to a region of a *Varroa destructor* calmodulin gene sequence to a honeybee whereby the level of *Varroa destructor* infestation is reduced. In an aspect, the method comprises providing an effective amount of a composition comprising a nucleic acid that is essentially identical or essentially complementary to at least 19 contiguous nucleotides of SEQ ID NO: 1 and does not comprise a sequence of 5, 6, 7, 8, 9, 10, 11, 12, 13, 14, 15, 16, 17, 18, 19, 20, 21, 22, 23, 24, 25 or more contiguous nucleotides that are 100% identical or complementary to a gene sequence of a non-target organism. In an aspect, the method comprises providing an effective amount of a composition comprising a nucleic acid that is essentially identical or essentially complementary to at least 19 contiguous nucleotides of SEQ ID NO: 2 and does not comprise a sequence of 5, 6, 7, 8, 9, 10, 11, 12, 13, 14, 15, 16, 17, 18, 19, 20, 21, 22, 23, 24, 25 or more contiguous nucleotides that are 100% identical or complementary to a gene sequence of a non-target organism. In an aspect, the method comprises providing an effective amount of a composition comprising a nucleic acid that is essentially identical or essentially complementary to at least 19 contiguous nucleotides of SEQ ID NO: 69 and does not comprise a sequence of 5, 6, 7, 8, 9, 10, 11, 12, 13, 14, 15, 16, 17, 18, 19, 20, 21, 22, 23, 24, 25 or more contiguous nucleotides that are 100% identical or complementary to a gene sequence of a non-target organism. In an aspect, the method comprises providing an effective amount of a composition comprising a nucleic acid that is essentially identical or essentially complementary to at least 19 contiguous nucleotides of SEQ ID NO: 70 and does not comprise a sequence of 5, 6, 7, 8, 9, 10, 11, 12, 13, 14, 15, 16, 17, 18, 19, 20, 21, 22, 23, 24, 25 or more contiguous nucleotides that are 100% identical or complementary to a gene sequence of a non-target organism. In an aspect, the method comprises providing an effective amount of a composition comprising a nucleic acid according to SEQ ID NO: 3 and does not comprise a sequence of 5, 6, 7, 8, 9, 10, 11, 12, 13, 14, 15, 16, 17, 18, 19, 20, 21, 22, 23, 24, 25 or more contiguous nucleotides that are 100% identical or complementary to a gene sequence of a non-target organism. In an aspect, the method comprises providing an effective amount of a composition comprising a nucleic acid according to SEQ ID NO: 4 and does not comprise a sequence of 5, 6, 7, 8, 9, 10, 11, 12, 13, 14, 15, 16, 17, 18, 19, 20, 21, 22, 23, 24, 25 or more contiguous nucleotides that are 100% identical or complementary to a gene sequence of a non-target organism. In an aspect, the method comprises providing an effective amount of a composition comprising a nucleic acid according to SEQ ID NO: 88 and does not comprise a sequence of 5, 6, 7, 8, 9, 10, 11, 12, 13, 14, 15, 16, 17, 18, 19, 20, 21, 22, 23, 24, 25 or more contiguous nucleotides that are 100% identical or complementary to a gene sequence of a non-target organism. In an aspect, the method comprises providing an effective amount of a composition comprising a nucleic acid according to SEQ ID NO: 89 and does not comprise a sequence of 5, 6, 7, 8, 9, 10, 11, 12, 13, 14, 15, 16, 17, 18, 19, 20, 21, 22, 23, 24, 25 or more contiguous nucleotides that are 100% identical or complementary to a gene sequence of a non-target organism. In an aspect, the method comprises providing an effective amount of a composition comprising a nucleic acid according to SEQ ID NO: 90. In an aspect, the method comprises providing an effective amount of a composition comprising a nucleic acid according to SEQ ID NO: 91. In an aspect, the method comprises providing an effective amount of a composition comprising a nucleic acid according to SEQ ID NO: 92. In an aspect, the method comprises providing an effective amount of a composition comprising a nucleic acid according to SEQ ID NO: 93. In an aspect, the method comprises providing an effective amount of a composition comprising a nucleic acid according to SEQ ID NO: 94. In an aspect, the method comprises providing an effective amount of a composition comprising a nucleic acid according to SEQ ID NO: 90 and a nucleic acid that is the reverse complement of SEQ ID NO: 90. In an aspect, the method comprises providing an effective amount of a composition comprising a nucleic acid according to SEQ ID NO: 91 and a nucleic acid that is the reverse complement of SEQ ID NO: 91. In an aspect, the method comprises providing an effective amount of a composition comprising a nucleic acid according to SEQ ID NO: 92 and a nucleic acid that is the reverse complement of SEQ ID NO: 92. In an aspect, the method comprises providing an effective amount of a composition comprising a nucleic acid according to SEQ ID NO: 93 and a nucleic acid that is the reverse complement of SEQ ID NO: 93. In an aspect, the method comprises providing an effective amount of a composition comprising a nucleic acid according to SEQ ID NO: 94 and a nucleic acid that is the reverse complement of SEQ ID NO: 94. In an aspect, the method comprises providing an effective amount of a composition comprising two or more nucleic acids having a sequence selected from the group consisting of: SEQ ID NOs: 3, 4, 88, 89, 90-93. In an aspect, the method comprises providing an effective amount of a composition comprising a nucleic acid that is essentially identical or essentially complementary to at least 19 contiguous nucleotides of a sequence selected from SEQ ID NOs: 71-87 and does not comprise a sequence of 5, 6, 7, 8, 9, 10, 11, 12, 13, 14, 15, 16, 17, 18, 19, 20, 21, 22, 23, 24, 25 or more contiguous nucleotides that are 100% identical or complementary to a gene sequence of a non-target organism. In an aspect, the method comprises providing an effective amount of a composition comprising a nucleic acid that is essentially identical or essentially complementary to at least 23 contiguous nucleotides of a sequence selected from SEQ ID NOs: 71-87 and does not comprise a sequence of 5, 6, 7, 8, 9, 10, 11, 12, 13, 14, 15, 16, 17, 18, 19, 20, 21, 22, 23, 24, 25 or more contiguous nucleotides that are 100% identical or complementary to a gene sequence of a non-target organism. In an aspect, the method comprises providing an effective amount of a composition comprising a nucleic acid that is essentially identical or essentially complementary to at least 30 contiguous nucleotides of a sequence selected from SEQ ID NOs: 71-87 and does not comprise a sequence of 5, 6, 7, 8, 9, 10, 11, 12, 13, 14, 15, 16, 17, 18, 19, 20, 21, 22, 23, 24, 25 or more contiguous nucleotides that are 100% identical or complementary to a gene sequence of a non-target organism. In an aspect, the method comprises providing an effective amount of a composition comprising a nucleic acid that is essentially identical or essentially complementary to at least 40 contiguous nucleotides of a sequence selected from SEQ ID NOs: 71-87 and does not comprise a sequence of 5, 6, 7, 8, 9, 10, 11, 12, 13, 14, 15, 16, 17, 18, 19, 20, 21, 22, 23, 24, 25 or more contiguous nucleotides that are 100% identical or complementary to a gene sequence of a non-target organism. In an aspect, the method comprises providing an effective amount of a composition comprising a nucleic acid that is essentially identical or essentially complementary to at least 50 contiguous nucleotides of a sequence selected from SEQ ID NOs: 71-87 and does not comprise a sequence of 5, 6, 7, 8, 9, 10, 11, 12, 13, 14, 15, 16, 17, 18, 19, 20, 21, 22, 23, 24, 25 or more contiguous nucleotides that are 100% identical or complementary to a gene sequence of a non-target organism. In an aspect, the method comprises providing an effective amount of a composition comprising a nucleic acid that is essentially identical or essentially complementary to at least 60 contiguous nucleotides of a sequence selected from SEQ ID NOs: 71-87 and does not comprise a sequence of 5, 6, 7, 8, 9, 10, 11, 12, 13, 14, 15, 16, 17, 18, 19, 20, 21, 22, 23, 24, 25 or more contiguous nucleotides that are 100% identical or complementary to a gene sequence of a non-target organism. In an aspect, the method comprises providing an effective amount of a composition comprising a nucleic acid that is essentially identical or essentially complementary to at least 70 contiguous nucleotides of a sequence selected from SEQ ID NOs: 71-87 and does not comprise a sequence of 5, 6, 7, 8, 9, 10, 11, 12, 13, 14, 15, 16, 17, 18, 19, 20, 21, 22, 23, 24, 25 or more contiguous nucleotides that are 100% identical or complementary to a gene sequence of a non-target organism. In an aspect, the method comprises providing an effective amount of a composition comprising a nucleic acid that is essentially identical or essentially complementary to at least 80 contiguous nucleotides of a sequence selected from SEQ ID NOs: 71-87 and does not comprise a sequence of 5, 6, 7, 8, 9, 10, 11, 12, 13, 14, 15, 16, 17, 18, 19, 20, 21, 22, 23, 24, 25 or more contiguous nucleotides that are 100% identical or complementary to a gene sequence of a non-target organism. In an aspect, the method comprises providing an effective amount of a composition comprising a nucleic acid that is essentially identical or essentially complementary to at least 90 contiguous nucleotides of a sequence selected from SEQ ID NOs: 71-87 and does not comprise a sequence of 5, 6, 7, 8, 9, 10, 11, 12, 13, 14, 15, 16, 17, 18, 19, 20, 21, 22, 23, 24, 25 or more contiguous nucleotides that are 100% identical or complementary to a gene sequence of a non-target organism. In an aspect, the method comprises providing an effective amount of a composition comprising a nucleic acid that is essentially identical or essentially complementary to at least 100 contiguous nucleotides of a sequence selected from SEQ ID NOs: 71-87 and does not comprise a sequence of 5, 6, 7, 8, 9, 10, 11, 12, 13, 14, 15, 16, 17, 18, 19, 20, 21, 22, 23, 24, 25 or more contiguous nucleotides that are 100% identical or complementary to a gene sequence of a non-target organism. In an aspect, the method comprises providing an effective amount of a composition comprising a nucleic acid that is essentially identical or essentially complementary to at least 110 contiguous nucleotides of a sequence selected from SEQ ID NOs: 71-87 and does not comprise a sequence of 5, 6, 7, 8, 9, 10, 11, 12, 13, 14, 15, 16, 17, 18, 19, 20, 21, 22, 23, 24, 25 or more contiguous nucleotides that are 100% identical or complementary to a gene sequence of a non-target organism. In an aspect, the method comprises providing an effective amount of a composition comprising a nucleic acid that is essentially identical or essentially complementary to at least 120 contiguous nucleotides of a sequence selected from SEQ ID NOs: 71-87 and does not comprise a sequence of 5, 6, 7, 8, 9, 10, 11, 12, 13, 14, 15, 16, 17, 18, 19, 20, 21, 22, 23, 24, 25 or more contiguous nucleotides that are 100% identical or complementary to a gene sequence of a non-target organism. In an aspect, the method comprises providing an effective amount of a composition comprising a nucleic acid that is essentially identical or essentially complementary to at least 130 contiguous nucleotides of a sequence selected from SEQ ID NOs: 71-87 and does not comprise a sequence of 5, 6, 7, 8, 9, 10, 11, 12, 13, 14, 15, 16, 17, 18, 19, 20, 21, 22, 23, 24, 25 or more contiguous nucleotides that are 100% identical or complementary to a gene sequence of a non-target organism. In an aspect, the method comprises providing an effective amount of a composition comprising a nucleic acid that is essentially identical or essentially complementary to at least 140 contiguous nucleotides of a sequence selected from SEQ ID NOs: 71-87 and does not comprise a sequence of 5, 6, 7, 8, 9, 10, 11, 12, 13, 14, 15, 16, 17, 18, 19, 20, 21, 22, 23, 24, 25 or more contiguous nucleotides that are 100% identical or complementary to a gene sequence of a non-target organism. In an aspect, the method comprises providing an effective amount of a composition comprising a nucleic acid that is essentially identical or essentially complementary to a sequence selected from SEQ ID NOs: 71-87. In an aspect, the method comprises providing an effective amount of a composition comprising a nucleic acid according to a sequence selected from SEQ ID NOs: 71-87. In an aspect, the method comprises providing an effective amount of a composition comprising a nucleic acid according to a sequence selected from SEQ ID NOs: 90-94.

The present disclosure provides for, and includes, methods for reducing the parasite load of a host organism. In an aspect, the parasite load refers to the number of parasites per individual host. In an aspect, the parasite load refers to the average number of parasites per 100 host organisms. In an aspect, the parasite load may refer to the number of parasites per colony of parasite hosts. In aspects according to the present disclosure the parasite is *Varroa destructor* and the host is the honey bee, *Apis mellifera*. In certain aspects, the parasite load refers to the number of *Varroa destructor* parasites per 100 honeybees in a colony. In some embodiments, the present disclosure provides for, and includes, methods and compositions for reducing the parasite load to less than 6 *Varroa destructor* parasites per 100 honeybees in a colony. In some embodiments, the present disclosure provides for, and includes, methods and compositions for reducing the parasite load to less than 5 *Varroa destructor* parasites per 100 honeybees in a colony. In some embodiments, the present disclosure provides for, and includes, methods and compositions for reducing the parasite load to less than 4 *Varroa destructor* parasites per 100 honeybees in a colony. In some embodiments, the present disclosure provides for, and includes, methods and compositions for reducing the parasite load to less than 2 *Varroa destructor* parasites per 100 honeybees in a colony.

In an aspect, the methods of reducing a parasite load comprises providing an effective amount of an anti-parasitic, anti-pest or insecticidal nucleic acid composition to a host organism. An effective amount of a composition of the present disclosure results in a decrease in the parasite load over a period of time. In an aspect, a decrease in parasite load may measured within one day of providing an effective amount of a nucleic acid composition. In an aspect, the parasite load may be measured after two days. In an aspect, the parasite load may be measured after 3 days. In other aspects, the parasite load may be measured after 5 days or after 1 week. In another aspect, the parasite load may be measured more than one time, for example every 3 days, every 5 days, every week or once a month. In certain aspects, according to the present disclosure, a decrease in the number of parasites may be measured and compared to an untreated control organism or colony. In aspects according to the present disclosure the parasite is *Varroa destructor* and the host is the honey bee, *Apis mellifera*.

In aspects according to the present disclosure, a reduction in parasite load after a period of time means a decrease in the number of parasites. In an aspect, the number of parasites may decrease by 10%, 20%, 30% or more between measurements. In another aspect, the number of parasites may decrease by 40% or more between measurements. In another aspect, the number of parasites may decrease by 50% or more between measurements. In another aspect, the number of parasites may decrease by 60% or more between measurements. In another aspect, the number of parasites may decrease by 70% or more between measurements. In another aspect, the number of parasites may decrease by 80% or more between measurements. In another aspect, the number of parasites may decrease by 90% or more between measurements.

In other aspects, the parasite load may be measured as the average number of parasites per host organism. In an aspect, a decreased parasitic load may comprise fewer than 20 parasites per 100 host organisms. In an aspect, a decreased parasitic load may comprise fewer than 15 parasites per 100 host organisms. In an aspect, a decreased parasitic load may comprise fewer than 10 parasites per 100 host organisms. In an aspect, a decreased parasitic load may comprise fewer than 5 parasites per 100 host organisms. In an aspect, a decreased parasitic load may comprise fewer than 4 parasites per 100 host organisms. In an aspect, a decreased parasitic load may comprise fewer than 3 parasites per 100 host organisms. In an aspect, a decreased parasitic load may comprise fewer than 2 parasites per 100 host organisms. In an aspect, a decreased parasitic load may comprise fewer than 1 parasite per 100 host organisms. In an aspect, a decreased parasitic load may comprise fewer than 20 parasites per 1000 host organisms. In an aspect, a decreased parasitic load may comprise fewer than 15 parasites per 1000 host organisms. In an aspect, a decreased parasitic load may comprise fewer than 10 parasites per 1000 host organisms. In an aspect, a decreased parasitic load may comprise fewer than 5 parasites per 1000 host organisms. In an aspect, a decreased parasitic load may comprise fewer than 4 parasites per 1000 host organisms. In an aspect, a decreased parasitic load may comprise fewer than 3 parasites per 1000 host organisms. In an aspect, a decreased parasitic load may comprise fewer than 2 parasites per 1000 host organisms. In an aspect, a decreased parasitic load may comprise fewer than 1 parasite per 1000 host organisms.

In aspects according to the present disclosure, a colony of host organisms has an initial parasite load, prior to being provided a source of an effective amount of a nucleic acid. In an aspect, an initial parasite load may comprise fewer than 20 parasites per 100 host organisms. In an aspect, an initial parasite load may comprise fewer than 15 parasites per 100 host organisms. In an aspect, an initial parasite load may comprise fewer than 10 parasites per 100 host organisms. In an aspect, an initial parasite load may comprise fewer than 5 parasites per 100 host organisms. In an aspect, an initial parasite load may comprise fewer than 4 parasites per 100 host organisms. In an aspect, an initial parasite load may comprise fewer than 3 parasites per 100 host organisms. In an aspect, an initial parasite load may comprise fewer than 2 parasites per 100 host organisms. In an aspect, an initial parasite load may comprise fewer than 1 parasite per 100 host organisms.

In aspects according to the present disclosure, an effective amount may be provided periodically or continually. In an aspect, an effective amount of an anti-parasitic, anti-pest or insecticidal nucleic acid composition may be provided once, twice or three times a day. In other aspects, an effective amount of an anti-parasitic, anti-pest or insecticidal nucleic acid composition may be provided once a day. In another aspect, an effective amount of an anti-parasitic, anti-pest or insecticidal nucleic acid composition may be provided one or more times every other day. In an aspect, an effective amount of an anti-parasitic, anti-pest or insecticidal nucleic acid composition may be provided every two days, every three days, or once a week. In an aspect, an effective amount of an anti-parasitic, anti-pest or insecticidal nucleic acid composition may be provided every two weeks. In an aspect, an effective amount of an anti-parasitic, anti-pest or insecticidal nucleic acid composition may be provided every three weeks. In an aspect, an effective amount of an anti-parasitic, anti-pest or insecticidal nucleic acid composition may be provided once a month. In an aspect, an effective amount of an anti-parasitic, anti-pest or insecticidal nucleic acid composition may be provided every two months. In an aspect, an effective amount of a nucleic acid composition may be provided continuously to an organism in need, for example by providing a continuous source of food. In one aspect, an effective amount of a nucleic acid composition may be provided continuously as a bee-ingestible composition. In aspects according to the present disclosure the parasite is *Varroa destructor* and the host is the honey bee, *Apis mellifera*. In aspects according to the present disclosure, an anti-parasitic, anti-pest or insecticidal nucleic acid may be a dsRNA.

In aspects according to the present disclosure, the parasitic load may decrease over a period of time. In an aspect, the time period necessary for a parasitic load decrease may be 15 weeks. In another aspect, the time period for a parasitic load decrease may be 12 weeks. In an aspect, the parasitic load decrease occurs of a period of 10 weeks. In an aspect, the time period necessary for a parasitic load decrease may be 5 weeks. In another aspect, the time period for a parasitic load decrease may be 2 weeks. In an aspect, the parasitic load decrease occurs of a period of 1 weeks. In some aspects, the parasitic load may decrease after one day, two days or three days.

The present disclosure provides for methods of reducing the parasitation of a honey bee colony comprising providing a bee colony an effective amount of an anti-parasitic, anti-pest or insecticidal nucleic acid composition. An effective amount of a composition of the present disclosure results in a reduction of parasitation over a period of time. In an aspect, a reduction of parasitation may measured within one day of providing an effective amount of an anti-parasitic, anti-pest or insecticidal nucleic acid composition. In an aspect, the reduction of parasitation may be measured after two days. In an aspect, the reduction of parasitation may be measured after 3 days. In other aspects, the reduction of parasitation may be measured after 5 days or after 1 week. In another aspect, the reduction of parasitation may be measured more than one time, for example every 3 days, every 5 days, every week or once a month. In certain aspects, according to the present disclosure, a reduction of parasitation may be measured and compared to an untreated control organism or colony.

In aspects according to the present disclosure, a reduction of parasitation after a period of time means a decrease in the total number of parasites. In an aspect, the number of parasites may decrease by 10%, 20%, 30% or more between measurements. In another aspect, the number of parasites may decrease by 40% or more between measurements. In another aspect, the number of parasites may decrease by 50% or more between measurements. In another aspect, the number of parasites may decrease by 60% or more between measurements. In another aspect, the number of parasites may decrease by 70% or more between measurements. In another aspect, the number of parasites may decrease by 80% or more between measurements. In another aspect, the number of parasites may decrease by 90% or more between measurements.

In other aspects, reduction of parasitation may be measured as the average number of parasites per host organism. In an aspect, a reduction of parasitation may comprise fewer than 20 parasites per 100 host organisms. In an aspect, a reduction of parasitation may comprise fewer than 15 parasites per 100 host organisms. In an aspect, a reduction of parasitation may comprise fewer than 10 parasites per 100 host organisms. In an aspect, a reduction of parasitation may comprise fewer than 5 parasites per 100 host organisms. In an aspect, a reduction of parasitation may comprise fewer than 4 parasites per 100 host organisms. In an aspect, a reduction of parasitation may comprise fewer than 3 parasites per 100 host organisms. In an aspect, a reduction of parasitation may comprise fewer than 2 parasites per 100 host organisms. In an aspect, a reduction of parasitation may comprise fewer than 1 parasite per 100 host organisms.

In aspects according to the present disclosure, an effective amount of an anti-parasitic, anti-pest or insecticidal nucleic acid resulting in a reduction of parasitation may be provided periodically or continually. In an aspect, an effective amount of a nucleic acid composition may be provided once, twice or three times a day. In other aspects, an effective amount of an anti-parasitic, anti-pest or insecticidal nucleic acid composition may be provided once a day. In another aspect, an effective amount of an anti-parasitic, anti-pest or insecticidal nucleic acid composition may be provided one or more times every other day. In an aspect, an effective amount of an anti-parasitic, anti-pest or insecticidal nucleic acid composition may be provided provide every two days, every three days, or once a week. In an aspect, an effective amount of an anti-parasitic, anti-pest or insecticidal nucleic acid composition may be provided continuously to an organism in need, for example by providing a continuous source of food. In one aspect, an effective amount of an anti-parasitic, anti-pest or insecticidal nucleic acid composition may be provided continuously as a bee-ingestible composition. In aspects according to the present disclosure the parasite is *Varroa destructor* and the host is the honey bee, *Apis mellifera*. In aspects according to the present disclosure, an anti-parasitic, anti-pest or insecticidal nucleic acid may be a dsRNA.

In aspects according to the present disclosure, the reduction of parasitation may decrease over a period of time. In an aspect, the time period necessary for a reduction of parasitation may be 15 weeks. In another aspect, the time period for a reduction of parasitation may be 12 weeks. In an aspect, the reduction of parasitation occurs of a period of 10 weeks. In an aspect, the time period necessary for a reduction of parasitation may be 5 weeks. In another aspect, the time period for a reduction of parasitation may be 2 weeks. In an aspect, the reduction of parasitation occurs of a period of 1 weeks. In some aspects, the reduction of parasitation may occur after one day, two days or three days.

In aspects according to the present disclosure, a reduction of parasitation is measured by the number of surviving parasites as compared to an initial measurement of the number of parasites in a colony of host organisms. In an aspect, the parasite may be a *Varroa destructor* mite and the host may be a honey bee, *Apis mellifera*. In an aspect, the number of surviving parasites may be 25% of the initial number of parasites. In an aspect, the number of surviving parasites may be 15% of the initial number of parasites. In an aspect, the number of surviving parasites may be 10% of the initial number of parasites. In an aspect, the number of surviving parasites may be 5% of the initial number of parasites. In an aspect the number of surviving parasites may be less than 5% or even undetectable after providing a host colony an effective amount of an anti-parasitic, anti-pest or insecticidal nucleic acid composition.

In an aspect, the present disclosure provides for methods and compositions for reducing the susceptibility of bees to *Varroa* mite infestation. In other aspects, the present disclosure provides for methods and compositions to prevent the infestation of colonies of bees. In another aspect, the present disclosure provides methods and compositions for reducing the parasitation of honeybees by the mite *Varroa destructor*.

According to the present disclosure, a host organism provided with a source of an anti-parasitic, anti-pest or insecticidal nucleic acid, can accumulate nucleic acid in the host body, usually the hemolymph. By harboring nucleic acid, such host organisms become resistant, or less susceptible to parasitation. In other aspects, a colony of host organisms, provided with a source of nucleic acid, can accumulate nucleic acid in the host body of multiple members of the colony, thereby providing resistance or decreased susceptibility to a parasite. nucleic acid found in host organisms provided with a source of nucleic acid, can be detected using methods known to those of ordinary skill in the art. In aspects according to the present disclosure, an anti-parasitic, anti-pest or insecticidal nucleic acid may be a dsRNA.

In an aspect of the present disclosure, methods and compositions for treating *Varroa* mite infestations in bees by down-regulating calmodulin and calmodulin related *Varroa* mite gene products, are provided. In an aspect, the compositions comprise an anti-parasitic, anti-pest or insecticidal nucleic acid corresponding to the *Varroa destructor* calmodulin sequence of SEQ ID NO: 1. In an aspect, the compositions comprise an anti-parasitic, anti-pest or insecticidal nucleic acid corresponding to the *Varroa destructor* calmodulin sequence of SEQ ID NO: 2. In an aspect, the compositions comprise an anti-parasitic, anti-pest or insecticidal nucleic acid corresponding to the *Varroa destructor* calmodulin sequence of SEQ ID NO: 69. In an aspect, the compositions comprise an anti-parasitic, anti-pest or insecticidal nucleic acid corresponding to the *Varroa destructor* calmodulin sequence of SEQ ID NO: 70. In some aspects, the compositions comprise an anti-parasitic, anti-pest or insecticidal nucleic acid corresponding to a *Varroa destructor* calmodulin sequence selected from SEQ ID NOs: 71-87. In another aspect, the compositions comprise an anti-parasitic, anti-pest or insecticidal nucleic acid corresponding to a sequence selected from SEQ ID NOs: 3, 4, and 88-93. In an aspect, the compositions comprise a small RNA corresponding to the *Varroa destructor* calmodulin sequence of SEQ ID NO: 1. In an aspect, the compositions comprise a small RNA corresponding to the *Varroa destructor* calmodulin sequence of SEQ ID NO: 2. In an aspect, the compositions comprise a small RNA corresponding to the *Varroa destructor* calmodulin sequence of SEQ ID NO: 69. In an aspect, the compositions comprise a small RNA corresponding to the *Varroa destructor* calmodulin sequence of SEQ ID NO: 70. In some aspects, the compositions comprise a small RNA corresponding to a *Varroa destructor* calmodulin sequence selected from SEQ ID NOs: 71-87. In another aspect, the compositions comprise a small RNA corresponding to a *Varroa destructor* calmodulin sequence selected from SEQ ID NOs: 3, 4, 88 and 89. In another aspect, the compositions comprise a small RNA corresponding to a sequence selected from SEQ ID NOs: 90-93. In an aspect, the compositions comprise a dsRNA corresponding to the *Varroa destructor* calmodulin sequence of SEQ ID NO: 1. In an aspect, the compositions comprise a dsRNA corresponding to the *Varroa destructor* calmodulin sequence of SEQ ID NO: 2. In an aspect, the compositions comprise a dsRNA corresponding to the *Varroa destructor* calmodulin sequence of SEQ ID NO: 69. In an aspect, the compositions comprise a dsRNA corresponding to the *Varroa destructor* calmodulin sequence of SEQ ID NO: 70. In some aspects, the compositions comprise a dsRNA corresponding to a *Varroa destructor* calmodulin sequence selected from SEQ ID NOs: 71-87. In another aspect, the compositions comprise a dsRNA corresponding to a *Varroa destructor* calmodulin sequence selected from SEQ ID NOs: 3, 4, 88 and 89. In another aspect, the compositions comprise a dsRNA comprising a sequence selected from SEQ ID NOs:90-93. In an aspect, the compositions comprise an siRNA corresponding to the *Varroa destructor* calmodulin sequence of SEQ ID NO: 1. In an aspect, the compositions comprise a siRNA corresponding to the *Varroa destructor* calmodulin sequence of SEQ ID NO: 2. In an aspect, the compositions comprise a siRNA corresponding to the *Varroa destructor* calmodulin sequence of SEQ ID NO: 69. In an aspect, the compositions comprise a siRNA corresponding to the *Varroa destructor* calmodulin sequence of SEQ ID NO: 70. In some aspects, the compositions comprise a siRNA corresponding to a *Varroa destructor* calmodulin sequence selected from SEQ ID NOs: 71-87. In another aspect, the compositions comprise a siRNA corresponding to a *Varroa destructor* calmodulin sequence selected from SEQ ID NOs: 3, 4, 88 and 89. In another aspect, the compositions comprise a siRNA corresponding to a sequence selected from SEQ ID NOs: 90-93. In aspects according to the present disclosure the composition may comprise an anti-parasitic, anti-pest or insecticidal nucleic acid corresponding to a region of SEQ ID NO: 1 or 2. In other aspects according to the present disclosure the composition may comprise an anti-parasitic, anti-pest or insecticidal nucleic acid corresponding to a region of SEQ ID NO: 69 or 70. In yet other aspects according to the present disclosure the composition may comprise a nucleic acid corresponding to a region of a sequence selected from SEQ ID NOs: 3, 4, 88 and 89. In yet other aspects according to the present disclosure the composition may comprise a nucleic acid corresponding to a region of a sequence selected from SEQ ID NOs: 90-94.

*Varroa* mites parasitize pupae and adult bees and reproduce in the pupal brood cells. The mites use their mouths to puncture the exoskeleton and feed on the bee's hemolymph. The present inventors unexpectedly found that polynucleotide agents administered to the bees to treat *Varroa* mite infestations presented in the bee's hemolymph thereby becoming available to the mite.

Figure 2:
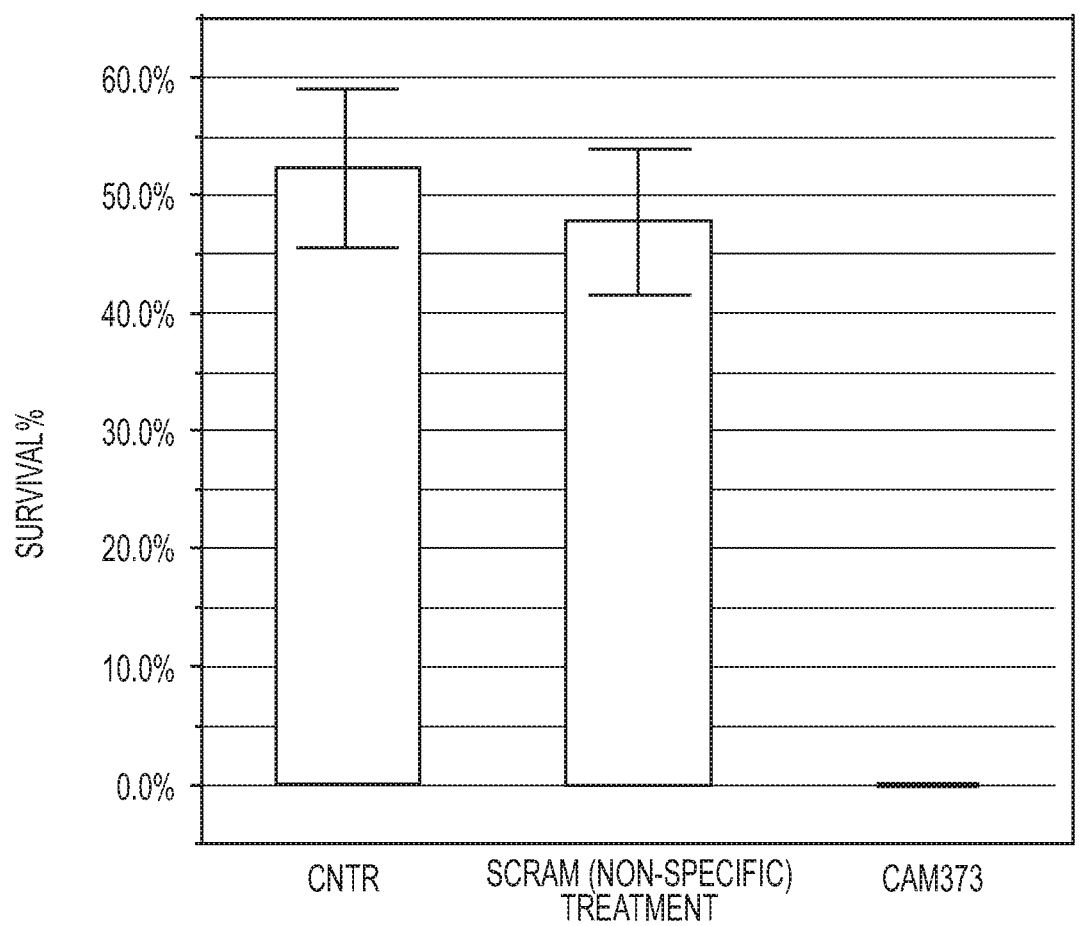
FIG. 2 presents the survival rate of mites exposed to a nucleic acid comprising a sequence identical or complementary to SEQ ID NO: 3 (CAM373) in a direct feeding bioassay at 3 day post treatment relative to a non treated control (CNTR) or a non-specific sequence (SCRAM, SEQ ID NO: 5).
Figure 3A:
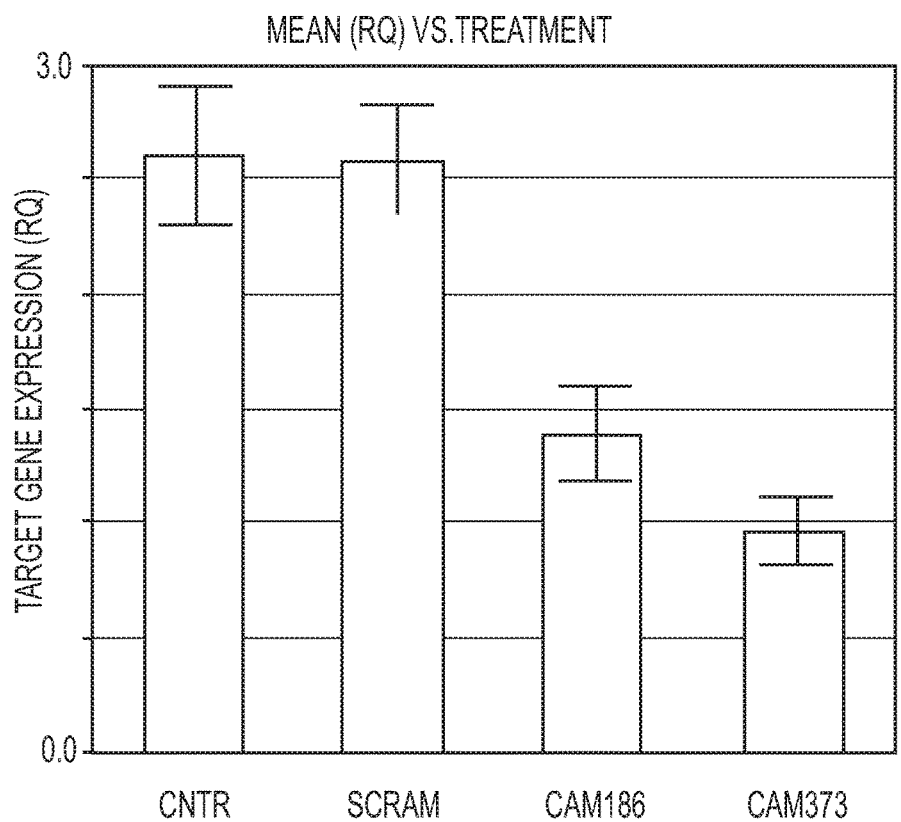
FIG. 3 Panel A presents a gene expression analysis at five day post treatment with a nucleic acid comprising a sequence identical or complementary to SEQ ID NO: 3 (CAM373) or a nucleic acid comprising a sequence identical or complementary to SEQ ID NO: 4 (CAM186) relative to controls. Panel B shows the survival rate of mites exposed to nucleic acids comprising a sequence identical or complementary to SEQ ID NOS: 3 (CAM373) or 4 (CAM186) relative to controls.
Figure 3B:
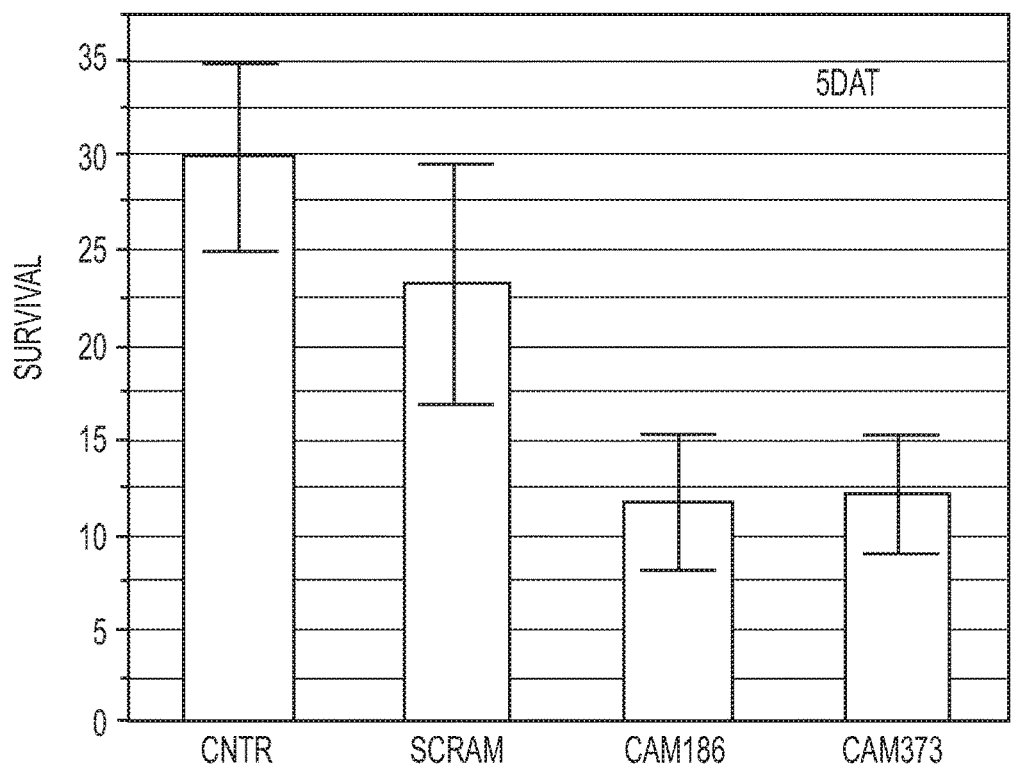

The present inventors have shown that calmodulin-targeting dsRNA fragments can successfully be transferred to *Varroa* mites (see, e.g., FIG. 2), that the dsRNA can serve to down-regulate expression of calmodulin genes in the *Varroa* mite (see, e.g., FIG. 3 Panel A) and further that targeting of calmodulin genes for down-regulation can result in a reduction in the number of *Varroa* mites (see, e.g., FIG. 3 Panel B).

Thus, according to one aspect of the present disclosure there is provided a method of preventing or treating a *Varroa destructor* mite infestation of a bee, the method comprising administering to the bee an effective amount of a nucleic acid agent comprising a nucleic acid sequence which down-regulates expression of a calmodulin gene of a *Varroa destructor* mite, thereby preventing or treating a *Varroa destructor* mite infestation of a bee.

According to this aspect of the present disclosure the agents of the present disclosure are used to prevent the *Varroa destructor* mite from living as a parasite on the bee, or larvae thereof. The phrase "*Varroa destructor* mite" refers to the external parasitic mite that attacks honey bees *Apis cerana* and *Apis mellifera*. The mite may be at an adult stage, feeding off the bee, or at a larval stage, inside the honey bee brood cell.

As mentioned, the agents of the present disclosure are capable of selectively down-regulating expression of a gene product of a *Varroa destructor* mite. As used herein, the phrase "gene product" refers to an RNA molecule or a protein. According to one aspect, the *Varroa destructor* mite gene product is one which is essential for mite viability. Down-regulation of such a gene product would typically result in killing of the *Varroa* mite. According to another aspect, the *Varroa destructor* mite gene product is one which is essential for mite reproduction. Down-regulation of such a gene product would typically result in the prevention of reproduction of the *Varroa* mite and the eventual extermination of the mite population. According to yet another aspect, the *Varroa destructor* mite gene product is one which is required to generate pathogenic symptoms in the bee. In some aspects, the *Varroa destructor* gene product is a calmodulin gene. In certain aspects, the calmodulin gene may comprise a nucleic acid sequence according to SEQ ID NO: 1 or SEQ ID NO: 2. In certain aspects, the calmodulin gene may comprise a nucleic acid sequence according to SEQ ID NO: 69 or SEQ ID NO: 70.

Examples of gene products that may be down-regulated according to this aspect of the present disclosure include, but are not limited to a calmodulin gene.

In an aspect according to the present disclosure, agents capable of down-regulating expression of a gene product of a *Varroa destructor* mite or other parasite, may downregulate to a lesser extent expression of the gene product in other animals, such as the bee or other non-target organism. Accordingly, certain agents of the present disclosure are able to distinguish between the mite gene and the bee gene, down-regulating the former to a greater extent than the latter. In some aspects, certain agents of the present disclosure are able to distinguish between the target gene in the target organism and orthologs in non-target organisms, down-regulating the former to a greater extent than the latter. In other aspects, the target gene of the parasite is downregulated while the homologous host gene is not. In yet another aspect, the target gene of the parasite does not have a homologue in the host. According to another aspect the agents of the present disclosure do not down-regulate the bee gene whatsoever. For example, this may be effected by targeting a gene that is expressed differentially in the mite and not in the bee e.g. the mite sodium channel gene—FJ216963. Alternatively, the agents of the present disclosure may be targeted to mite-specific sequences of a gene that is expressed both in the mite and in the bee.

According to one aspect, the agents of the present disclosure target segments of *Varroa* genes that are at least 100 bases long and do not carry any sequence longer than 5 bases that is entirely homologous to any bee-genome sequence or human-genome sequence. According to one aspect, the agents of the present disclosure target segments of *Varroa* genes that are at least 100 bases long and do not carry any sequence longer than 6 bases that is entirely homologous to any bee-genome sequence or human-genome sequence. According to one aspect, the agents of the present disclosure target segments of *Varroa* genes that are at least 100 bases long and do not carry any sequence longer than 7 bases that is entirely homologous to any bee-genome sequence or human-genome sequence. According to one aspect, the agents of the present disclosure target segments of *Varroa* genes that are at least 100 bases long and do not carry any sequence longer than 8 bases that is entirely homologous to any bee-genome sequence or human-genome sequence. According to one aspect, the agents of the present disclosure target segments of *Varroa* genes that are at least 100 bases long and do not carry any sequence longer than 9 bases that is entirely homologous to any bee-genome sequence or human-genome sequence. According to one aspect, the agents of the present disclosure target segments of *Varroa* genes that are at least 100 bases long and do not carry any sequence longer than 10 bases that is entirely homologous to any bee-genome sequence or human-genome sequence. According to one aspect, the agents of the present disclosure target segments of *Varroa* genes that are at least 100 bases long and do not carry any sequence longer than 11 bases that is entirely homologous to any bee-genome sequence or human-genome sequence. According to one aspect, the agents of the present disclosure target segments of *Varroa* genes that are at least 100 bases long and do not carry any sequence longer than 12 bases that is entirely homologous to any bee-genome sequence or human-genome sequence. According to one aspect, the agents of the present disclosure target segments of *Varroa* genes that are at least 100 bases long and do not carry any sequence longer than 13 bases that is entirely homologous to any bee-genome sequence or human-genome sequence. According to one aspect, the agents of the present disclosure target segments of *Varroa* genes that are at least 100 bases long and do not carry any sequence longer than 14 bases that is entirely homologous to any bee-genome sequence or human-genome sequence. According to one aspect, the agents of the present disclosure target segments of *Varroa* genes that are at least 100 bases long and do not carry any sequence longer than 15 bases that is entirely homologous to any bee-genome sequence or human-genome sequence. According to one aspect, the agents of the present disclosure target segments of *Varroa* genes that are at least 100 bases long and do not carry any sequence longer than 16 bases that is entirely homologous to any bee-genome sequence or human-genome sequence. According to one aspect, the agents of the present disclosure target segments of *Varroa* genes that are at least 100 bases long and do not carry any sequence longer than 17 bases that is entirely homologous to any bee-genome sequence or human-genome sequence. According to one aspect, the agents of the present disclosure target segments of *Varroa* genes that are at least 100 bases long and do not carry any sequence longer than 18 bases that is entirely homologous to any bee-genome sequence or human-genome sequence. According to one aspect, the agents of the present disclosure target segments of *Varroa* genes that are at least 100 bases long and do not carry any sequence longer than 19 bases that is entirely homologous to any bee-genome sequence or human-genome sequence. According to one aspect, the agents of the present disclosure target segments of *Varroa* genes that are at least 100 bases long and do not carry any sequence longer than 20 bases that is entirely homologous to any bee-genome sequence or human-genome sequence. According to one aspect, the agents of the present disclosure target segments of *Varroa* genes that are at least 100 bases long and do not carry any sequence longer than 21 bases that is entirely homologous to any bee-genome sequence or human-genome sequence. According to one aspect, the agents of the present disclosure target segments of *Varroa* genes that are at least 100 bases long and do not carry any sequence longer than 22 bases that is entirely homologous to any bee-genome sequence or human-genome sequence. According to one aspect, the agents of the present disclosure target segments of *Varroa* genes that are at least 100 bases long and do not carry any sequence longer than 23 bases that is entirely homologous to any bee-genome sequence or human-genome sequence. According to one aspect, the agents of the present disclosure target segments of *Varroa* genes that are at least 100 bases long and do not carry any sequence longer than 24 bases that is entirely homologous to any bee-genome sequence or human-genome sequence. According to one aspect, the agents of the present disclosure target segments of *Varroa* genes that are at least 100 bases long and do not carry any sequence longer than 25 bases that is entirely homologous to any bee-genome sequence or human-genome sequence. According to one aspect, the agents of the present disclosure target segments of *Varroa* genes that are at least 100 bases long and do not carry any sequence longer than 26 bases that is entirely homologous to any bee-genome sequence or human-genome sequence. According to one aspect, the agents of the present disclosure target segments of *Varroa* genes that are at least 100 bases long and do not carry any sequence longer than 27 bases that is entirely homologous to any bee-genome sequence or human-genome sequence. According to one aspect, the agents of the present disclosure target segments of *Varroa* genes that are at least 100 bases long and do not carry any sequence longer than 28 bases that is entirely homologous to any bee-genome sequence or human-genome sequence. According to one aspect, the agents of the present disclosure target segments of *Varroa* genes that are at least 100 bases long and do not carry any sequence longer than 29 bases that is entirely homologous to any bee-genome sequence or human-genome sequence. According to one aspect, the agents of the present disclosure target segments of *Varroa* genes that are at least 100 bases long and do not carry any sequence longer than 30 bases that is entirely homologous to any bee-genome sequence or human-genome sequence. While it will be appreciated that more than one gene may be targeted in order to maximize the cytotoxic effect on the *Varroa* mites, compositions that comprise one, or a few, small RNA's would increase the probability of being a selective insecticide composition as cross reactivity with other insects may be reduced.

According to one aspect, a dsRNA composition can be prepared corresponding to the *Varroa destructor* Calmodulin-1 and Calmodulin-2 genes (e.g. using nucleic acid agents having the sequence as set forth in SEQ ID NOs: 1 to 4, and 69 to 89, their complements or nucleic acids directed to regions thereof).

It will be appreciated that as well as down-regulating a number of genes, the present disclosure further provides for, and includes, using a number of agents to down-regulate the same gene (e.g. a number of nucleic acids, or dsRNAs, each hybridizing to a different segment of the same gene). For example, in an aspect a combination of one or more nucleic acids corresponding to a sequence selected from the group consisting of SEQ ID NOs: 1 to 4, 6, 23, 26 to 35, and 69 to 89 may be used to increase the cytotoxic and anti-parasitic effects of the composition. Tools which are capable of identifying species-specific sequences may be used for this purpose—e.g. BLASTN and other such computer programs. U.S. Patent Publication NOs. 20090118214 and 20120108497 provide for the use of dsRNA for preventing and treating viral infections in honeybees. U.S. Patent Publication Nos. 20120258646 provides for the use of dsRNA to control *Varroa destructor* in honeybee. Each publication is hereby incorporated in their entireties.

The present disclosure provides for, and includes, compositions and methods for down-regulating the expression of a gene in a target organism. In an aspect the target organism may be a parasite. In certain aspects, the parasite may be *Varroa destructor*. As used herein, the term "down-regulating expression" refers to causing, directly or indirectly, reduction in the transcription of a desired gene, reduction in the amount, stability or translatability of transcription products (e.g. RNA) of the gene, and/or reduction in translation of the polypeptide(s) encoded by the desired gene. Down-regulating expression of a gene product of a *Varroa destructor* mite can be monitored, for example, by direct detection of gene transcripts (for example, by PCR), by detection of polypeptide(s) encoded by the gene or bee pathogen RNA (for example, by Western blot or immunoprecipitation), by detection of biological activity of polypeptides encode by the gene (for example, catalytic activity, ligand binding, and the like), or by monitoring changes in the *Varroa destructor* mite (for example, reduced proliferation of the mite, reduced virulence of the mite, reduced motility of the mite etc) and by testing bee infectivity/pathogenicity.

Downregulation of a pest or parasite gene product can be effected on the genomic and/or the transcript level using a variety of agents which interfere with transcription and/or translation (e.g., RNA silencing agents, Ribozyme, DNAzyme and antisense nucleic acid molecules). Down-regulation of a *Varroa destructor* mite gene product can be effected on the genomic and/or the transcript level using a variety of agents which interfere with transcription and/or translation (e.g., RNA silencing agents, Ribozyme, DNAzyme and antisense nucleic acid molecules).

According to one aspect, the agent which down-regulates expression of a pest or parasite gene product is a small RNA, such as an RNA silencing agent. According to this aspect, the small RNA is greater than 15 base pairs in length. In another aspect, the small RNA is greater than 50 base pairs in length. In an aspect, the small RNA is greater than 50 base pairs in length but less than about 500 base pairs. In an aspect, the small RNA is greater than 100 base pairs in length but less than about 500 base pairs. In an aspect, the small RNA is greater than 200 base pairs in length but less than about 500 base pairs. In an aspect, the pest or parasite may be a *Varroa destructor* mite.

Another method of down-regulating a pest or parasite gene product is by introduction of small inhibitory RNAs (siRNAs). Another method of down-regulating a *Varroa* mite gene product is by introduction of small inhibitory RNAs (siRNAs).

In one aspect of the present disclosure, synthesis of RNA silencing agents suitable for use with the present disclosure can be effected as follows. First, the pest or parasite target mRNA is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex (Tuschl ChemBiochem. 2:239-245). It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (available on the internet at www.ambion.com/techlib/tn/91/912.html).

Second, potential target sites are compared to an appropriate genomic database of non-target organisms (e.g., human, bee, monarch butterfly, mouse, rat etc.) using any sequence alignment software, such as the BLAST software available from the NCBI server (available on the internet at www.ncbi.nlm.nih.gov/BLAST/). In some embodiments, Putative target sites which exhibit significant homology to other coding sequences are filtered out. In some embodiments, one or more nucleotides are changed or deleted compared to the target sequence to disrupt sequences having 5, 6, 7, 8, 9, 10, 11, 12, 13, 14, 15, 16, 17, 18, 19, 20, 21, 22, 23, 24, 25 or more contiguous nucleotides that are 100% identical or complementary to a gene sequence of a non-target organism.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene or sequence for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene or pest or parasite target sequence. An example of a scrambled nucleotide sequence is provided at SEQ ID NO. 5.

For example, a siRNA that may be used in this aspect of the present disclosure is one which targets a mite-specific calmodulin gene. Examples of siRNAs are provided in SEQ ID NOs: 3, 4, 88 and 89.

It will be appreciated that the RNA silencing agent of the present disclosure need not be limited to those molecules containing only RNA, but further encompasses chemically-modified nucleotides and non-nucleotides.

In some aspects, the RNA silencing agent provided herein can be functionally associated with a cell-penetrating peptide. As used herein, a "cell-penetrating peptide" is a peptide that comprises a short (about 12-residues) amino acid sequence or functional motif that confers the energy-independent (i.e., non-endocytotic) translocation properties associated with transport of the membrane-permeable complex across the plasma and/or nuclear membranes of a cell. The cell-penetrating peptide used in the membrane-permeable complex of the present disclosure preferably comprises at least one non-functional cysteine residue, which is either free or derivatized to form a disulfide link with a double-stranded ribonucleic acid that has been modified for such linkage. Representative amino acid motifs conferring such properties are listed in U.S. Pat. No. 6,348,185, the contents of which are expressly incorporated herein by reference. The cell-penetrating peptides of the present disclosure preferably include, but are not limited to, penetratin, transportan, plsl, TAT(48-60), pVEC, MTS, and MAP.

Another agent capable of down-regulating a pest or parasite gene product is a DNAzyme molecule capable of specifically cleaving an mRNA transcript or DNA sequence of the bee pathogen polypeptide. DNAzymes are single-stranded polynucleotides which are capable of cleaving both single and double stranded target sequences (Breaker, R. R. and Joyce, G. Chemistry and Biology 1995; 2:655; Santoro, S. W. & Joyce, G. F. Proc. Natl, Acad. Sci. USA 1997; 943:4262) A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro, S. W. & Joyce, G. F. Proc. Natl, Acad. Sci. USA 199; for a review of DNAzymes, see Khachigian, L M, Curr Opin Mol Ther 4:119-21 (2002)). In an aspect, the pest or parasite gene product may be a *Varroa* mite gene product. Downregulation of pest or parasite gene products can also be effected by using an antisense polynucleotide capable of specifically hybridizing with an mRNA transcript encoding the pest or parasite gene product. Design of antisense molecules which can be used to efficiently downregulate a pest or parasite gene product must be effected while considering two aspects important to the antisense approach. The first aspect is delivery of the oligonucleotide into the cytoplasm of the appropriate cells, while the second aspect is design of an oligonucleotide which specifically binds the designated mRNA or RNA target sequence within cells in a way which inhibits translation thereof. In an aspect, the pest or parasite gene product may be a *Varroa* mite gene product. In another aspect, the pest or parasite gene product may be calmodulin gene product.

A number of delivery strategies which can be used to efficiently deliver oligonucleotides into a wide variety of cell types (see, for example, Luft J Mol Med 76: 75-6 (1998); Kronenwett et al. Blood 91: 852-62 (1998); Rajur et al. Bioconjug Chem 8: 935-40 (1997); Lavigne et al. Biochem Biophys Res Commun 237: 566-71 (1997) and Aoki et al. (1997) Biochem Biophys Res Commun 231: 540-5 (1997)).

In addition, algorithms for identifying those sequences with the highest predicted binding affinity for their target mRNA based on a thermodynamic cycle that accounts for the energetics of structural alterations in both the target mRNA and the oligonucleotide are also available (see, for example, Walton et al. Biotechnol Bioeng 65: 1-9 (1999)). Such algorithms have been successfully used to implement an antisense approach in cells. For example, the algorithm developed by Walton et al. enabled scientists to successfully design antisense oligonucleotides for rabbit beta-globin (RBG) and mouse tumor necrosis factor-alpha (TNF alpha) transcripts. The same research group has more recently reported that the antisense activity of rationally selected oligonucleotides against three model target mRNAs (human lactate dehydrogenase A and B and rat gpl) in cell culture as evaluated by a kinetic PCR technique proved effective in almost all cases, including tests against three different targets in two cell types with phosphodiester and phosphorothioate oligonucleotide chemistries. In addition, several approaches for designing and predicting efficiency of specific oligonucleotides using an in vitro system were also published (Matveeva et al., Nature Biotechnology 16: 1374-1375 (1998)].

Another agent capable of down-regulating a pest or parasite gene product is a ribozyme molecule capable of specifically cleaving an mRNA transcript encoding the *Varroa* mite gene product. Ribozymes are being increasingly used for the sequence-specific inhibition of gene expression by the cleavage of mRNAs encoding proteins of interest (Welch et al., Curr Opin Biotechnol. 9:486-96 (1998)). The possibility of designing ribozymes to cleave any specific target RNA, including viral RNA, has rendered them valuable tools in both basic research and therapeutic applications. In an aspect, the pest or parasite gene product may be a *Varroa* mite gene product. In another aspect, the pest or parasite gene product may be calmodulin gene product.

An additional method of down-regulating the expression of a pest or parasite gene product in cells is via triplex forming oligonucleotides (TFOs). Recent studies have shown that TFOs can be designed which can recognize and bind to polypurine/polypyrimidine regions in double-stranded helical DNA in a sequence-specific manner. These recognition rules are outlined by Maher III, L. J., et al., Science (1989) 245:725-7; Moser, H. E., et al., Science, (1987) 238:645-6; Beal, P. A., et al., Science (1992) 251: 1360-1363; Cooney, M., et al., Science (1988) 241:456-459; and Hogan, M. E., et al., EP Publication 375408. Modification of the oligonucleotides, such as the introduction of intercalators and backbone substitutions, and optimization of binding conditions (pH and cation concentration) have aided in overcoming inherent obstacles to TFO activity such as charge repulsion and instability, and it was recently shown that synthetic oligonucleotides can be targeted to specific sequences (for a recent review see Seidman and Glazer, J Clin Invest 2003; 112:487-94). In an aspect, the pest or parasite gene product may be a *Varroa* mite gene product. In another aspect, the pest or parasite gene product may be calmodulin gene product.

In general, the triplex-forming oligonucleotide has the sequence correspondence:

| oligo  | 3'--A | G | G | T |
|--------|-------|---|---|---|
| duplex | 5'--A | G | C | T |
| duplex | 3'--T | C | G | A |

However, it has been shown that the A-AT and G-GC triplets have the greatest triple helical stability (Reither and Jeltsch, BMC Biochem, 2002, Sep. 12, Epub). The same authors have demonstrated that TFOs designed according to the A-AT and G-GC rule do not form non-specific triplexes, indicating that the triplex formation is indeed sequence specific.

Triplex-forming oligonucleotides preferably are at least 15, more preferably 25, still more preferably or more nucleotides in length, up to 50 or 100 bp.

Transfection of cells (for example, via cationic liposomes) with TFOs, and formation of the triple helical structure with the target DNA induces steric and functional changes, blocking transcription initiation and elongation, allowing the introduction of desired sequence changes in the endogenous DNA and resulting in the specific downregulation of gene expression.

Detailed description of the design, synthesis and administration of effective TFOs can be found in U.S. Patent Publication Nos. 2003/017068 and 2003/0096980 to Froehler et al., and 2002/0128218 and 2002/0123476 to Emanuele et al., and U.S. Pat. No. 5,721,138 to Lawn.

The polynucleotide down-regulating agents of the present disclosure may be generated according to any polynucleotide synthesis method known in the art such as enzymatic synthesis or solid phase synthesis. Equipment and reagents for executing solid-phase synthesis are commercially available from, for example, Applied Biosystems. Any other means for such synthesis may also be employed; the actual synthesis of the polynucleotides is well within the capabilities of one skilled in the art and can be accomplished via established methodologies as detailed in, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988) and "Oligonucleotide Synthesis" Gait, M. J., ed. (1984) utilizing solid phase chemistry, e.g. cyanoethyl phosphoramidite followed by deprotection, desalting and purification by for example, an automated trityl-on method or HPLC.

The polynucleotide agents of the present disclosure may comprise heterocylic nucleosides consisting of purines and the pyrimidines bases, bonded in a 3' to 5' 5phosphodiester linkage.

Preferably used polynucleotide agents are those modified in either backbone, internucleoside linkages or bases, as is broadly described hereinunder.

Specific examples of polynucleotide agents useful according to this aspect of the present disclosure include polynucleotide agents containing modified backbones or non-natural internucleoside linkages. Polynucleotide agents having modified backbones include those that retain a phosphorus atom in the backbone, as disclosed in U.S. Pat. Nos. 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Modified polynucleotide backbones include, for example, phosphorothioates, chiral phosphorothioates, phosphorodithioates, phosphotriesters, aminoalkyl phosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms can also be used.

Alternatively, modified polynucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts, as disclosed in U.S. Pat. Nos. 5,034,506; 5,166,315; 5,185,444; 5,216,141; 5,235,033; 5,264,562; 5,264,564; 5,405,938; 5,470,967; 5,489,677; 5,541,307; 5,561,225; 5,596,086; 5,602,240; 5,602,240; 5,608,046; 5,610,289; 5,618,704; 5,623,070; 5,663,312; 5,214,134; 5,466,677; 5,610,289; 5,633,360; 5,677,437; and 5,677,439.

Other polynucleotide agents which can be used according to the present disclosure, are those modified in both sugar and the internucleoside linkage, i.e., the backbone, of the nucleotide units are replaced with novel groups. The base units are maintained for complementation with the appropriate polynucleotide target. An example for such an polynucleotide mimetic, includes peptide nucleic acid (PNA). A PNA polynucleotide refers to a polynucleotide where the sugar-backbone is replaced with an amide containing backbone, in particular an aminoethylglycine backbone. The bases are retained and are bound directly or indirectly to aza nitrogen atoms of the amide portion of the backbone. United States patents that teach the preparation of PNA compounds include, but are not limited to, U.S. Pat. Nos. 5,539,082; 5,714,331; and 5,719,262, each of which is herein incorporated by reference. Other backbone modifications, which can be used in the present disclosure are disclosed in U.S. Pat. No. 6,303,374.

Polynucleotide agents of the present disclosure may also include base modifications or substitutions. As used herein, "unmodified" or "natural" bases include the purine bases adenine (A) and guanine (G), and the pyrimidine bases thymine (T), cytosine (C) and uracil (U). Modified bases include but are not limited to other synthetic and natural bases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further bases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 613, and those disclosed by Sanghvi, Y. S., Chapter 15, Antisense Research and Applications, pages 289-2, Crooke, S. T. and Lebleu, B., ed., CRC Press, 1993. Such bases are particularly useful for increasing the binding affinity of the oligomeric compounds of the disclosure. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi Y S et al. (1993) Antisense Research and Applications, CRC Press, Boca Raton 276-278) and are presently preferred base substitutions, even more particularly when combined with 2'-O-methoxyethyl sugar modifications.

Following synthesis, the polynucleotide agents of the present disclosure may optionally be purified. For example, polynucleotides can be purified from a mixture by extraction with a solvent or resin, precipitation, electrophoresis, chromatography, or a combination thereof. Alternatively, polynucleotides may be used with no, or a minimum of, purification to avoid losses due to sample processing. The polynucleotides may be dried for storage or dissolved in an aqueous solution. The solution may contain buffers or salts to promote annealing, and/or stabilization of the duplex strands.

It will be appreciated that a polynucleotide agent of the present disclosure may be provided per se, or as a nucleic acid construct comprising a nucleic acid sequence encoding the polynucleotide agent. Typically, the nucleic acid construct comprises a promoter sequence which is functional in the host cell, as detailed herein below.

The polynucleotide sequences of the present disclosure, under the control of an operably linked promoter sequence, may further be flanked by additional sequences that advantageously affect its transcription and/or the stability of a resulting transcript. Such sequences are generally located upstream of the promoter and/or downstream of the 3' end of the expression construct.

The term "operably linked", as used in reference to a regulatory sequence and a structural nucleotide sequence, means that the regulatory sequence causes regulated expression of the linked structural nucleotide sequence. "Regulatory sequences" or "control elements" refer to nucleotide sequences located upstream, within, or downstream of a structural nucleotide sequence, and which influence the timing and level or amount of transcription, RNA processing or stability, or translation of the associated structural nucleotide sequence. Regulatory sequences may include promoters, translation leader sequences, introns, enhancers, stem-loop structures, repressor binding sequences, termination sequences, pausing sequences, polyadenylation recognition sequences, and the like.

It will be appreciated that the nucleic acid agents can be delivered to the pest or parasite in a great variety of ways. According to one aspect, the nucleic acid agents are delivered directly to the pest or parasite (e.g. by spraying a mite infested hive). The nucleic acid agents, or constructs encoding same may enter the mites bodies by diffusion. In this aspect, the promoter of the nucleic acid construct is typically operational in mite cells. In an aspect, the pest or parasite may be *Varroa destructor*.

It will be appreciated that since many parasites use their mouths to puncture the host arthropod exoskeleton and feed on the arthropod's hemolymph, the present disclosure contemplates delivering the polynucleotide agents of the present disclosure to the arthropod, whereby they become presented in the arthropod hemolymph thereby becoming available to the pest or parasite. Thus, according to another aspect, the nucleic acid agents are delivered indirectly to the pest or parasite (for example to a mite via a host bee). In this aspect, the promoter of the nucleic acid construct is typically operational in host cells. In certain aspects, the pest or parasite may be *Varroa destructor* and the host arthropod may be a bee.

According to one aspect, the nucleic acid agents are delivered to the infested hosts by spraying. The nucleic acid agents, or constructs encoding same may enter the host's bodies by diffusion.

In certain aspects, the pest or parasite may be *Varroa destructor* and the host arthropod may be a bee.

According to another aspect, the nucleic acid agents are delivered to the host via its food. The present inventors consider that following ingestion of the nucleic acid agents of the present disclosure, the agents can be presented, for example in a host arthropod in the host's hemolymph, whereby it becomes available to the parasite, for example a *Varroa* mite.

Thus the polynucleotides of the present disclosure may be synthesized in vitro or in vivo, for example in a bacterial or yeast cell, and added to the food. For example double stranded RNA may be synthesized by adding two opposing promoters (e.g. T7 promoters) to the ends of the gene segments, wherein the promoter is placed immediately 5' to the gene and the promoter is placed immediately 3' to the gene segment in the opposite orientation. The dsRNA may then be prepared by transcribing in vitro with the T7 RNA polymerase.

Examples of sequences for synthesizing nucleic acids, including dsRNA, according to aspects of the present disclosure are provided in SEQ ID NOs: 1 to 4, 6, 23, 26 to 35, and 69 to 93.

It will be appreciated that some pests or parasites cause wound sites in the exoskeleton of a host arthropod. Such wound sites harbor bacterial infections. For example, a host bee wound site may harbor a bacteria such as Melissococcus pluton, which causes European foulbrood. In addition, to their parasitic effects, parasites are known to act as vectors for a number of other pathogens and parasites. For example, *Varroa* mites are suspected of acting as vectors for a number of honey bee pathogens, including deformed wing virus (DWV), Kashmir bee virus (KBV), acute bee paralysis virus (ABPV) and black queen cell virus (BQCV), and may weaken the immune systems of their hosts, leaving them vulnerable to infections.

Thus, by killing the pest or parasite (or preventing reproduction thereof), the anti-parasitic, anti-pest or insecticidal agents of the present disclosure may be used to prevent and/or treat bacterial infections of host organisms. For example, Melissococcus pluton and viral infections in host bees caused by the above named viruses. Since *Varroa* mite infestation and viral infections are thought to be responsible for colony collapse disorder (CCD), the present agents may also be used to prevent or reduce the susceptibility of a bee colony to CCD.

It will be appreciated that in addition to feeding of anti-parasitic, anti-pest or insecticidal nucleic acid agents for reduction of the bee pathogen infection and infestation, enforcement of proper sanitation (for example, refraining from reuse of infested hives) can augment the effectiveness of treatment and prevention of infections.

Also included and provided for by the present disclosure are transgenic bacteria and yeast cells that express a selective insecticide. In one aspect, a nucleic acid encoding a small RNA, dsRNA, miRNA or a small or miRNA-resistant target nucleic acid molecule used herein is operably linked to a promoter and optionally a terminator. In some embodiments, the transgenic bacteria and yeast cells are killed, for example, by applying heat or pressure. In some embodiments, the transgenic bacteria and yeast cells are lysed prior to providing the selective insecticide to the target organism. In some embodiments, the transgenic bacteria and yeast cells are not lysed.

In one aspect, an exogenous nucleic acid molecule used herein is or encodes a small RNA, or in a particular aspect a siRNA, which can modulate the expression of a gene in a target organism. In an aspect, an exogenous nucleic acid encodes a small RNA having at least 80%, 85%, 88%, 90%, 92%, 95%, 96%, 97%, 98%, or 99% sequence identity to a sequence selected from the group consisting of SEQ ID NOs: 1-4 and 6-94. In a further aspect, an exogenous nucleic acid molecule used herein is or encodes a dsRNA molecule.

In another aspect, an exogenous nucleic acid molecule used herein is or encodes an artificial miRNA. In a further aspect, an exogenous nucleic acid molecule used herein is or encodes an siRNA. In one aspect, an exogenous nucleic acid molecule used herein is or encodes a precursor of a small RNA. In another aspect, an exogenous nucleic acid molecule used herein is or encodes a precursor of a miRNA or siRNA. In one aspect, an exogenous nucleic acid molecule used herein is a naturally-occurring molecule. In another aspect, an exogenous nucleic acid molecule used herein is a synthetic molecule.

In one aspect, an exogenous nucleic acid molecule used herein is or encodes a stem-loop precursor of a small RNA or in a particular aspect a miRNA, comprising a sequence having at least 80%, 85%, 88%, 90%, 92%, 95%, 96%, 97%, 98%, or 99% sequence identity to a sequence selected from the group consisting of SEQ ID NOs: 1-4 and 6-94. A stem-loop precursor used herein comprises a sequence having at least 60%, 65%, 70%, 75%, 80%, 85%, 88%, 90%, 92%, 95%, 96%, 97%, 98%, or 99% sequence identity to a sequence selected from the group consisting of SEQ ID NOs: 1-4 and 6-94.

In one aspect, an exogenous nucleic acid molecule used herein is naked RNA or expressed from a nucleic acid expression construct, where it is operably linked to a regulatory sequence.

In one aspect, a recombinant DNA construct or a transgene disclosed herein further comprises a transcription terminator.

It is expected that during the life of a patent maturing from this application many relevant methods for down-regulating expression of gene products can be developed and the scope of the term "down-regulating expression of a gene product of a *Varroa destructor* mite" is intended to include all such new technologies a priori.

It is appreciated that certain features of the disclosure, which are, for clarity, described in the context of separate aspects, may also be provided in combination in a single aspect. Conversely, various features of the disclosure, which are, for brevity, described in the context of a single aspect, may also be provided separately or in any suitable subcombination or as suitable in any other described aspect of the disclosure. Certain features described in the context of various aspects are not to be considered essential features of those aspects, unless the aspect is inoperative without those elements. Various aspects and aspects of the present disclosure as delineated hereinabove and as claimed in the claims section below find experimental support in the following examples.

EXAMPLES

Example 1. *Varroa* Mite Calmodulin Gene Sequences

The Calmodulin (CAM) genes provided in Table 1 (SEQ ID NO: 1 and 2), or their corresponding transcripts, were used as targets of polynucleotide compositions comprising a polynucleotide that is at least 18 contiguous nucleotides identical or complementary to those genes or transcripts. The gene sequences provided in Table 1, protein sequences encoded by those genes, or sequences contained within those genes were used to obtain orthologous Calmodulin (CAM) genes from other arthropod pest and parasitic species not listed in Table 1. Such orthologous genes and their transcripts can then serve as targets of polynucleotides provided herein or as a source of anti-parasitic, anti-pest or insecticidal polynucleotides that are specifically designed to target the orthologous genes or transcripts.

TABLE 1

Target Calmodulin (CAM) genes of *Varroa destructor*

| Gene name | SEQ ID | Open reading frame DNA sequence |
|---|---|---|
| CAM-1 | 1 | ATGGCTGATCAGCTAACTGAGGAACAGATCGCCGAGTTC AAAGAGGCGTTTAGCCTGTTTGACAAGGACGGAGATGGC ACGATCACGACAAAGGAGCTCGGTACGGTAATGCGATCT CTCGGCCAGAACCCCACTGAGGCTGAACTGCAGGACATG ATCAACGAGGTCGACGCCGACGGCTCCGGAACGATAGAT TTCCCTGAGTTCCTCACAATGATGGCAAGAAAGATGAAG GACACCGACTCGGAGGAGGAGATCCGAGAGGCGTTCCGC GTATTCGACAAGGATGGCAACGGTTTCATTTCGGCGGCC GAGCTCAGGCACGTTATGACCAACCTTGGCGAGAAGCTT ACGGACGAGGAGGTAGATGAGATGATTCGGGAGGCAGAT ATTGACGGTGATGGTCAGGTCAACTACGAGGAGTTCGTC ACCATGATGACGTCCAAGTAA |
| CAM-2 | 2 | ATGGCGGATCAGCTGACCGAGGAGCAAATCGCCGAATTC AAGGAGGCTTTCAGCCTGTTCGATAAAGACGGTGATGGC ACAATTACGACCAAGGAACTAGGGACCGTCATGCGGTCC CTCGGCCAGAACCCTACTGAGGCTGAGCTTCAAGACATG ATCAACGAGGTCGACGCTGACGGTAACGGCACTATTGAC TTTCCAGAGTTTCTCACGATGATGGCGCGTAAAATGAAG GACACCGACTCCGAGGAGGAGATCCGGGAAGCTTTTAGG GTTTTTGATAAAGACGGAAATGGCTTCATTTCGGCTGCA GAGCTGAGGCACGTAATGACCAACCTTGGCGAAAAGCTC ACGGACGAGGAAGTGGACGAGATGATCCGCGAGGCGGAT ATCGACGGCGACGGACAGGTCAACTACGAGGAGTTCGTC ACGATGATGACATCAAAATGA |

For each Calmodulin DNA gene sequence provided in SEQ ID NO: 1 and 2, single stranded or double stranded DNA or RNA fragments in sense or antisense orientation or both are fed in vitro to *Varroa* mites grown on a petri plate or applied topically to bee hives to effect the expression of the CAM target genes and obtain a reduction in *Varroa destructor* mite population.

Example 2. Suppression of Calmodulin (CAM) Genes of *Varroa destructor*

Polynucleotides for the suppression of expression of Calmodulin (CAM) genes in *Varroa destructor* mite corresponding to SEQ ID NOs: 3 and 4 (Table 2) are provided and were used to used to suppress expression of Calmodulin (CAM) genes in *Varroa destructor* mite. The SEQ ID NOs: 3 and 4 describe a 373 bp dsRNA polynucleotide sequence and a 186 bp dsRNA polynucleotide sequence, respectively, selected from CAM-1 (SEQ ID NO: 1). SEQ ID NO: 3, corresponding to dsRNA polynucleotide CAM_L/CAM373 covers most of the open reading frame of the Calmodulin CAM-1 (SEQ ID NO: 1) gene. SEQ ID NO 4, corresponding to dsRNA polynucleotide CAM_S/CAM186 is a partial fragment of CAM_L/CAM373 (SEQ ID NO: 3) and is also derived from CAM-1 (SEQ ID NO: 1). SEQ ID NO: 5 in Table 2 is a control dsRNA sequence polynucleotide sequence with no more than 19 bp sequence identity to any known *Varroa destructor* gene.

TABLE 2 dsRNAs targeting Varroa destructor Calmodulin (CAM) genes

| dsRNA name | SEQ ID | Nucleic acid sequence |
|---|---|---|
| CAM_L/ CAM_373 | 3 | ACAGAUCGCCGAGUUCAAAGAGGCGUUUAGCCUGUUUG ACAAGGACGGAGAUGGCACGAUCACGACAAAGGAGCUC GGUACGGUAAUGCGAUCUCUCGGCCAGAACCCCACUGA GGCUGAACUGCAGGACAUGAUCAACGAGGUCGACGCCG ACGGCUCCGGAACGAUAGAUUUCCCUGAGUUCCUCACA AUGAUGGCAAGAAAGAUGAAGGACACCGACUCGGAGGA GGAGAUCCGAGAGGCGUUCCGCGUAUUCGACAAGGAUG GCAACGGUUUCAUUUCGGCGGCCGAGCUCAGGCACGUU AUGACCAACCUUGGCGAGAAGCUUACGGACGAGGAGGU AGAUGAGAUGAUUCGGGAGGCAGAUAUUGAC |
| CAM_S/ CAM_186 | 4 | ACAAUGAUGGCAAGAAAGAUGAAGGACACCGACUCGGA GGAGGAGAUCCGAGAGGCGUUCCGCGUAUUCGACAAGG AUGGCAACGGUUUCAUUUCGGCGGCCGAGCUCAGGCAC GUUAUGACCAACCUUGGCGAGAAGCUUACGGACGAGGA GGUAGAUGAGAUGAUUCGGGAGGCAGAUAUUGAC |
| SCRAM | 5 | AUACUUACUGGUGCUAAUUUUUAUCGAGGAUGCCCAAC UCCCCCCACUUUAAAACUGCGAUCAUACUAACGAACUC CCGAAGGAGUGAAAGGUGUCUAUGUUGAGCUUAAUAAC CUACCUUGCGAGCAAAGAAGGACUAGUUGACCCUGGGC ACCCUAUAUUGUUAUGUUGUUUCGAACUGAGUUGGCAC CCAUGCUGCACAUGCAACAAACAUGUCGGCCUUCGUGU CUAUCCUAGAAAAGUACCUGUGAACUUGGCUGUCUACA UCAUCAUC |

Example 3. *Varroa destructor* Bioassay at 3 Day Post-Treatment with Specific dsRNAs Adult female mites were collected from honeybee colonies and placed in a petri dish plate on top of an artificial diet solution containing a mixture of 1% tryptone, 0.5% yeast extract, 1% NaCl and 15 mg/mL agar. In this example the diet was supplemented with 50 μg kanamycin per 1 mL of diet solution. The diet/agar solution was further supplemented with 200-500 μg/mL of dsRNA and the resulting solution was poured on a petri dish. The dsRNA in this example consisted of either SEQ ID NO: 3 (CAM_L/CAM373) or SEQ ID NO: 5 (SCRAM). Fifteen mites were applied to each plate and the experiment was conducted in triplicate. The diet plates with the mites were incubated at 29° C. with 50-60% relative humidity. At specific time intervals the plates were inspected and dead mites were counted and removed. For mortality studies the mites were counted three days after being placed on the diet (FIG. 2). FIG. 2 shows that all mites were dead at three day after treatment compared to untreated plates or plates where the mites were fed on a diet supplemented with the non-specific (SCRAM) dsRNA polynucleotide.

Example 4. *Varroa destructor* Bioassay at 5 Day Post-Treatment with dsRNAs Targeting Calmodulin Adult female mites were collected from honeybee colonies and placed in a petri dish plate on top of an artificial diet solution. The artificial diet contained a mixture of 1% tryptone, 0.5% yeast extract, 1% NaCl and 15 mg/mL agar. In this example the diet was further supplemented with Antimycotic Solution (100×, Sigma Aldrich) at 8× final concentration, 500 μg/mL kanamycin and 220 U/mL nystatin. The diet/agar solution was further supplemented with 200-500 μg/mL of dsRNA and the resulting solution was poured on a petri dish. The dsRNA in this example consisted of either SEQ ID NO: 3 (CAM_L/CAM373), or SEQ ID NO: 4 (CAM_S/CAM186), or SEQ ID NO: 5 (SCRAM). Fifteen mites were applied to each plate and the experiment was conducted in triplicate. The diet plates with the mites were incubated at 29° C. with 50-60% relative humidity. At specific time intervals the plates were inspected and dead mites were counted and removed. For mortality studies the mites were counted at five days after being placed on the diet (FIG. 3). For molecular analysis, live mites were removed from the plates, snap frozen in liquid nitrogen and TAQMAN™ analysis was performed to assess the levels of Calmodulin (CAM) RNA. FIG. 3, Panel A. the RNA levels for Calmodulin (CAM) genes in mites exposed to SEQ ID NO: 3 (CAM_L/CAM373) or SEQ ID NO: 4 (CAM_S/CAM186) was highly reduced compared to the non-specific (SCRAM) treatment or no treatment (CNTR). FIG. 3, Panel B, a statistically significant mortality in mites that were exposed to dsRNA against Calmodulin (CAM) was observed at 5 days after treatment.

Example 5. Method for Delivering of dsRNA Polynucleotides Targeting *Varroa* Genes Using a Spray-Dried or Semi-Solid Formulation dsRNA used to suppress expression of *Varroa* target Calmodulin (CAM) genes was prepared in a formulation containing 1 part dsRNA and ~14 parts trehalose in a phosphate buffer (a solution of 1.15 mM $KH_2PO_4$ (monobasic) and 8 mM $Na_2HPO_4$ (dibasic), pH 8.0) as illustrated in Table 3. Using a Büchi B-290 mini spray dryer, the liquid formulation was atomized into droplets and heated with gas to produce a flowable powder.

TABLE 3

Formulation Preparation

| dsRNA | Stock buffer (X % w/v trehalose + phosphate buffer) | Final buffer (X % w/v trehalose + phosphate buffer) | Total vol (mL) | Stock buffer (mL) | dsRNA stock (mL) | Ratio | Active Ingredient (AI) conc (mg/mL) | Active Ingredient (AI) conc (% solids) | Ratio of AI (dsRNA) to Buffer (trehalose + phosphate buffer) |
|---|---|---|---|---|---|---|---|---|---|
| CAM_L/CAM373 | 40 | 10 | 1100 | 275.00 | 825.00 | 1/4 | 7.20 | 0.720 | 13.9 |
| CAM_S/CAM186 | 40 | 10 | 1285 | 321.21 | 963.75 | 1/4 | 6.75 | 0.675 | 14.8 |

The resulting particles were formulated with powdered sugar and applied evenly to hives by spreading the powdered sugar evenly on top of the frames. In other aspects, a semi-solid preparation of the spray-dried material is prepared with water and the sugar-water ("bee-candy") formulation is fed to the bee hives by allowing the bees to feed on it.

Example 6. In Vivo Reduction of *Varroa* Mite in Bee Hives after Treatment with dsRNA Targeting Calmodulin (CAM) Genes

Figure 4:
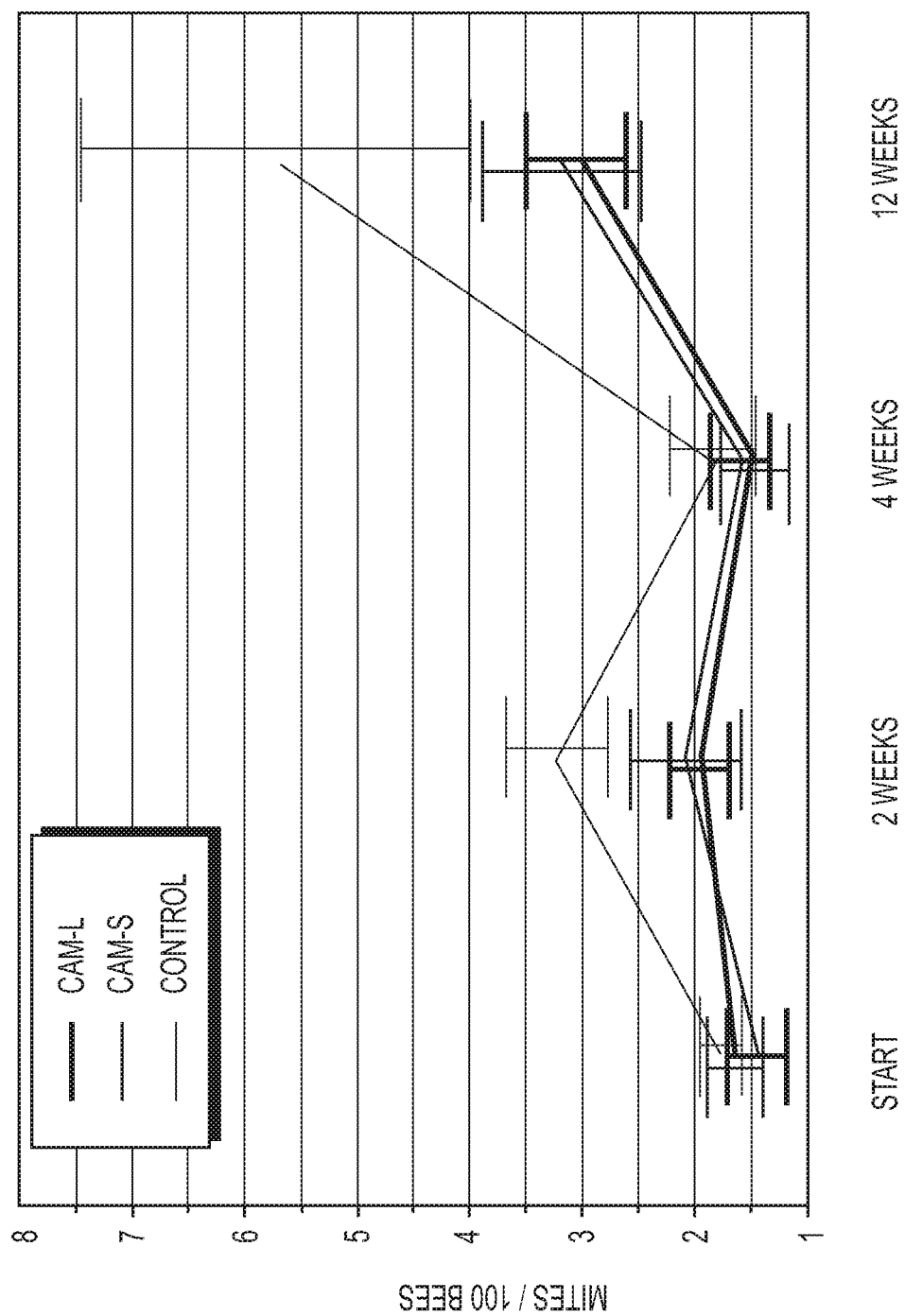
FIG. 4 presents a mite load/100 bees of treated hives relative to untreated controls over a distinct time period.

*Varroa* mites infesting adult honey bees in the hives were collected and counted using standard mite counting methodology. Hives were treated with spray dried dsRNA according to Example 7 comprising SEQ ID NO: 3 (CAM-L), SEQ ID NO: 4 (CAM-S), or no treatment (CONTROL). The mite load of each hive was assessed at the beginning of the experiment and at 2 weeks, 4 weeks and 12 weeks after treatment. FIG. 4 shows the mite load of the treated hives compared to the hives that did not receive the treatment. The number of mites counted was normalized to 100 adult bees and is representative of the *Varroa* mite load.

Example 7. Detection of Transitive Small RNAs in *Varroa* Following Treatment with dsRNA Targeting Calmodulin (CAM) Genes

*Varroa* mites were collected from hives treated with SEQ ID NO: 3 dsRNA polynucleotides and collected from the hive at 7 day after treatment. *Varroa* RNA was extracted and small RNA sequencing analysis performed using the SOLiD platform. The majority of small RNA molecules were detected outside the dsRNA sequence region and specifically toward the 3' portion of the dsRNA region of SEQ ID NO: 3. Additionally, the majority of the transitive reads were in the antisense orientation relative to the Calmodulin (CAM) gene transcript sequence. Further, small RNAs specific for CAM-2 (SEQ ID NO: 2) were detected in this experiment despite the hives being treated with dsRNA for SEQ ID NO: 3, which is predicted to be specific for CAM-1 (SEQ ID NO: 1). This observation supports the hypothesis that suppression of RNA expression and transitive small RNA generation in *Varroa* works even when only a small fragment between the two genes shares complete identity at the DNA level (in this case 23 nucleotides).

Example 8. Calmodulin (CAM) Gene Homologs from Arthropod Pest and Parasite Species and Corresponding dsRNA Polynucleotides Using standard bioinformatics technique and the sequences SEQ ID NOs: 1 and 2 for *Varroa destructor* a set of 31 conserved Calmodulin (CAM) gene sequences were identified in arthropod pest species that infest either other arthropods or mammals and that will be targeted for gene regulation. These sequences were identified and presented as a phylogenetic tree in FIG. 1. The DNA sequences in FIG. 1 were further analyzed by identifying the conserved 373 bp domain within each sequence that corresponds to SEQ ID NO: 3 (CAM_L/CAM373). Table 4 lists the SEQ ID NOs of the newly identified Calmodulin (CAM) gene sequences as well as the corresponding 373 bp dsRNA polynucleotide trigger sequences. The 373 bp polynucleotide dsRNA sequences will be tested either alone or in combination in direct feeding assays against their respective arthropod species.

TABLE 4

Calmodulin (CAM) gene sequences identified from arthropod pests or parasites and their corresponding 373bp RNA polynucleotides.

| SEQ ID NO | Gene Name | Organism/Species | Type |
|---|---|---|---|
| 6 | CAM-3 | Varroa destructor | cDNA |
| 7 | CAM-1 | Ixodes scapularis | cDNA |
| 8 | CAM-1 | Aedes aegypti | cDNA |
| 9 | CAM-1 | Culex quinquefasciatus | cDNA |
| 10 | CAM-1 | Acyrthosiphon pisum | cDNA |
| 11 | CAM-1 | Harpegnathos saltator | cDNA |
| 12 | CAM-1 | Pediculus humanus corporis | cDNA |
| 13 | CAM-1 | Anopheles gambiae | cDNA |
| 14 | CAM-1 | Solenopsis invicta | cDNA |
| 15 | CAM-1 | Ixodes scapularis | RNA |
| 16 | CAM-1 | Aedes aegypti | RNA |
| 17 | CAM-1 | Culex quinquefasciatus | RNA |
| 18 | CAM-1 | Acyrthosiphon pisum | RNA |
| 19 | CAM-1 | Harpegnathos saltator | RNA |
| 20 | CAM-1 | Pediculus humanus corporis | RNA |
| 21 | CAM-1 | Anopheles gambiae | RNA |
| 22 | CAM-1 | Solenopsis invicta | RNA |
| 23 | CAM-3 | Varroa destructor | RNA |
| 24 | CAM-1 | Tetranychus urticae | cDNA |
| 25 | CAM-1 | Tetranychus urticae | RNA |
| 26 | CAM-4 | Varroa destructor | cDNA |
| 27 | CAM-4 | Varroa destructor | RNA |
| 28 | CAM-5 | Varroa destructor | cDNA |
| 29 | CAM-5 | Varroa destructor | RNA |
| 30 | CAM-7 | Varroa destructor | cDNA |
| 31 | CAM-7 | Varroa destructor | RNA |
| 32 | CAM-8 | Varroa destructor | cDNA |
| 33 | CAM-8 | Varroa destructor | RNA |
| 34 | CAM-9 | Varroa destructor | cDNA |
| 35 | CAM-9 | Varroa destructor | RNA |
| 36 | CAM | Ixodes scapularis | cDNA |
| 37 | CAM | Ixodes scapularis | RNA |
| 38 | CAM | Ixodes scapularis | cDNA |
| 39 | CAM | Ixodes scapularis | RNA |
| 40 | CAM | Ixodes scapularis | cDNA |
| 41 | CAM | Ixodes scapularis | cDNA |
| 42 | CAM | Ixodes scapularis | RNA |
| 43 | CAM | Aedes aegypti | cDNA |
| 44 | CAM | Aedes aegypti | RNA |
| 45 | CAM | Aedes aegypti | cDNA |
| 46 | CAM | Aedes aegypti | RNA |
| 47 | CAM | Aedes aegypti | cDNA |
| 48 | CAM | Aedes aegypti | RNA |
| 49 | CAM | Culex quinquefasciatus | cDNA |
| 50 | CAM | Culex quinquefasciatus | RNA |
| 51 | CAM | Culex quinquefasciatus | cDNA |
| 52 | CAM | Culex quinquefasciatus | RNA |
| 53 | CAM | Culex quinquefasciatus | cDNA |
| 54 | CAM | Culex quinquefasciatus | RNA |
| 55 | CAM | Culex quinquefasciatus | cDNA |
| 56 | CAM | Culex quinquefasciatus | RNA |
| 57 | CAM | Acyrthosiphon pisum | cDNA |
| 58 | CAM | Acyrthosiphon pisum | RNA |
| 59 | CAM | Acyrthosiphon pisum | cDNA |
| 60 | CAM | Acyrthosiphon pisum | RNA |
| 61 | CAM | Pediculus humanus | cDNA |
| 62 | CAM | Pediculus humanus | RNA |
| 63 | CAM | Pediculus humanus | cDNA |
| 64 | CAM | Pediculus humanus | RNA |
| 65 | CAM | Pediculus humanus | cDNA |
| 66 | CAM | Pediculus humanus | RNA |
| 67 | CAM | Pediculus humanus | cDNA |
| 68 | CAM | Pediculus humanus | RNA |

Example 9. *Varroa* Calmodulin (CAM) Gene Transcripts and dsRNA Trigger Sequences The Calmodulin (CAM) sequences provided in Table 5 (SEQ ID NOs: 69 and 70), or their corresponding transcripts, were used as targets of polynucleotide compositions comprising a polynucleotide that is at least 18 contiguous nucleotides identical or complementary to those genes or transcripts. The 5' and 3'UTR sequences for the *Varroa* Calmodulin sequences were identified by RNA sequencing.

TABLE 5

Target transcripts for Calmodulin (CAM) genes of *Varroa destructor*

| Gene name and Species | SEQ ID NO | Type |
|---|---|---|
| CAM-1; *Varroa destructor* | 69 | RNA |
| CAM-2; *Varroa destructor* | 70 | RNA |

SEQ ID NOs: 69 and 70 were tiled in 150 bp fragments. Table 6 illustrates the top strand (5'-3') for the 150 bp fragments that tile across SEQ ID NOs: 69 and 70.

TABLE 6

Tiled polynucleotide sequences for CAM-1 and CAM-2 genes

| Gene name | SEQ ID NO | Position within transcript sequence |
|---|---|---|
| CAM-1 | 71 | 1-150 |
| CAM-1 | 72 | 151-300 |
| CAM-1 | 73 | 301-450 |
| CAM-1 | 74 | 451-600 |
| CAM-1 | 75 | 601-750 |
| CAM-1 | 76 | 751-900 |
| CAM-1 | 77 | 901-1050 |
| CAM-1 | 78 | 1051-1200 |
| CAM-1 | 79 | 1201-1350 |
| CAM-1 | 80 | 1351-1500 |
| CAM-2 | 81 | 1-150 |
| CAM-2 | 82 | 151-300 |
| CAM-2 | 83 | 301-450 |
| CAM-2 | 84 | 451-600 |
| CAM-2 | 85 | 601-750 |
| CAM-2 | 86 | 751-900 |
| CAM-2 | 87 | 901-1050 |

One or more dsRNA comprising a sequence selected from SEQ ID NOs: 71-87 is provided in vitro to *Varroa* mites grown on a petri plate or applied topically to bee hives to effect the expression of the CAM target genes and obtain a reduction in *Varroa destructor* mite population.

Example 10. In Vitro Bioassay of Calmodulin (CAM) Targeting Triggers in *Varroa* Mite Polynucleotide trigger sequences targeting Calmodulin (CAM)-1 and 2 were generated based on conserved sequence overlap between CAM-1 and CAM-2 sequences. These are presented as SEQ ID NOs: 88 and 89 (targeting CAM-1 and CAM-2, respectively).

Figure 5:
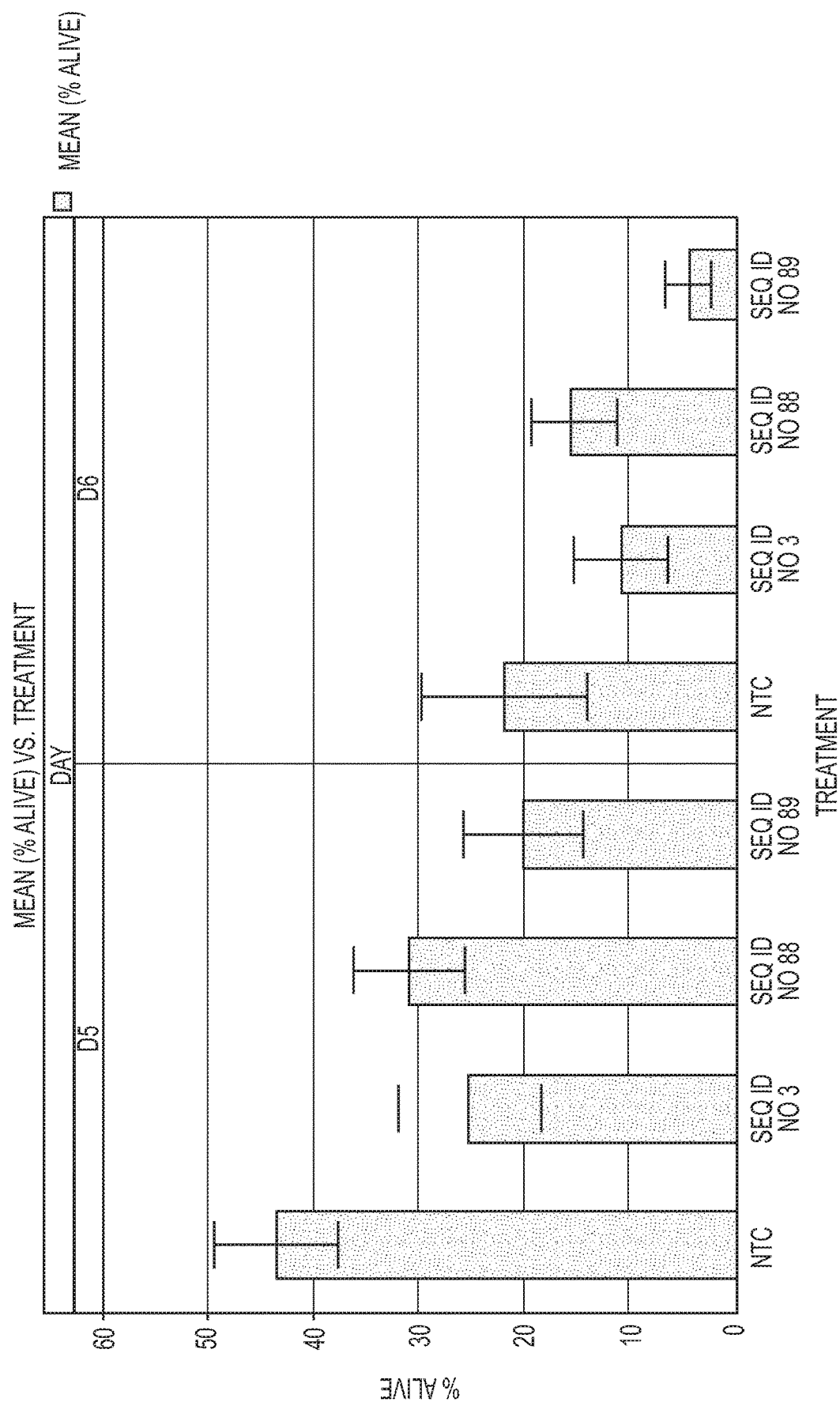
FIG. 5 presents the % survival of mites treated with nucleic acids comprising a sequence identical or complementary to SEQ ID NO: 3, SEQ ID NO: 88 or SEQ ID NO: 89 relative to untreated (NTC) at Day 5 (D %) or Day 6 (D6) post-treatment.
Figure 6:
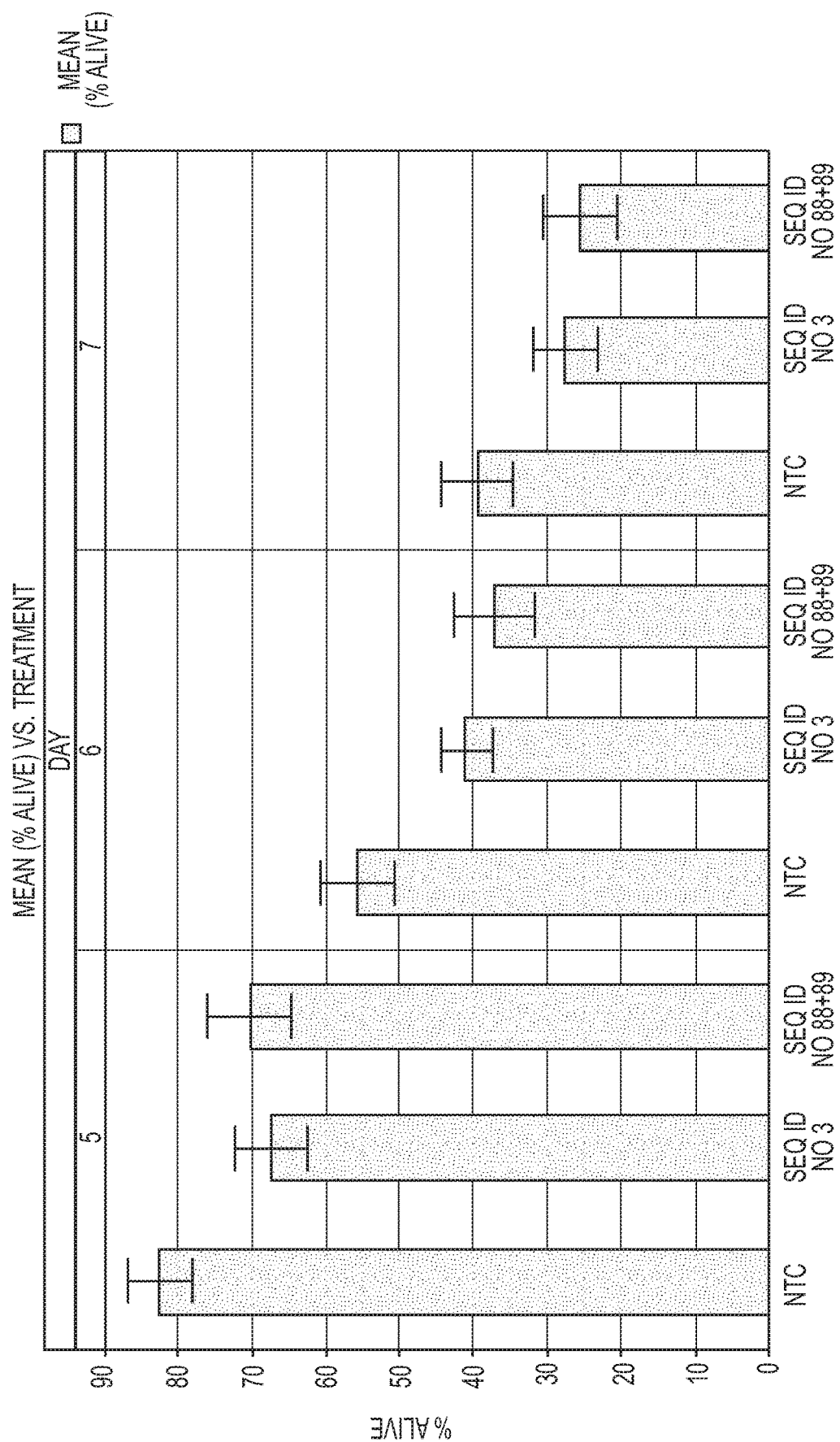
FIG. 6 presents the % survival of mites treated with a nucleic acid comprising a sequence identical or complementary to SEQ ID NO: 3 or a mixture of nucleic acids comprising a sequence identical or complementary to SEQ ID NO: 88 or SEQ ID NO: 89 relative to untreated (NTC) at Day 5 (5), Day 6 (6) and Day 7 (7).

Polynucleotide sequences selected from SEQ ID NOs: 88 and 89 were tested in an in vitro bioassay for their ability to suppress viability of adult *Varroa* mites. Adult female mites were collected from honeybee colonies and placed in a petri dish plate on top of an artificial diet solution. The artificial diet contained a mixture of 1% tryptone, 0.5% yeast extract, 1% NaCl and 15 mg/mL agar. In this example, the diet was further supplemented with Antimycotic Solution (100×, Sigma Aldrich) at 8× final concentration, 500 µg/mL kanamycin and 220 U/mL nystatin. The diet/agar solution was further supplemented with 200-500 µg/mL of dsRNA and the resulting solution was poured on a petri dish. The dsRNA in this example consisted of either SEQ ID NO: 3 (CAM373), SEQ ID NO: 88 (CAM-1), or SEQ ID NO: 89 (CAM-2) or non-treated control (NTC). Fifteen mites were applied to each plate and the experiment was conducted in triplicate. The diet plates with the mites were incubated at 29° C. with 50-60% relative humidity. At specific time intervals the plates were inspected and dead mites were counted and removed. For mortality studies the mites were counted at five and six days after being placed on the diet (FIG. 5.). Additionally, the dsRNA for SEQ ID NO: 88 (CAM-1) and SEQ ID NO: 89 (CAM-2) were mixed in equimolar amount and fed as described above to the mites. FIG. 6 shows the result of this application.

For molecular analysis, live mites are removed from the plates, snap frozen in liquid nitrogen and TAQMAN™ analysis is performed to assess the levels of Calmodulin (CAM) RNA.

Figure 7:
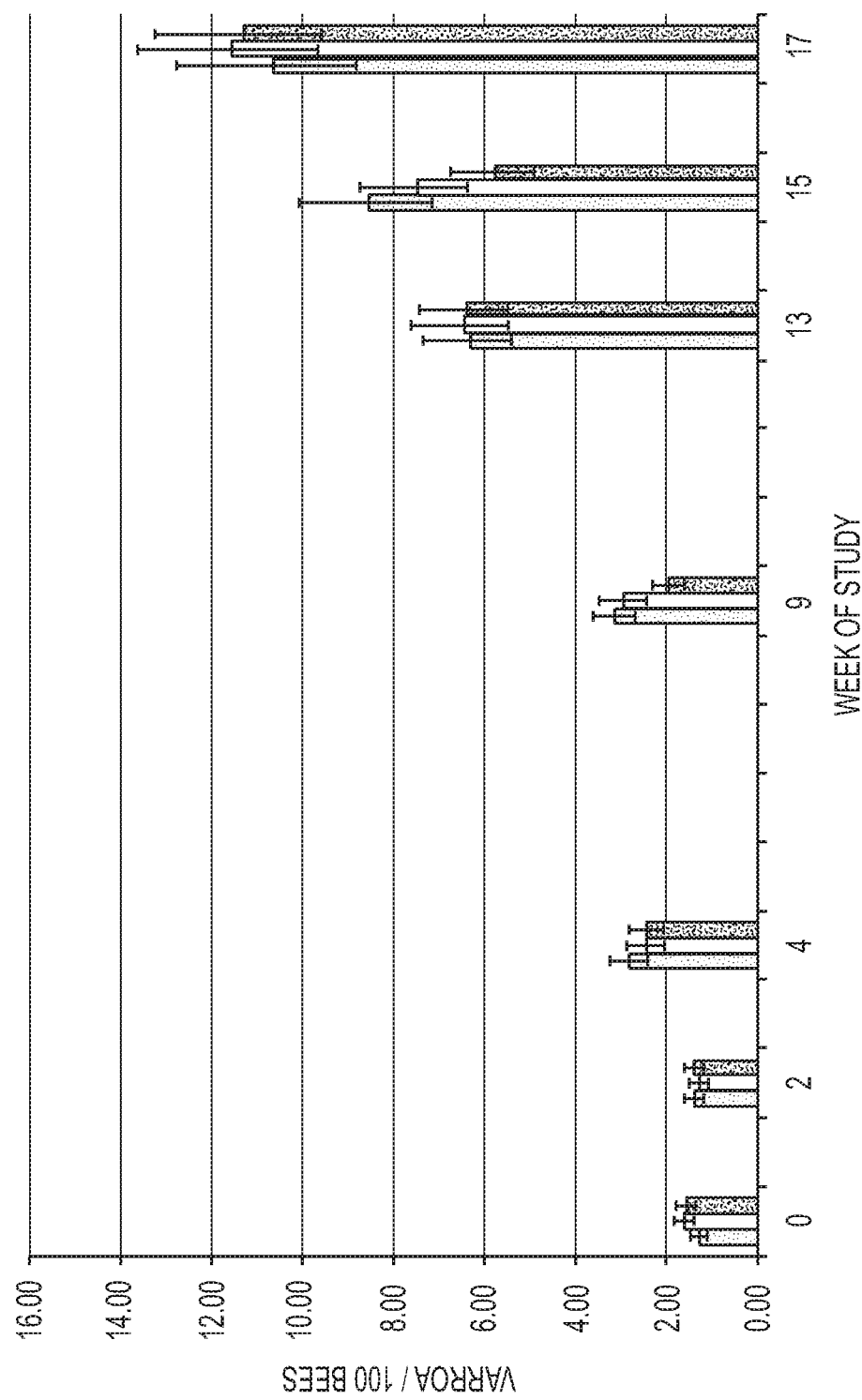
FIG. 7 presents the *Varroa* mite load/100 bees of treated hives relative to untreated controls over a 17 week time period. The leftmost bars represent hives treated with the non-specific sequence (SCRAM, SEQ ID NO: 5), the middle bars are hives left untreated, and the rightmost bar are hives treated with a nucleic acid comprising a sequence identical or complementary to SEQ ID NO: 3 (CAM 373).

Example 11. In Vivo Field Reduction of *Varroa* Mite Infestation in Field Treated Bee Hives after Treatment with dsRNA Targeting Calmodulin (CAM) Gene dsRNA used to suppress expression of *Varroa* targeted Calmodulin (CAM) genes was prepared by mixing dsRNA stock in Phosphate Buffer with 66% sugar syrup. The liquid formulation was supplied as a syrup to the bees, allowed to feed on it until fully consumes (approximately 2-3 days). Each field testing group consisted of 33 hives. The groups consisted of non-treated hives, non-specific trigger treated (SEQ ID NO: 5) and specific trigger treated (SEQ ID NO: 3). Bees were treated in two rounds, each round consisted of two feedings two weeks apart: at the start of the delivery (week 0) and two weeks later (week 2), then again on week 13 and 15. Assessment of bee survival was done at 4, 9, 13, 15 and 17 weeks (FIG. 7). Significant suppression of *Varroa* population was observed following treatment with the specific trigger (SEQ ID NO:3) at week 9.

Example 12. In Vitro Bioassay of Calmodulin (CAM) Targeting Triggers in *Varroa* Mite Polynucleotide trigger sequences targeting Calmodulin (CAM)-1 and 2 were generated based on conserved sequence overlap between CAM-1 and CAM-2 sequences. These are presented in Table 7 as SEQ ID NOs: 3. Additionally, the polynucleotide sequences were modified to avoid containing a consecutive sequence string of 19 bases that are identical or complementary to a gene sequence of a non-target organism. These modifications resulted in polynucleotide SEQ ID NOs: 90-92.

TABLE 7

Triggers targeting CAM-1 and CAM-2

| Gene Target | SEQ ID NO | Native or modified |
|---|---|---|
| CAM-1 | 3 | native |
| CAM-1 | 90 | 4 bp deletion |
| CAM-1 | 91 | 4 bp deletion |
| CAM-2 | 92 | 1 bp deletion |

Polynucleotide sequences were tested in an in vitro bioassay for their ability to suppress viability of adult *Varroa* mites. Adult female mites were collected from honeybee colonies and placed in a petri dish plate on top of an artificial diet solution. The artificial diet contained a mixture of 1% tryptone, 0.5% yeast extract, 1% NaCl and 15 mg/mL agar. In this example the diet was further supplemented with Antimycotic Solution (100×, Sigma Aldrich) at 8× final concentration, 500 µg/mL kanamycin and 220 U/mL nystatin. The diet/agar solution was further supplemented with 200-500 µg/mL of dsRNA (either SEQ ID NO: 3 (CAM373), SEQ ID NO: 90 (CAM-1), or SEQ ID NO: 92 (CAM-2)) and the resulting solution was poured on a petri dish. Plates containing the artificial diet without dsRNA were also prepared (non-treated control (NTC)). Fifteen mites were applied to each plate and the experiment was conducted in triplicate. The diet plates with the mites were incubated at 29° C. with 50-60% relative humidity. At specific time intervals the plates were inspected and dead mites were counted and removed. The mites were counted at five and six days after being placed on the diet to determine mortality.

Figure 8:
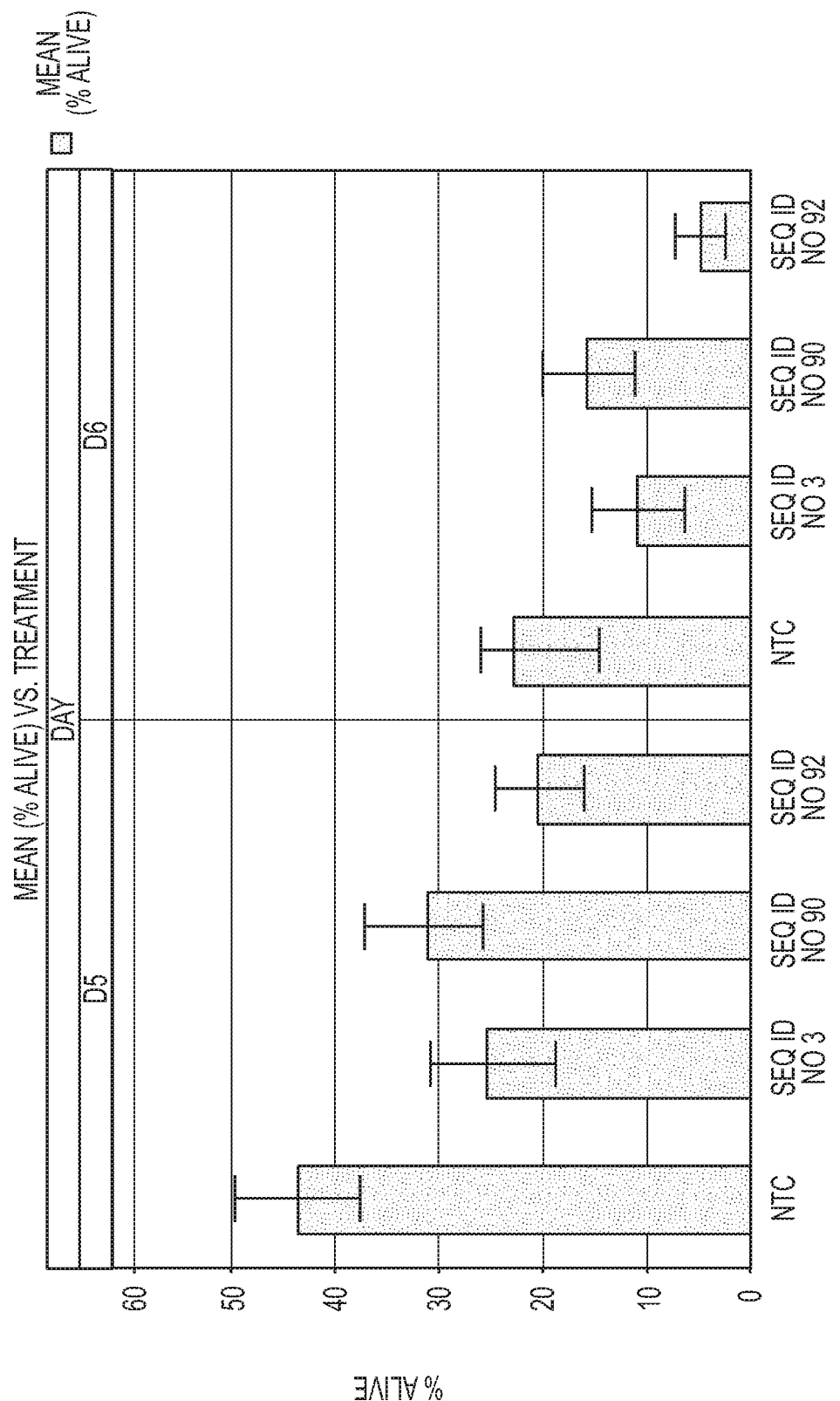
FIG. 8 presents the % survival of the mites treated with a nucleic acid comprising a sequence identical or complementary to SEQ ID NO: 3, a nucleic acid comprising a sequence identical or complementary to SEQ ID NO: 90 or a nucleic acid comprising a sequence identical or complementary to SEQ ID NO: 92 relative to untreated (NTC) at Day 5 (D5) or Day 6 (D6).

As shown in FIG. 8, mites treated with dsRNA (either SEQ ID NO: 3 (CAM373), SEQ ID NO: 90 (CAM-1), or SEQ ID NO: 92 (CAM-2) exhibited increased mortality 5 and 6 days after treatment compared to mites that did not receive RNA.

Figure 9:
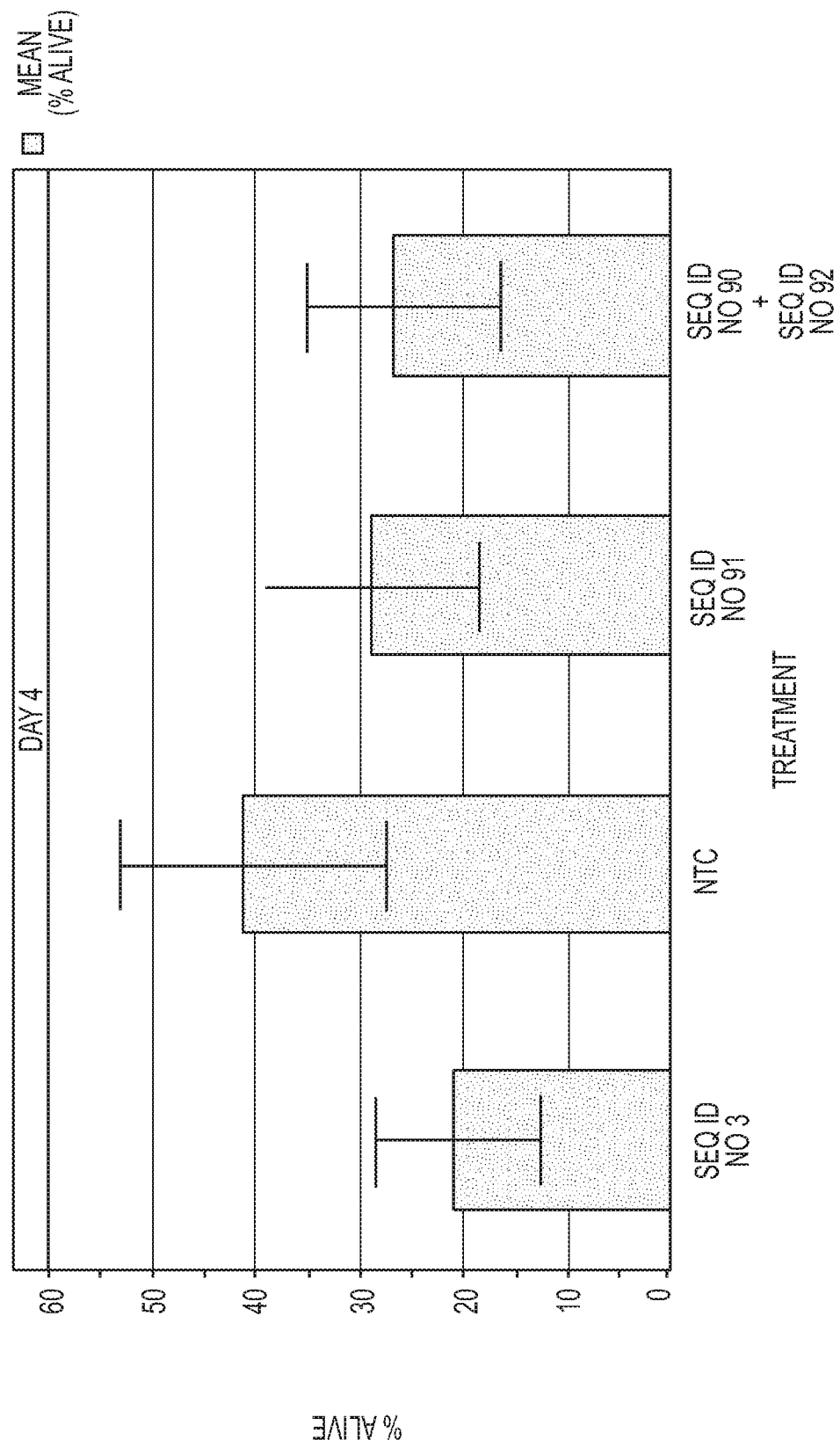
FIG. 9 presents the % survival of the mites treated with a nucleic acid comprising a sequence identical or complementary to SEQ ID NO: 3, a nucleic acid comprising a sequence identical or complementary to SEQ ID NO: 91 or a mixture of nucleic acids comprising a sequence identical or complementary to SEQ ID NO: 90 or SEQ ID NO: 92 relative to untreated (NTC) at Day 4 (D4).
Figure 10:
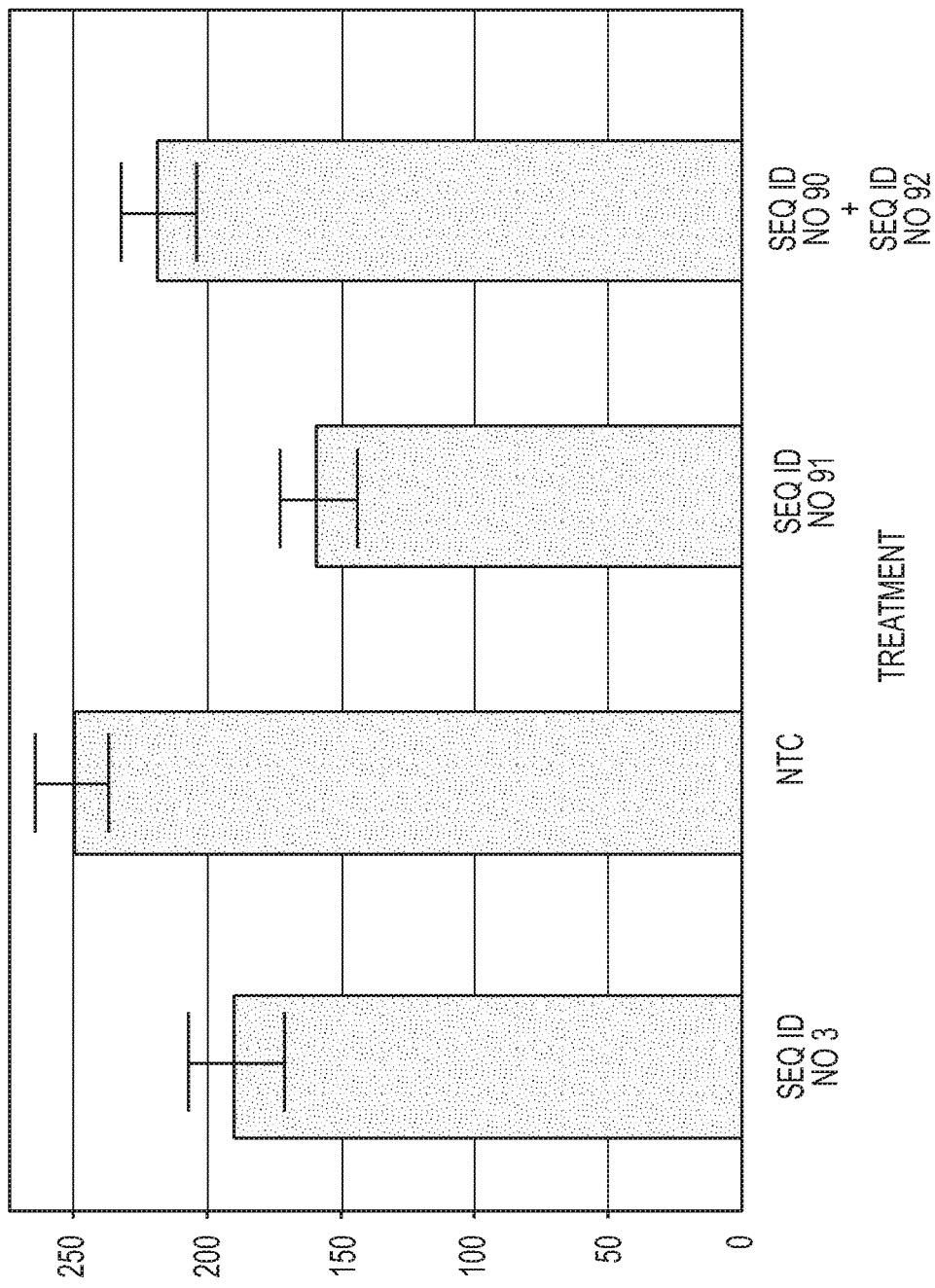
FIG. 10 presents the Calmodulin gene expression analysis as measured by QuantiGene™ (QG) of treatments for SEQ ID NO: 3, SEQ ID NO: 91 and a mixture of SEQ ID NO: 90 and SEQ ID NO: 92 relative to untreated (NTC) at Day 4.

A further in vitro bioassay was performed as described above in which mites were treated with: an equimolar mixture of dsRNA comprising SEQ ID NO: 90 (CAM-1) and SEQ ID NO: 92 (CAM-2); dsRNA comprising SEQ ID NO: 3 (CAM373) or dsRNA comprising SEQ ID NO: 91 (CAM-1). As shown in FIG. 9, mites treated with dsRNA comprising SEQ ID NO: 3, SEQ ID NO: 91 or a mixture of dsRNAs comprising SEQ ID NO: 90 and SEQ ID NO: 92 exhibit reduced viability at Day 4 (D4). Molecular analysis was performed on live mites. Mites were removed from the plates, snap frozen in liquid nitrogen and QuantiGene™ analysis was performed to assess the levels of Calmodulin (CAM) RNA. Results are shown in FIG. 10.

Figure 11:
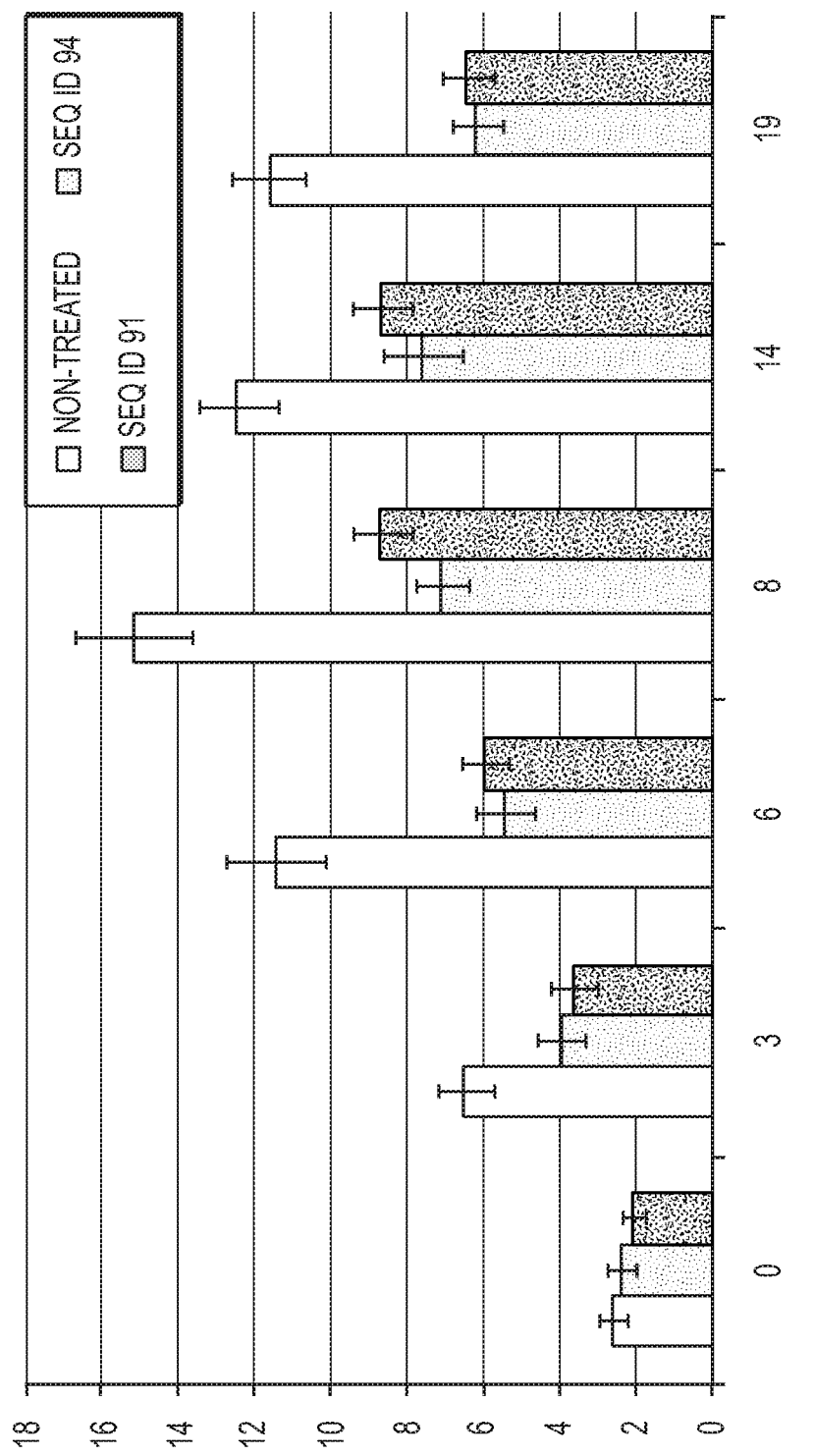
FIG. 11 presents the *Varroa* mite load/100 bees of treated hives relative to untreated controls over a 19 week time period. The leftmost bars represent untreated hives, the middle bars are hives treated with a nucleic acid comprising a sequence identical or complementary to SEQ ID NO: 94 and the rightmost bar are hives treated with a nucleic acid comprising a sequence identical or complementary to SEQ ID NO: 91.

Example 13. In Vivo Field Reduction of *Varroa* Mite Infestation in Field Treated Bee Hives after Treatment with dsRNA Targeting Calmodulin (CAM) Gene dsRNA used to suppress expression of *Varroa* targeted Calmodulin (CAM) genes was prepared by mixing dsRNA stock in Phosphate Buffer with 66% sugar syrup. The liquid formulation was supplied as a syrup to the bees, allowed to feed on it until fully consumes (approximately 2-3 days). Each field testing group consisted of 40 hives. The groups consisted of non-treated and specific trigger treated hives (SEQ ID NO: 91 or SEQ ID NO: 94). SEQ ID NO 94 is identical to SEQ ID NO 3 with the exception of the addition of three bases at the 5'-end of the trigger. Bees were treated in two rounds, each round consisted of two feedings two weeks apart: at the start of the delivery (week 0) and two weeks later (week 2), then again on week 13 and 15. The dosage consisted of approximately 200 mg trigger per hive. Assessment of bee survival was done at 0, 3, 6, 8, 14 and 19 weeks (FIG. 11). Significant suppression of *Varroa* population was observed following treatment with the specific triggers (SEQ ID NO:91 and 94) already at week 3.

What is claimed is:

1. A selective insecticide composition comprising a nucleic acid molecule having a sequence that is essentially complementary or essentially identical to a region of a targeted calmodulin gene sequence, or an RNA transcribed therefrom, wherein said nucleic acid molecule is a double-stranded RNA (dsRNA) comprising a sequence selected from SEQ ID NOs: 90-92, and wherein the nucleic acid molecule does not comprise a sequence of 19 or more contiguous nucleotides that are 100% identical or complementary to a gene sequence of a non-target organism.

2. A nucleic acid construct comprising a nucleic acid molecule that is essentially identical or essentially complementary to a region of a targeted calmodulin gene sequence, or an RNA transcribed therefrom, operably linked to a promoter sequence functional in a host cell and capable of producing a dsRNA when introduced into said host cell, wherein said dsRNA comprises a sequence selected from SEQ ID NOs: 90-92, and wherein the nucleic acid molecule does not comprise a sequence of 19 or more contiguous nucleotides that are 100% identical or complementary to a gene sequence of a non-target organism.

3. A method of selectively treating an arthropod species for parasites, comprising delivering an effective amount of a nucleic acid molecule that is essentially identical or essentially complementary to a region of a target parasite calmodulin gene sequence, or an RNA transcribed therefrom, to an arthropod species, wherein said nucleic acid molecule is a dsRNA comprising a sequence selected from SEQ ID NOs: 90-92, and wherein the nucleic acid molecule does not comprise a sequence of 19 or more contiguous nucleotides that are 100% identical or complementary to a gene sequence of a non-target organism.

4. The selective insecticide composition of claim 1, further comprising an excipient.

5. The selective insecticide composition of claim 4, wherein said composition is bee-ingestible, bee-absorbable, mite-ingestible, or mite-absorbable.

6. The selective insecticide composition of claim 4, wherein said excipient is selected from the group consisting of protein, pollen, carbohydrate, polymer, liquid solvent, sugar syrup, sugar solid, and semi-solid feed.

7. The selective insecticide composition of claim 1, wherein the composition further comprises one or more nucleic acid molecules.

8. The selective insecticide composition of claim 7, wherein said one or more nucleic acid molecules comprise a second nucleic acid sequence complementary to a second region of a targeted calmodulin gene sequence.

9. The method of claim 3, wherein said treatment decreases the parasitic load of said arthropod species, reduces the death of said arthropod species, or prevents parasitation of said arthropod species.

10. The method of claim 3, wherein said arthropod species is selected from the group consisting of *Apis mellifera, Apis cerana, Trigona minima, Halictidae, Bombus* sp., Ichneumonoidea (parasitic wasps), fleas, flies, lice, ticks, and mites.

11. The method of claim 3, wherein said parasites are selected from the group consisting of Acari (ticks, mites), Hippoboscoidea (flies), Ichneumonoidea (parasitic wasps), Oestridae (bot flies), Phthiraptera (lice), Siphonaptera (fleas), Tantulocarida, Pea crab, and Sacculina.

12. The method of claim 3, wherein said delivering comprises a method selected from the group consisting of delivery through a feeder, spraying on hive frames, and contact using an intra-hive device impregnated with said composition.

13. The selective insecticide composition of claim 1, wherein said dsRNA comprises the sequence of SEQ ID NO: 90.

14. The selective insecticide composition of claim 1, wherein said dsRNA comprises the sequence of SEQ ID NO: 91.

15. The selective insecticide composition of claim 1, wherein said dsRNA comprises the sequence of SEQ ID NO: 92.

16. The method of claim 3, wherein said dsRNA comprises the sequence of SEQ ID NO: 90.

17. The method of claim 3, wherein said dsRNA comprises the sequence of SEQ ID NO: 91.

18. The method of claim 3, wherein said dsRNA comprises the sequence of SEQ ID NO: 92.

* * * * *

SEQUENCE LISTING

```
<160> NUMBER OF SEQ ID NOS: 94

<210> SEQ ID NO 1
<211> LENGTH: 450
<212> TYPE: DNA
<213> ORGANISM: Varroa destructor

<400> SEQUENCE: 1
atggctgatc agctaactga ggaacagatc gccgagttca aagaggcgtt tagcctgttt      60
gacaaggacg gagatggcac gatcacgaca aaggagctcg gtacggtaat gcgatctctc     120
ggccagaacc ccactgaggc tgaactgcag gacatgatca acgaggtcga cgccgacggc     180
tccggaacga tagatttccc tgagttcctc acaatgatgg caagaaagat gaaggacacc     240
gactcggagg aggagatccg agaggcgttc gcgtattcg acaaggatgg caacggtttc     300
atttcggcgg ccgagctcag gcacgttatg accaaccttg gcgagaagct tacggacgag     360
gaggtagatg agatgattcg ggaggcagat attgacggtg atggtcaggt caactacgag     420
gagttcgtca ccatgatgac gtccaagtaa                                       450

<210> SEQ ID NO 2
<211> LENGTH: 450
<212> TYPE: DNA
<213> ORGANISM: Varroa destructor

<400> SEQUENCE: 2
atggcggatc agctgaccga ggagcaaatc gccgaattca aggaggcttt cagcctgttc      60
gataaagacg gtgatggcac aattacgacc aaggaactag gaccgtcat gcggtccctc      120 ggccagaacc ctactgaggc tgagcttcaa gacatgatca acgaggtcga cgctgacggt     180
aacggcacta ttgactttcc agagtttctc acgatgatgg cgcgtaaaat gaaggacacc     240
gactccgagg aggagatccg ggaagctttt agggttttg ataaagacgg aaatggcttc     300
```

```
atttcggctg cagagctgag gcacgtaatg accaaccttg gcgaaaagct cacggacgag    360
gaagtggacg agatgatccg cgaggcggat atcgacggcg acggacaggt caactacgag    420
gagttcgtca cgatgatgac atcaaaatga                                     450
```

<210> SEQ ID NO 3
<211> LENGTH: 373
<212> TYPE: RNA
<213> ORGANISM: Varroa destructor

<400> SEQUENCE: 3

```
acagaucgcc gaguucaaag aggcguuuag ccuguuugac aaggacggag auggcacgau     60
cacgacaaag gagcucggua cgguaaugcg aucucucggc cagaaccccca cugaggcuga   120 acugcaggac augaucaacg aggucgacgc cgacggcucc ggaacgauag auuucccuga   180
guuccucaca augauggcaa gaaagaugaa ggacaccgac ucgaggagg agauccgaga    240 ggcguuccgc guauucgaca aggauggcaa cgguuucauu ucggcggccg agcucaggca   300
cguuaugacc aaccuuggcg agaagcuuac ggacgaggag guagaugaga ugauucggga   360
ggcagauauu gac                                                       373
```

<210> SEQ ID NO 4
<211> LENGTH: 186
<212> TYPE: RNA
<213> ORGANISM: Varroa destructor

<400> SEQUENCE: 4

```
acaaugaugg caagaaagau gaaggacacc gacucggagg aggagauccg agaggcguuc     60
cgcguauucg acaaggaugg caacgguuuc auuucggcgg ccgagcucag gcacguuaug   120
accaaccuug gcgagaagcu uacggacgag gaguagaug agaugauucg ggaggcagau   180
auugac                                                               186
```

<210> SEQ ID NO 5
<211> LENGTH: 274
<212> TYPE: RNA
<213> ORGANISM: Artificial Sequence
<220> FEATURE:
<223> OTHER INFORMATION: synthetic sequence

<400> SEQUENCE: 5

```
auacuuacug gugcuaauuu uuaucgagga ugcccaacuc cccccacuuu aaaacugcga     60
ucauacuaac gaacucccga aggagugaaa ggugucuaug uugagcuuaa uaaccuaccu   120
ugcgagcaaa gaaggacuag uugacccugg gcacccuaua uuguuauguu guuucgaacu   180
gaguuggcac ccaugcugca caugcaacaa acaugucggc cuucgugucu auccagaaa   240 aguaccugug aacuuggcug ucuacaucau cauc                                274
```

<210> SEQ ID NO 6
<211> LENGTH: 432
<212> TYPE: DNA
<213> ORGANISM: Varroa destructor

<400> SEQUENCE: 6

```
ctgccggagg aacaggtggc tgaatttaaa gaggcctttc ttttgtttga caaggacgcc     60
gatggaatga ttacggccgc cgaactaggc gtcgtcatgc gatcgcttgg ccagcgacct   120
acggagcaag agctcaagaa aatggttacc atggttgacc aggacggcaa tggtacaatc   180
gagttcaacg agttttttgat gatgatgtct cgcaagatga aggaggcaga ctcggaggaa   240
```

```
gaactccggg aggcgttccg tgtgttcgat cgagacggtg acggattcat ctcgcgggac    300
gagctcagtg tcgtcatgaa caacctcggc gagaaattaa gtgacgatga tgttgaggat    360
atgattcgag aggccgatct ggacggcgat ggcaagatta actaccaaga gtttgtgctc    420
attatcacct cc                                                        432

<210> SEQ ID NO 7
<211> LENGTH: 480
<212> TYPE: DNA
<213> ORGANISM: Ixodes scapularis

<400> SEQUENCE: 7
atggctgatc agcttacaga agaacagatt gcagttcaag gaggcgttct tcgctgttcg     60
acaaggacgg aggatggcac catcacgacc aaggagctgg gcacggtcat gcgctcgctc    120
ggccagaacc cgacggaggc ggagctgcag acatgatca acgaggtgga cgcagacggc    180
aacggaacga tcgacttccc cgagttcctt acgatgatgg cgcgcaagat gaaggacacg    240
gactctgagg aggagatccg ggaggcgttc cgggtgttcg acaaggacgg caacggcttc    300
atctctgcgg cggagctgcg ccacgtcatg accaacctgg gcgagaagct gacggacgag    360
gaggtggacg agatgatccg ggaggcggac atcgacgggg acgggcaggt caactacgaa    420
ggtgggcacg ctttccctcc cttggttatc ctcctgctat gctttctgca gttgctgtga    480

<210> SEQ ID NO 8
<211> LENGTH: 450
<212> TYPE: DNA
<213> ORGANISM: Aedes aegypti

<400> SEQUENCE: 8
atggccgatc aacttacaga agagcagatt gccgaattca agaagcgtt ttcgctgttc      60 gacaaagacg gtgacggcac aatcacaacc aaggaactgg gaaccgtgat gcgatcgtta    120
ggccagaacc ccacagaagc agaactgcaa gatatgataa acgaagtcga cgcggacggc    180
aacggcacga tcgatttccc cgaattcctg accatgatgg ctcgcaaaat gaaggacacc    240
gatagcgaag aggaaatccg ggaggcgttc cgagtcttcg acaaggacgg caacggcttc    300
atctcggcag ctgagctgcg tcatgtcatg accaatctcg gcgagaagct aacggacgag    360
gaggtggatg agatgatccg cgaagccgac atagatggcg atggccaagt taattatgaa    420
gaattcgtaa caatgatgac atcgaagtga                                     450

<210> SEQ ID NO 9
<211> LENGTH: 450
<212> TYPE: DNA
<213> ORGANISM: Culex quinquefasciatus

<400> SEQUENCE: 9
atggccgatc aacttacaga ggaacagatc gccgagttca agaagcgtt ctcgctgttc      60 gacaaagacg gtgacggcac gatcacgacc aaggagctgg caccgtgat gcgatcgtta    120 ggccagaacc ccacagaagc agagctgcaa gacatgataa acgaggtcga tgcggacggc    180
aacggcacga tcgacttccc cgagtttctc accatgatgg ctcgcaaaat gaaggacacc    240
gatagcgaag aggaaatccg ggaggcgttc cgagtcttcg acaaggacgg caacggcttc    300
atctcggcgg ccgagctgcg ccacgtcatg accaatctcg gcgagaagct cacggacgag    360
gaggtggatg agatgatccg cgaggccgac attgacggcg atggccaagt taattatgaa    420
```

```
gaattcgtaa caatgatgac atcgaagtga                                      450
```

<210> SEQ ID NO 10
<211> LENGTH: 450
<212> TYPE: DNA
<213> ORGANISM: Acyrthosiphon pisum

<400> SEQUENCE: 10

```
atggctgatc aactaacaga agaacagatt gccgaattca aagaggcgtt ttcgctattc     60
gacaaggacg gagatggtac catcaccacc aaagaacttg gaaccgtcat gaggtcttta    120
ggccaaaatc cgactgaagc tgaactccaa gatatgatta acgaggtcga tgctgatggc    180
aacggcacga tagatttccc agagttcttg actatgatgg cccgcaaaat gaaggatacc    240
gatagtgagg aagaaatcag agaggctttc cgtgtatttg ataaggatgg aaacggcttt    300
attagtgcag ctgagctgcg tcatgtgatg actaaccttg agaaaagct caccgatgaa     360
gaggttgatg aaatgatcag ggaagctgac attgatggtg atggtcaagt caactatgaa    420
gagttcgtga ccatgatgac ttctaagtga                                      450
```

<210> SEQ ID NO 11
<211> LENGTH: 441
<212> TYPE: DNA
<213> ORGANISM: Harpegnathos saltator

<400> SEQUENCE: 11

```
caactcacag aggaacagat cgcagagttt aaggaagcct tctcgctatt cgacaaagat     60
ggcgatggca ctataacgac taagaattg ggtacagtca tgcgatccct gggtcaaaat    120
cccacagagg ccgagttaca agacatgatt aatgaagtag acgcagatgg taacggtaca    180
atcgactttc cggagttctt gaccatgatg gcacgcaaaa tgaaggatac ggacagcgag    240
gaggagatca gggaggcctt cagagtgttc gataaggatg gaaatggttt catatccgca    300
gcggaactca gacatgttat gacaaatctg ggcgagaaac tgaccgatga ggaagtagat    360
gaaatgatac gggaggcaga tatcgacggc gatggccaag tgaattatga agaatttgtg    420
acgatgatga catcaaagtg a                                              441
```

<210> SEQ ID NO 12
<211> LENGTH: 459
<212> TYPE: DNA
<213> ORGANISM: Pediculus humanus corporis

<400> SEQUENCE: 12

```
atggtttctt ttttttttgcg agctgatcag ttgaccgaag aacaaattgc cgaattcaag     60
gaagcatttt ccttattcga caaagatggc gatggtacca taacaactaa ggaattgggt    120
acggttatga gatcactcgg tcagaatccc acagaagcag aattacaaga tatgattaat    180
gaagtggatg cagatggtaa tggtaccatc gattttcccg agttcctcac catgatggct    240
agaaaaatga aggatacaga cagcgaagaa gaaattagaa aagcattcag agttttcgat    300
aaggatggta atggttttat atcggcagcc gagctaaggc acgtcatgac gaacctgggt    360
gaaaaattaa cagacgaaga agtggatgaa atgattcgag aggctgatat cgacggagat    420
ggacaagtga attacgaaga atttgtggaa aacttgtga                           459
```

<210> SEQ ID NO 13
<211> LENGTH: 459
<212> TYPE: DNA
<213> ORGANISM: Anopheles gambiae

```
<400> SEQUENCE: 13
atggccgatc aacttacgga agaacagatc gctgaattca agaagcgtt  ctcgctgttc      60 gacaaggacg gcgatggcac aatcaccacc aaggaattag gcaccgtgat gcgatcgcta     120
ggccagaacc ccacagaagc tgaattgcaa gacatgatca cgaagtcga  cgcggacggt     180 aacggcacga tcgatttccc cgagtttcta caatgatgg  ctcgtaaaat gaaggacacg     240
gacagtgaag aggaaatccg ggaggcattc cgagtcttcg acaaggacgg caacggtttt     300
atctctgcag ctgagctgcg ccacgtcatg actaatctgg gcgagaagct aacagacgag     360
gaggtcgacg agatgatccg tgaagccgat atagatggcg atggccaggt taattatgaa     420
ggtaagagtt gcctttcgcg cccacaccaa gcattgttt                            459

<210> SEQ ID NO 14
<211> LENGTH: 501
<212> TYPE: DNA
<213> ORGANISM: Solenopsis invicta

<400> SEQUENCE: 14
atgatcggca cgataacgac gagaaattcc attatttcag aattcaaaga ggcatttatg      60
cttttcgaca aggacgaaga tggcacgatt acgatggcgg aattaggggt tgtcatgcgg     120
tctctcggtc aaagaccgtc ggagacggaa ctgcgcgata tggtgaatga ggtagatcaa     180
gatggaaatg gtaccatcga gtttaacgaa tttctgcaga tgatgtcgaa gaagatgaaa     240
agcgccgacg gagaggacga acttcgcgag gcgttccgag tgttcgataa gaacaacgat     300
ggcttaatat cttcgaaaga gttgcgacac gtaatgacga atcttggtga aaagctctct     360
gaggaggagg tcgatgatat gattaaggag gcggatctag atggcgacgg aatggtcaac     420
tacgaaggta acatttttgtt ttgcctagat gtttattcta aatagatttt agaatttatt     480
ctaagcgata tagatgaatt g                                               501

<210> SEQ ID NO 15
<211> LENGTH: 364
<212> TYPE: RNA
<213> ORGANISM: Ixodes scapularis

<400> SEQUENCE: 15
aguucaagga ggcguucuuc gcuguucgac aaggacggag gauggcacca ucacgaccaa      60
ggagcugggc acggucaugc gcucgcucgg ccagaacccg acggaggcgg agcugcagga     120
caugaucaac gaggugg acg cagacggcaa cggaacgauc gacuucccg  aguuccuuac     180 gaugauggcg cgcaagauga aggacacgga cucugaggag gagauccggg aggcguuccg     240
gguguucgac aaggacggca acggcuucau cucugcggcg gagcugcgcc acgucaugac     300
caaccugggc gagaagcuga cggacgagga ggugga cgag augauccggg aggcggacau     360
cgac                                                                  364

<210> SEQ ID NO 16
<211> LENGTH: 372
<212> TYPE: RNA
<213> ORGANISM: Aedes aegypti

<400> SEQUENCE: 16
gcagauugcc gaauucaaag aagcguuuuc gcuguucgac aaagacgguq acggcacaau      60 cacaaccaag gaacugggaa ccgugaugcg aucguuaggc cagaaccccca cagaagcaga    120
```

```
acugcaagau augauaaacg aagucgacgc ggacggcaac ggcacgaucg auuuccccga      180
auuccugacc augauggcuc gcaaaaugaa ggacaccgau agcgaagagg aaauccggga      240
ggcguuccga gucuucgaca aggacggcaa cggcuucauc ucggcagcug agcugcguca      300
ugucaugacc aaucucggcg agaagcuaac ggacgaggag guggaugaga ugauccgcga      360
agccgacaua ga                                                         372
```

<210> SEQ ID NO 17
<211> LENGTH: 373
<212> TYPE: RNA
<213> ORGANISM: Culex quinquefasciatus

<400> SEQUENCE: 17

```
acagaucgcc gaguucaaag aagcguucuc gcuguucgac aaagacggug acggcacgau      60
cacgaccaag gagcugggca ccgugaugcg aucguuaggc cagaaccccca cagaagcaga    120 gcugcaagac augauaaacg aggucgaugc ggacggcaac ggcacgaucg acuuccccga    180
guuucucacc augauggcuc gcaaaaugaa ggacaccgau agcgaagagg aaauccggga    240
ggcguuccga gucuucgaca aggacggcaa cggcuucauc ucggcggccg agcugcgcca    300
cgucaugacc aaucucggcg agaagcucac ggacgaggag guggaugaga ugauccgcga    360
ggccgacauu gac                                                       373
```

<210> SEQ ID NO 18
<211> LENGTH: 372
<212> TYPE: RNA
<213> ORGANISM: Acyrthosiphon pisum

<400> SEQUENCE: 18

```
acagauugcc gaauucaaag aggcguuuuc gcuauucgac aaggacggag augguaccau      60
caccaccaaa gaacuuggaa ccgucaugag gucuuuaggc caaaauccga cugaagcuga    120
acuccaagau augauuaacg aggucgaugc ugauggcaac ggcacgauag auuucccaga    180
guucuugacu augauggccc gcaaaaugaa ggauaccgau agugaggaag aaaucagaga    240
ggcuuuccgu guauuugaua aggauggaaa cggcuuuauu agugcagcug agcugcguca    300
ugugaugacu aaccuuggag aaaagcucac cgaugaagag guugaugaaa ugaucaggga    360
agcugacauu ga                                                        372
```

<210> SEQ ID NO 19
<211> LENGTH: 373
<212> TYPE: RNA
<213> ORGANISM: Harpegnathos saltator

<400> SEQUENCE: 19

```
acagaucgca gaguuuaagg aagccuucuc gcuauucgac aaagauggcg augg cacuau     60 aacgacuaaa gaauugggua cagucaugcg aucccugggu caaaauccca cagaggccga    120
guuacaagac augauuaaug aaguagacgc agauggu aac ggu acaaucg acuuccgga   180 guucuugacc augauggcac gcaaaaugaa ggauacggac agcgaggagg agaucaggga    240
ggccuucaga guguucgaua aggauggaaa ugguuucaua uccgcagcgg aacucagaca    300
uguuaugaca aaucugggcg agaaacugac cgaugaggaa guagaugaaa ugauacggga    360
ggcagauauc gac                                                       373
```

<210> SEQ ID NO 20
<211> LENGTH: 373

```
<212> TYPE: RNA
<213> ORGANISM: Pediculus humanus corporis

<400> SEQUENCE: 20
acaaauugcc gaauucaagg aagcauuuuc cuuauucgac aaagauggcg augguaccau      60
aacaacuaag gaauugggua cgguuaugag aucacucggu cagaauccca cagaagcaga    120
auuacaagau augauuaaug aaguggaugc agaugguaau gguaccaucg auuucccga     180 guuccucacc augauggcua gaaaaaugaa ggauacagac agcgaagaag aaauuagaga    240
agcauucaga guuucgauua aggaugguaa ugguuuuaua ucggcagccg agcuaaggca    300
cgucaugacg aaccuggguu aaaaauuaac agacgaagaa guggaugaaa ugauucgaga    360
ggcugauauc gac                                                        373

<210> SEQ ID NO 21
<211> LENGTH: 372
<212> TYPE: RNA
<213> ORGANISM: Anopheles gambiae

<400> SEQUENCE: 21
acagaucgcu gaauucaaag aagcguucuc gcuguucgac aaggacggcg auggcacaau     60
caccaccaag gaauuaggca ccgugaugcg aucgcuaggc cagaaccccca cagaagcuga   120 auugcaagac augaucaacg aagucgacgc ggacgguaac ggcacgaucg auuuccccga    180
guuucuaaca augauggcuc guaaaaugaa ggacacggac agugaagagg aaauccggga    240
ggcauuccga gucuucgaca aggacggcaa cgguuuuauc ucugcagcug agcugcgcca    300
cgucaugacu aaucugggcg agaagcuaac agacgaggag gucgacgaga uguccguga    360 agccgauaua ga                                                        372

<210> SEQ ID NO 22
<211> LENGTH: 364
<212> TYPE: RNA
<213> ORGANISM: Solenopsis invicta

<400> SEQUENCE: 22
cagaauucaa agaggcauuu augcuuuucg acaaggacga agauggcacg auuacgaugg     60
cggaauuagg gguugucaug cggucucucg gucaaagacc gucggagacg gaacugcgcg    120
auauggugaa ugagguagau caagauggaa augguaccau cgaguuuaac gaauucugc     180 agaugaugauc gaagaagaug aaaagcgccg acggagagga cgaacuucgc gaggcguucc    240
gagguuucga uaagaacaac gauggcuuaa uaucuucgaa agagugcga cacguaauga    300 cgaaucuugg ugaaaagcuc ucugaggagg aggucgauga uaugauuaag gaggcggauc    360
uaga                                                                  364

<210> SEQ ID NO 23
<211> LENGTH: 373
<212> TYPE: RNA
<213> ORGANISM: Varroa destructor

<400> SEQUENCE: 23
acagguggcu gaauuuaaag aggccuuucu uuuguuugac aaggacgccg auggaaugau     60
uacggccgcc gaacuaggcg ucgucaugcg aucgcuuggc cagcgaccua cggagcaaga   120
gcucaagaaa auguuuacca ugguugacca ggacggcaau gguacaaucg aguucaacga    180
guuuuugaug augaugucuc gcaagaugaa ggaggcagac ucggaggaag aacuccggga    240
```

```
ggcguuccgu guguucgauc gagacgguga cggauucauc ucgcgggacg agcucagugu    300
cgucaugaac aaccucggcg agaaauuaag ugacgaugau guugaggaua ugauucgaga    360
ggccgaucug gac                                                       373
```

```
<210> SEQ ID NO 24
<211> LENGTH: 627
<212> TYPE: DNA
<213> ORGANISM: Tetranychus urticae

<400> SEQUENCE: 24
attcatcaga tttaaaatta ttcaccttgt acctgaatta aaacaatagt attatataag     60
atggctgacc agctaactga agagcaaatt gctgaattta aggaggcctt ttcattgttt    120
gataaagatg gtgatggtac aattaccacc aaggaattgg gaactgttat gagaagtcta    180
ggtcaaaatc aacagaaagc ggaattacaa gatatgatca atgaagttga tgccgatggt    240
aatggtacta ttgattttcc tgaattcttg actatgatgg ctagaaaaat gaaggataca    300
gactcagagg aggaaatccg tgaagctttc cgtgtttttg ataaagatgg taatggtttt    360
atttctgctg ctgaattgag acatgtaatg accaatttgg gtgaaaaatt gaccgacgaa    420
gaagtagatg aaatgattcg tgaagccgat attgacggtg atggtcaagt taattatgaa    480
gaatttgtaa cgatgatgac atccaaatga ataaaagcac aaggttaatt gttcatttta    540
attagatcca atggatccca tcagtgacag ggataaaaat taatcaataa aagatgaaaa    600
gcaaaaaata catggaagct atcatca                                        627
```

```
<210> SEQ ID NO 25
<211> LENGTH: 372
<212> TYPE: RNA
<213> ORGANISM: Tetranychus urticae

<400> SEQUENCE: 25
caaauugcug aauuuaagga ggccuuuuca uuguuugaua aagauggugu gguacaauu      60 accaccaagg aauugggaac uguuaugaga agucuaagguc aaaauccaac agaagcggaa   120
uuacaagaua ugaucaauga aguugaugcc gaugguaaug guacuauuga uuuccugaa    180 uucuugacua ugaugggcuag aaaaaugaag gauacagacu cagaggagga aauccgugaa   240
gcuuuccgug uuuuugauaa agaugguaau gguuuuauuu cugcugcuga auugagacau   300
guaaugacca auuggguga aaaauugacc gacgaagaag uagaugaaau gauucgugaa    360
gccgauauug ac                                                        372
```

```
<210> SEQ ID NO 26
<211> LENGTH: 1114
<212> TYPE: DNA
<213> ORGANISM: Varroa destructor
<220> FEATURE:
<221> NAME/KEY: unsure
<222> LOCATION: (1)..(1114)
<223> OTHER INFORMATION: unsure at all n locations
<220> FEATURE:
<221> NAME/KEY: misc_feature
<222> LOCATION: (1100)..(1110)
<223> OTHER INFORMATION: n is a, c, g, or t

<400> SEQUENCE: 26
ggctcgtaca ccgagagaga acggtggact ccattgctgt cctgagtgcg tttctcgtcg     60
gctgtgtcgt attgcgtgtc tgtccgtgct ttcgtgcaca taagttttct ttccacattg    120
gagatattgt gaatagtatc ctttgtgttt agtgcctgaa caatatttga aatcgtcgaa    180
```

```
cgtatcaaga cataaaaacg agccaaaatg gctgatcaac ttacggaaga acaaatcgca      240
gaatttaagg aagcattttc actatttgat aaagatggag atggtaccat cacaactaaa      300
gagttgggta cagttatgcg atcactaggt caaaatccca cagaagctga gcttcaggat      360
atgattaatg aagttgatgc agatggtaat ggcacaatcg attttccgga attcttaact      420
atgatggctc gtaaaatgaa agatactgat agtgaggaag aaattaggga ggccttcaga      480
gtatttgata aggatggaaa tggtttcata tccgcagcag aactcagaca tgttatgaca      540
aatcttggcg agaaactcac tgatgaagaa gttgatgaaa tgattcggga ggctgacatt      600
gatggtgatg gccaagttaa ttatgaagaa ttcgtcacaa tgatgacatc aaagtgaatg      660
caacctgtgt aatggaaaaa cttgcaactt ggagtggtgt tgacgtatta agataaatca      720
agaaacaaag aaaatataaa tgttaacaaa aacgaatcg accagaaagt gaaaaaaatc      780
ttgtatctgg acgcaaagat gtctataaaa cgcgaaaaat taacgtccaa cacgcgttaa      840
tcatcattaa cgataagtaa tacagggcaa ttgtttaatt aaaagagtta taccactaaa      900
aatcattatc tctaaataca caaaacttaa ttacacaaca tgaacataaa aatacatatt      960
actcgcgcac atacatgaat acaaaaaaat atacagcaca cagaaatacc atctacataa     1020
aagataattt atttccgtat taaaaagtat ataattaaaa aatgttagag atatatatat     1080
ataatatata tatatatatn nnnnnnnnnn gtaa                                  1114

<210> SEQ ID NO 27
<211> LENGTH: 372
<212> TYPE: RNA
<213> ORGANISM: Varroa destructor

<400> SEQUENCE: 27
acaaaucgca gaauuuaagg aagcauuuuc acuauuugau aaagauggag augguaccau       60
cacaacuaaa gaguugggua caguuaugcg aucacuaggu caaaauccca cagaagcuga      120
gcuucaggau augauuaaug aaguugaugc agaugguaau ggcacaaucg auuuuccgga      180
auucuuaacu augauggcuc guaaaaugaa agauacugau agugaggaag aaauuaggga      240
ggccuucaga guauuugaua aggauggaaa ugguuucaua uccgcagcag aacucagaca      300
uguuaugaca aaucuuggcg agaaacucac ugaugaagaa guugaugaaa ugauucggga      360
ggcugacauu ga                                                         372

<210> SEQ ID NO 28
<211> LENGTH: 822
<212> TYPE: DNA
<213> ORGANISM: Varroa destructor

<400> SEQUENCE: 28
tttttttttt ttttcgaaga aatcgtatca tcgaacatcg gatcgaattt cgatccacga       60
cgctcgaatt acatgcaacg aagtgaatgt cagaggggggg ggggcagggg aaaagtatgc      120
gacgaacgtg tacgtccgtc gtccgctggc tcgtcgttaa ttcgttctat ctaacacaga      180
cacgagaata agtaagatcc tagtagcccg gggacagcac ctcctcctcc tcgtcctcct      240
cgtcgtcgtc gatccccggc tctccgagcg cgtggacgaa ttcgtagaaa tcgatacggc      300
cgtctccgtc cacgtccact tccttgatca tatcctcgat ctcttcttcc gacaagtcct      360
cgccgagaca ttgcagcact gccctcaaat cggatgcggt gatgtatcct cgattgtgtt      420
tatcgaatac ccggaacgca tccctcagct cctgctcttc ctgatcctga tccgtggggg      480
```

```
cggtttcatt cgcacctatg ttgctcacga tttccacgaa ctcttcgaag ctgacatttc    540
catccccgtc gatgtcgatc tcctgcaaca tggtgcgcag ctcctcggcc ctcgcgaatt    600
gccccaacga gcgcatcacc ctcccgagct cctccttcgt gatgctcccg tccccgtcct    660
tgtcgaacag tctgaacgct tccctgaatt ctttcatttg agatttggat atattgctcg    720
gtatcttggt ggacgactca gaggcggatt ttttcggcga cgcaggtaag gagaagagga    780
cgttggtcga caatttgccg gcctccgtgg acgaggaggc cg                       822
```

<210> SEQ ID NO 29
<211> LENGTH: 300
<212> TYPE: RNA
<213> ORGANISM: Varroa destructor

<400> SEQUENCE: 29

```
aacguguacg uccgucgucc gcuggcucgu cguuaauucg uucuaucuaa cacagacacg     60
agaauaagua agauccuagu agcccgggga cagcaccucc uccuccucgu ccuccucguc    120
gucgucgauc cccggcucuc cgagcgcgug acgaaauucg uagaaaucga uacggccguc    180
uccguccacg uccacuuccu ugaucauauc cucgaucucu ucuuccgaca aguccucgcc    240
gagacauugc agcacugccc ucaaaucgga ugcggugaug uauccucgau uguguuuauc    300
```

<210> SEQ ID NO 30
<211> LENGTH: 2577
<212> TYPE: DNA
<213> ORGANISM: Varroa destructor

<400> SEQUENCE: 30

```
ctgctgctgc tgctgctgct gctgctgccg tgttaagaac tagacaaagg caacaaccgg     60
aagacatctg ttaggccagt tgggtgaagg gaaataaact cgcaacaaag agctactgtt    120
gcaaaagcta tctgttctga gtcctagact agactgggat cgactaacaa ctctgcaggc    180
cgtggaccac tatcactgaa caacgccgca ggaccgagcg attgagaagt tggccgcggc    240
tgggacgctc tggctcactt gatctgatta ctacttacac caggtcaatt taaccaagcc    300
gttgaaccac tcctacatgg aaacacacat ctacactctc atccaattgt gtacacgcga    360
agcaaacgac aacggtatta gcagcgacac taacaaaaac gaatctgcca gaaaccgagt    420
aacgctgatt tctgcagcgg cgttcctacg aacttaccac agacccggtc ggcacaatag    480
tttgaaggtt agcatcggcc cgtgaactat agtgaaagga actgagcgaa atactatagt    540
tgttgaacag caggcttcaa agtaaagaag tgaatattct tatggtgaca acaaattttg    600
tctgtagtgg tcaagaccct actcaatgaa gtgagaagcg aattcatatg tgctcagtta    660
tagcagttgt ttgtcgtaat gccgccaata tacgacgtct gtgtgtctcg atactggcgt    720
atctgactga ttccgatcgg tgtcattgat ctgcaaagcc aattgttttc tttacgtccc    780
ggatagagca acgatcatg gcaacggaaa catttggcct gccggaggaa caggtggctg    840
aatttaaaga ggccttttctt ttgtttgaca aggacgccga tggaatgatt acggccgccg    900
aactaggcgt cgtcatgcga tcgcttggcc agcgacctac ggagcaagag ctcaagaaaa    960
tggttaccat ggttgaccag gacggcaatg gtacaatcga gttcaacgag ttttttgatga   1020 tgatgtctcg caagatgaag gaggcagact cggaggaaga actccgggag gcgttccgtg   1080
tgttcgatcg agacggtgac ggattcatct cgcgggacga gctcagtgtc gtcatgaaca   1140
acctcggcga gaaattaagt gacgatgatg ttgaggatat gattcgagag gccgatctgg   1200
acggcgatgg caagattaac taccaagagt ttgtgctcat tatcacctcc gccaagtagg   1260
```

-continued

```
ccttggagtt gctcgcgcac acacatgcta ttcctcttgt cctacacgac aaacactata    1320
cacgttacaa tacggaaaaa tgaaataaaa gcacagtcac acttattcat tcattcacag    1380
aggatcactg gcgtgtcctc attaatatgg ctgacaaata ctattgattt gtctcgactg    1440
agctatcagg cacacgcata ttgtctgttc cgatacgtgc aataataggt aaagtggtgt    1500
tagcttgagc accttacggt ttacatttat tccgtattaa cggtactatg tctcaatagt    1560
catgtcgcag cattagccag ctaacattaa atttagttga tttttatttt attttttac     1620 acaacaagaa ttatcttact atttggcaag ctgactgcga gtagtaaaat taccctagta    1680
aaaaaaaaag gctttaaaaa cgatttaaca aaggtgcgtc catttaaaaa agtatgacac    1740
aagctaatgt gttcgatcgc ggtcggttgc attcggccag tttgtgagac gcgaaattta    1800
ccagcagccg tcaacaacga tggaataatt atatattaaa tataaataat aaaatatctg    1860
ttacacattc tatgtgaata agttataca tatatatata catcaacag caatgatata     1920 tatgatgata cgtatactat atagaagtat ccactgatat aggataatgg gaaattctgg    1980
aaaggagaaa acatattctt ctttcataat taatgaatta tcatcgagca cctcaagaat    2040
ttgcttagac atattacaaa aaaaaaatta attcactata tataaataat cgcaattaat    2100
caaaaaaaaa atacggtcat ttatggcata ccctaggtta ataaacttca taaggtacc    2160 tatatatata tcttttttac tgtctcttta atcgtcatta tacatagtga cgattaaaga    2220
gagagagtaa aaagaggtc aaaataaaag acttgaagtc gattgaggtt aattttttatt    2280 ctaggttata tgtgttttag cggatttata gtgtgctcgt tgtaaaagtt gacgtaagga    2340
gttgaaacgc ggagagcagt ataacagtaa aatggagagg aagtttagaa gttgggaaat    2400
aaatgatttg ctactaattg gaaattacaa aaatgaccat ttaaagaact tatcattaga    2460
attttaatat ctgccacact gaaccgtttt gtcattattt cgaccatagc gattttcaca    2520
cagttgtctc acgtttgagg ccttatcgtt taaaggctaa cggaaatttc tctaaag       2577
```

<210> SEQ ID NO 31
<211> LENGTH: 373
<212> TYPE: RNA
<213> ORGANISM: Varroa destructor

<400> SEQUENCE: 31

```
acagguggcu gaauuuaaag aggccuuucu uuuguuugac aaggacgccg auggaaugau     60
uacggccgcc gaacuaggcg ucgucaugcg aucgcuuggc cagcgaccua cggagcaaga    120
gcucaagaaa auguuuacca ugguugacca ggacggcaau gguacaaucg aguucaacga    180 guuuugaug augaugucuc gcaagaugaa ggaggcagac ucggaggaag aacuccggga     240
ggcguuccgu guguucgauc gagacggugua cggauucauc ucgcgggacg agcucagugu    300
cgucaugaac aaccucggcg agaaauuaag ugacgaugau guugaggaua ugauucgaga    360
ggccgaucug gac                                                       373
```

<210> SEQ ID NO 32
<211> LENGTH: 693
<212> TYPE: DNA
<213> ORGANISM: Varroa destructor

<400> SEQUENCE: 32

```
cgcctctata cagtgaaaaa gtcggataag gttatgttac tcagtaactt aaccttatct     60
tggataacgt tatttgacac gtaaacgaaa agtaataaca aagttttgta ttatggctcg    120
```

```
ttattttcga gaggaagata tagatgaatt cagggaatgt ttttatctat ttgcaaggaa      180
tggtcaaata cgtactttgg atgagcttac aatcattatg agatcattag gattaagtcc      240
aactattgca gaattaaata aatatttgaa agataaaggt ggaaaaatgt cttttgccga      300
tttcttggaa gttatgcatc tacaaactag agctgaagat ttaccaaaag aagtgataga      360
tgcttttcaa gctgcagata aatttaggac tggcactata ccagctagac agttagcgca      420
tatgttactc cactgggtg aacaattaag taacaaagaa gtggagcaaa ttttcagaga       480
ggcaaatgtg tctccaaatg acaagtaaa gtacgaagat tttgttaaaa tagcttgtgc       540
acctgtacct gattactatt aaaataaata ttttttcatat tttttaaaga tatttatata    600 cttttacac aatacacacg tatttaatta ataaaaggat aaaaatgatc ataaaagaaa       660
aagaatttat tcttccagca acttatcttc gac                                   693

<210> SEQ ID NO 33
<211> LENGTH: 315
<212> TYPE: RNA
<213> ORGANISM: Varroa destructor

<400> SEQUENCE: 33
augcuuuuca gcugcagau aaauuuagga cuggcacuau accagcuaga caguuagcgc        60
auauguuacu ccacuggggu gaacaauuaa guaacaaaga aguggagcaa auuuucagag      120
aggcaaaugu gucuccaaau ggacaaguaa aguacgaaga uuuuguuaaa auagcuugug      180
caccuguacc ugauuacuau uaaaauaaau auuuucaua uuuuuuaaag auauuuauau      240
acuuuuuaca caauacacac guauuuaauu aauaaaagga uaaaaaugau cauaaaagaa      300
aaagaauuua uucuu                                                       315

<210> SEQ ID NO 34
<211> LENGTH: 612
<212> TYPE: DNA
<213> ORGANISM: Varroa destructor

<400> SEQUENCE: 34
cgttttttta atttcaaaga ctcctgattt tcttttcttt tcctttccta caaaccaaac       60
acaagctaga aagaggttcg atttttgcag gaagaagaag gaacaatggc tgatcagctc      120
accgatgacc agatctctga gtttaaggaa gccttcagcc tcttcgataa ggatggagat      180
ggttgtatca ccaccaagga gcttggaact gtgatgaggt ctcttggcca gaaccccact      240
gaggcagagc tccaggacat gatcaacgag gtggatgctg atggcaatgg aacaattgac      300
tttcctgagt tcttaaaccct catggccagg aagatgaagg atactgattc tgaggaggag      360
ctcaaggaag ctttccgcgt gtttgacaag gaccagaatg gcttcatttc tgcggctgag      420
ctccgccatg ttatgacgaa tcttggtgag aagctcacag acgaggaagt tgatgagatg      480
atccgtgagg ctgatgtaga tggtgacggc cagattaact acgaggagtt tgtcaaagtc      540
atgatggcca agtgaggatc attaaccaaa ccttaaaatt tcgaaagcat aaacatttaa      600
aaaaaaaaaa aa                                                          612

<210> SEQ ID NO 35
<211> LENGTH: 371
<212> TYPE: RNA
<213> ORGANISM: Varroa destructor

<400> SEQUENCE: 35
cagaucucug aguuuaagga agccuucagc cucuucgaua aggauggaga uggüuguauc        60
```

```
accaccaagg agcuuggaac ugugaugagg ucucuuggcc agaaccccac ugaggcagag    120
cuccaggaca ugaucaacga gguggaugcu gauggcaaug aacaauuga cuuccugag     180 uucuuaaacc ucauggccag gaagaugaag gauacugauu cugaggagga gcucaaggaa    240 gcuuccgcg uguuugacaa ggaccagaau ggcuucauuu cugcggcuga gcuccgccau    300
guuaugacga aucuugguga gaagcucaca gacgaggaag uugaugagau gauccgugag    360
gcugauguag a                                                         371

<210> SEQ ID NO 36
<211> LENGTH: 659
<212> TYPE: DNA
<213> ORGANISM: Ixodes scapularis

<400> SEQUENCE: 36
acaccgcgct cgacgagaac tcgcgcaagg agcgcgtgct aacgccgata gctctcgtac    60
aaaagaaaac taaagacttg acacgctcaa taccgatctt tcacattttc agcaaaattt   120
gagcattccg aatatggacc tgactccgga agagatcgcg gacatcaagg gagcgtttct   180
gctgtttgac cgcaacggcg acggaaccat ctccacgact gagctagaga tggtcctccg   240
cgccatgggc gaacggccca gtccttccca gctggcccgt atagtgcggc aaattgacag   300
cgaccgcaat ggaagcatcg acttccaaga gtttctcttt ttcatggccg gcaggatttc   360
ccacaaaggc ctctccaaaa gcgcagtcct caaggccttc caactcttcg accgcgatgg   420
caatggatac atcaccaggg aggaactcgt ccacattttc acgcacgttg ggcagagcat   480
gagccaagaa gacgccgaaa agataatccg cgaagtggat gtggacaagg acggaaagat   540
ccattacact gaattggtca caaggtgct gcccaccaag aagcaaaaag aagaaaccaa    600
aacctagaag gtcgtcgctt ggcacggtct ttattattaa acaagtgctt tatcgcttg    659

<210> SEQ ID NO 37
<211> LENGTH: 374
<212> TYPE: RNA
<213> ORGANISM: Ixodes scapularis

<400> SEQUENCE: 37
agaucgcgga caucaaggga gcguuucugc uguuugaccg caacggcgac ggaaccaucu    60
ccacgacuga gcuagagaug guccuccgcg ccaugggcga acggcccagu ccuucccagc   120
uggcccguau agugcggcaa auugacagcg accgcaaugg aagcaucgac uuccaagagu   180
uucucuuuuu caguggccggc aggauuuccc acaaaggccu cuccaaaagc gcaguccuca   240
aggccuucca acucuucgac cgcgauggca auggauacau caccagggag gaacucgucc   300 acauuucac gcacguuggg cagagcauga gccaagaaga cgccgaaaag auaauccgcg    360
aaguggaugu ggac                                                     374

<210> SEQ ID NO 38
<211> LENGTH: 549
<212> TYPE: DNA
<213> ORGANISM: Ixodes scapularis

<400> SEQUENCE: 38
gattcgtcca cttattttgt ccctattctt cgtccgcagt cgtcctcgag gaaaagtgcg    60
tcaggtgcgg gctacaagcg gaaactgagc ggaaagccag aaccgagcga ggagcagaag   120
aatgacatga aggaagcgtt cagtctcttc gatcccagtg gcacgggctt catggagtct   180
```

| | |
|---|---|
| aaagatatga agtttgcaat gagagcactg ggttttgaac caaaaaagga ggaagtgaaa | 240 |
| aaactgatag cagagattga caagcagggg actggaaaaa ttcccttgga ggagttcatg | 300 |
| agcgtcatgt ccacgaggct ggctgagaaa gacataaatg aggagattat gaaggcgttt | 360 |
| cagctgtttg atgaggatgg cactgggaag atttctttta agaacctcaa gaatgtggcc | 420 |
| aaggaactgt cggagaacct cacagatgag gagcttcagg aaatgatcaa tgaagctgac | 480 |
| agggatggag atggcgaagt gaaccaagag gagttcctta ggataatgaa gaagacctgc | 540 |
| ctctactga | 549 |

<210> SEQ ID NO 39
<211> LENGTH: 373
<212> TYPE: RNA
<213> ORGANISM: Ixodes scapularis

<400> SEQUENCE: 39

| | |
|---|---|
| ugaaggaagc guucagucuc uucgauccca guggcacggg cuucauggag ucuaaagaua | 60 |
| ugaaguuugc aaugagagca cuggguuuug aaccaaaaaa ggaggaagug aaaaaacuga | 120 |
| uagcagagau ugacaagcag gggacuggaa aaauucccuu ggaggaguuc augagcguca | 180 |
| uguccacgag gcuggcugag aaagacauaa augaggagau uaugaaggcg uuucagcugu | 240 |
| uugaugagga uggcacuggg aagauuucuu uuaagaaccu caagaaugug gccaaggaac | 300 |
| ugucggagaa cccuacagau gaggagcuuc aggaaaugau caaugaagcu gacagggaug | 360 |
| gagauggcga agu | 373 |

<210> SEQ ID NO 40
<211> LENGTH: 234
<212> TYPE: DNA
<213> ORGANISM: Ixodes scapularis

<400> SEQUENCE: 40

| | |
|---|---|
| atggccaaga acgtccgcgc cctggacacc gaggaggaga ttttggaggc cttcaaagtc | 60 |
| ttcgaccgca acggcgacgg cttcgtgagc acagccgagc tccgtcacgt gatgaccacg | 120 |
| ttaggcgaga agttgacgca cgaagaagtg gacgagatga tccgcgaggc cgaccgcgac | 180 |
| ggcgacggac agatcaacta cgacgagttc gtggccatga tgacttccaa gtga | 234 |

<210> SEQ ID NO 41
<211> LENGTH: 213
<212> TYPE: DNA
<213> ORGANISM: Ixodes scapularis

<400> SEQUENCE: 41

| | |
|---|---|
| cctggaaccg aggaggagat tctggaggcc ttcaaagtct tcgaccgcaa cggcgacggc | 60 |
| ttcgtgagca cggccgagct ccgtcacgtg atgaccacgc taggcgagaa gttgacgcac | 120 |
| gaagaagtgg acgagatgat ccgcgaggcc gaccgtgacg gcgacggaca gatcaactac | 180 |
| gacgagttcg tggccatgat gacctccaag tga | 213 |

<210> SEQ ID NO 42
<211> LENGTH: 200
<212> TYPE: RNA
<213> ORGANISM: Ixodes scapularis

<400> SEQUENCE: 42

| | |
|---|---|
| gaggaggaga uucuggaggc cuucaaaguc uucgaccgca acggcgacgg cuucgugagc | 60 |
| acggccgagc uccgucacgu gaugaccacg cuaggcgaga aguugacgca cgaagaagug | 120 |

```
gacgagauga uccgcgaggc cgaccgugac ggcgacggac agaucaacua cgacgaguuc    180
guggccauga ugaccuccaa                                                200
```

<210> SEQ ID NO 43
<211> LENGTH: 450
<212> TYPE: DNA
<213> ORGANISM: Aedes aegypti

<400> SEQUENCE: 43

```
atgtccgccc atagtctaac agaggaacaa gggcgccagt tccgtcagat gttcgagatg     60
ttcgacaaaa atggcgacgg ttcgatcagc acatcggaac tgggatcggt cattcgggcc    120
ttgggtatga atccctccat tgcggaaatc gagcaaatga tccacgaggt cgatttggac    180
ggaagtgggt cgattgagtt gaacgaattt ctcatactga tggcacgtaa gtcacgggag    240
ggttccacac aggaagagct acgggatgcg ttcaaaattt ttgacaagga tggagatgga    300
tttctcacgg ttgacgagtt gtcggctgtt atgaagaact tggcgagag attgaccgat    360 gacgaactag cagatctgct ggaggaagcc gacatcgatg gagacggaaa gatcaactat    420
gaagaatttg tcatcatgtt gagcaagtga                                     450
```

<210> SEQ ID NO 44
<211> LENGTH: 300
<212> TYPE: RNA
<213> ORGANISM: Aedes aegypti

<400> SEQUENCE: 44

```
acagaggaac aagggcgcca guccgucag auguucgaga uguucgacaa aaauggcgac     60
gguucgauca gcacaucgga acugggaucg gucauucggg ccuugggau gaaucccucc    120 auugcggaaa ucgagcaaau gauccacgag gucgauuugg acggaagugg gucgauugag    180
uugaacgaau uucucauacu gauggcacgu aagucacggg agggguccac acaggaagag    240 cuacggggaug cguucaaaau uuuugacaag gauggagaug gauuucucac gguugacgag    300
```

<210> SEQ ID NO 45
<211> LENGTH: 465
<212> TYPE: DNA
<213> ORGANISM: Aedes aegypti

<400> SEQUENCE: 45

```
atgtccgccc aaaccccgcc agacaagctt tcccaggatc aaatcgaaga actgcgggaa     60
gctttctccc tgttcgacac caacggcgac ggaaccataa cctgttcaga acttggcaca    120
gtccttcgat cccttggcaa aaatgtatcc gacgcggaag tggaagaact gctcaaagaa    180
gtcaacgtcg accacgaagg aatgatccac tttccggact cgtggcaat gatgtccatc    240 cgattgcggg acttcaatag cgaggaggaa ctcaaggaag ccttccggat cttcgaccgc    300
aacggagatg ggctgatttc ggcggacgaa ttgcgagcgg ctctccaatc tttcggggaa    360
cagctggccg aggaggaaat cgaagaactg ctccgggagg cggatgtcaa ctgcgacgga    420
caaatagact acgaggagtt tgttaaaatg atcacgctga aataa                    465
```

<210> SEQ ID NO 46
<211> LENGTH: 300
<212> TYPE: RNA
<213> ORGANISM: Aedes aegypti

<400> SEQUENCE: 46

```
caaaucgaag aacugcggga agcuuucucc cuguucgaca ccaacggcga cggaaccaua    60
accuguucag aacuuggcac aguccuucga ucccuuggca aaaauguauc cgacgcggaa   120
guggaagaac ugcucaaaga agucaacguc gaccacgaag gaaugaucca cuuccggac    180 uucguggcaa ugauguccau ccgauugcgg gacuucaaua gcgaggagga acucaaggaa   240
gccuuccgga ucuucgaccg caacggagau gggcugauuu cggcggacga auugcgagcg   300
```

<210> SEQ ID NO 47
<211> LENGTH: 1150
<212> TYPE: DNA
<213> ORGANISM: Aedes aegypti

<400> SEQUENCE: 47

```
tcgtcaagga tatccggcaa ctgattatga cccggcaaac caacgatccc aacggccagc    60
aacaggaaca gaacgaacca gaatccagtc agaacaccca gagcgaccaa agcaacaacc   120
agcccacgca gcgattggga ggaaccacct cggacttcag tgtcagctcc gcggccacta   180
atcgaagtat gccccgccac caggaggaca atcccaatca accggccagc gactgttcca   240
gcctcgaggg aaatgtattc gtcgaaggcg gatccggcac cggagcgcac ccgaaaacac   300
gccgctcgca aacttccgat tcgatcacct ccagcaactt caactacagt ctcaaccgga   360
ggttcatatc gaagaaccag atgaaggagt ttcgagaagc gttccggctg ttcgacaagg   420
ataatgacgg ctcaatcacc aaggaagaac tgggaactgt catgaggtcg ttgggacaat   480
ttgctcgcgt ggaagaatta caagagatgt tactggagat tgatgttgat ggcgatggaa   540
acgtaagttt cgaagagttt gtcgacatca tgtccaacat gacggatacc gtggcggaaa   600
catcggccga ccaggaggaa cgtgagctac gtgatgcctt ccgtgtcttc gacaagcaca   660
atcgaggtta cattacggca tcagatctac gggcggttct tcaatgtctg ggcgaagatt   720
tggatgaaga agaaattgaa gacatgatca agaagtgga cgtggatgga gacggacgga    780
tcgatttcta cgaattcgta catgctcttg gagaaccgga agattcccaa gaaaacgacg   840
acgaagacga ggcagtgtcc ccccattcgc tgtcctgtga cgtgcatgtc taagaaccgc   900
caggagaaaa atagctaacg ccaacgaatc gcattcctaa caaaatgtcg aacaatctag   960
agacattgac cagatttttt ttaaatattt aacacacaaa aaaacttcgc ttaacgccat  1020
tgtacttctc catacgcttg ataacagatt ccagaacacc taatgaattt atcaatctat  1080
acataataac tattcatctc taatcacgaa aaaagtttaa ataaacatat caaattgagc  1140
aaccaataag                                                         1150
```

<210> SEQ ID NO 48
<211> LENGTH: 300
<212> TYPE: RNA
<213> ORGANISM: Aedes aegypti

<400> SEQUENCE: 48

```
gaguuucgag aagcguuccg gcuguucgac aaggauaaug acggcucaau caccaaggaa    60
gaacugggaa cugucaugag gucguuggga caauuugcuc gcguggaaga auuacaagag   120
auguuacugg agauugaugu ugauggcgau ggaaacguaa guuucgaaga guuugucgac   180 aucauguca acaugacgga uaccguggcg gaaacaucgg ccgaccagga ggaacgugag   240
cuacgugaug ccuuccgugu cuucgacaag cacaaucgag guuacauuac ggcaucagau   300
```

<210> SEQ ID NO 49
<211> LENGTH: 450

```
<212> TYPE: DNA
<213> ORGANISM: Culex quinquefasciatus

<400> SEQUENCE: 49
atgtcggccc actcgctcac cgacgaacag cagcgccagt accggcaaat gttcgaaacg      60
ttcgacaagg atggcaacgg ttccatcacg acgacggaac tgggaacgct agtgcgagcg     120
ctaggtctta atccttcgat cgccgagatc gagcagatga tccacgaggt cgacctggac     180
ggaagcggga cgatcgagct gaacgagttt tacgtgctga tggcccggaa gcatcgggaa     240
gcctcgtcgg aggacgagct gaggcaggct ttcaaggtgt ttgacaagaa cgaggatggg     300
ttcttgacgg tggaggaact gtcgatggtg atgaagaact tggtgagcg gttgagcgat      360 gaagagttgg cggatttgtt ggaggaggcg gatgttgaca aggacggtcg gattaattac     420
gaggaatttg tgaccatgtt gaccaagtag                                      450

<210> SEQ ID NO 50
<211> LENGTH: 300
<212> TYPE: RNA
<213> ORGANISM: Culex quinquefasciatus

<400> SEQUENCE: 50
acagcagcgc caguaccggc aaauguucga acguucgac aaggauggca acgguuccau       60
cacgacgacg gaacugggaa cgcuagugcg agcguaggu cuuaauccuu cgaucgccga     120
gaucgagcag augauccacg aggucgaccu ggacggaagc gggacgaucg agcugaacga     180
guuuuacgug cugauggccc ggaagcaucg gaagccucg ucggaggacg agcugaggca     240
ggcuuucaag uguuugaca agaacgagga uggguucuug acgguggagg aacugucgau     300

<210> SEQ ID NO 51
<211> LENGTH: 477
<212> TYPE: DNA
<213> ORGANISM: Culex quinquefasciatus

<400> SEQUENCE: 51
atgtcatcgt cttcccgcca ccccaaaccc accgcggacc ccctgaccaa ggagcaaatc      60
gaagaactgc gcgaagcgtt caccctgttc gacaccaacg cgacggaac gatttccggc     120 tcggaactgt ccaccgtgct gcgggccctc ggcaagaacg tctcggacgc cgaagtcgag     180
gaactgctga aggaggtccg caccgacgac gagggccgca tccggttcgg ggactttgtg     240
gccatgatga cggtccggtt gaaggacttt aacaacgagg accagctgca ggaggcgttt     300
cggatcttcg atcgggacgg gaatgggcgg atttcggcgg aagagctacg ggtcgcgttg     360
aggtcgtttg gggagcagtt gaccgaagag gagctggagg agttgctgcg cgaggcggac     420
gtcaacagtg acggccagat tgactacggg gagtttgtgc ggatgataac gcagtga       477

<210> SEQ ID NO 52
<211> LENGTH: 300
<212> TYPE: RNA
<213> ORGANISM: Culex quinquefasciatus

<400> SEQUENCE: 52
gcgaagcguu caccccuguuc gacaccaacg gcgacggaac gauuuccggc ucggaacugu     60
ccaccgugcu gcgggcccuc ggcaagaacg ucucggacgc cgaagucgag gaacugcuga     120
aggaggugcg caccgacgac gagggccgca uccgguucgg ggacuuugug gccaugauga     180
cgguccgguu gaaggacuuu aacaacgagg accagcugca ggaggcguuu cggaucuucg     240
```

```
aucgggacgg gaaugggcgg auuucggcgg aagagcuacg ggucgcguug aggucguuug    300
```

<210> SEQ ID NO 53
<211> LENGTH: 927
<212> TYPE: DNA
<213> ORGANISM: Culex quinquefasciatus

<400> SEQUENCE: 53

```
atgaccgatt ttctccagct tccccaatgc aatactcgac aaaccaacga cccaaacagc     60
gccgagcagc aacaacagag cgaacccgaa tcgaaccaga gcagcacgca ccagagcagc    120
agccacagct accagcagcc gtcgtcaacg cagcaccggt tggccggatc tccgtcgagc    180
agtgccaacg cgagtcccgt gatcggccgg aacatgcccc gccaccagca ccaggacacc    240
gcgcccagtg acgatgggac ctcgagcagt ctggacggga gtgtctttgc cgccgacgga    300
actccgaccg ctccggggc gttggccagg acgcgccgct cgcagacctc ggaatcgatc    360
acctccagca acttcaacta cagtttgaac cggaggttca tctccaagaa ccagatgaaa    420
gagttccggg aggcgttccg gctgtttgac aaggacaacg acgggtcgat cacgaaggag    480
gagctgggca cggtgatgcg atcactgggg cagtttgccc gtgtcgagga actgcaggag    540
atgctgctgg agattgacgt cgatggtgat ggcaacgtca gcttcgagga gtttgtcgac    600
atcatgtcca acatgaccga cacggtggcg gaggcatccg ccgaccagga ggagcgcgaa    660
ctccgggatg cgttccgcgt gtttgacaag cacaaccggg gctacatcac ggcgtctgat    720
ctgcgggcgg ttctgcagtg tctgggagaa gatttggacg aggaagaaat cgaagacatg    780
atcaaggagg tggacgtcga cggcgatgga cggatcgact tttacgagtt tgtgcacgcc    840
ctcggagagc cggaagattc acaggagaac gacgacgagg aggacccccct gtcacctccg    900
tcactgtcgt gtgacgtaaa cgcctaa                                        927
```

<210> SEQ ID NO 54
<211> LENGTH: 300
<212> TYPE: RNA
<213> ORGANISM: Culex quinquefasciatus

<400> SEQUENCE: 54

```
gaguuccggg aggcguuccg gcuguuugac aaggacaacg acggguccau cacgaaggag     60
gagcugggca cggugaugcg aucacugggg caguuugccc gugucgagga acugcaggag    120
augcugcugg agauugacgu cgauggugau ggcaacguca gcuucgagga guuugucgac    180
aucaugucca acaugaccga cacgguggcg gaggcauccg ccgaccagga ggagcgcgaa    240
cuccgggaug cguuccgcgu guuugacaag cacaaccggg gcuacaucac ggcgucugau    300
```

<210> SEQ ID NO 55
<211> LENGTH: 333
<212> TYPE: DNA
<213> ORGANISM: Culex quinquefasciatus

<400> SEQUENCE: 55

```
atggtcggtg tccaagctgg ccatttgata tctcaatcac ggcggggcgg ctccgcgtgc     60
gaaaacgggg aaattttgat tgatgacggc ggcggcgggg agcggcgggt tttaaacctg    120
ttctacaagg ggaataaaaa tgccgatcaa cttacagagg aacagatcgc cgagttcaaa    180
gaagcgttct cgctgttcga caaagacggt gacggcacga tcacgaccaa ggagctgggc    240
accgtgatgc gatcgttagg ccagaaccc acagaagcag agctgcaaga catgataaac    300
gaggtcgatg cggacggact gcatccgctt taa                                 333
```

<210> SEQ ID NO 56
<211> LENGTH: 300
<212> TYPE: RNA
<213> ORGANISM: Culex quinquefasciatus

<400> SEQUENCE: 56 gucgguguccc aagcuggcca uuugauaucu caaucacggc ggggcggcuc cgcgugcgaa     60 aacgggaaa uuuugauuga ugacggcggc ggcggggagc ggcggguuuu aaaccuguuc    120 ucaagggga auaaaaaugc cgaucaacuu acagaggaac agaucgccga guucaaagaa    180
gcguucucgc uguucgacaa agacggugac ggcacgauca cgaccaagga gcugggcacc    240
gugaugcgau cguuaggcca gaaccccaca gaagcagagc ugcaagacau gauaaacgag    300

<210> SEQ ID NO 57
<211> LENGTH: 934
<212> TYPE: DNA
<213> ORGANISM: Acyrthosiphon pisum

<400> SEQUENCE: 57
gctgtgcacg ttttgtttac ccgaaaaatg tgattcaaac tttcagtttt ttaaatctta     60
actgcgttgt ttaagaaaaa aaaaaccta aatttattat tgtttattaa taataaatca    120
atcgatcgaa taatcgtttg cgggtatacc taagtacgaa gtaaaatatg agtgcacaaa    180
atagtgataa tgaccgttat aaaaaggaat attcgagaat aaggaaactg acgagtagat    240 atgcatacg gactcaatca aatgaatttg gtttgtcgga agatcaagtt gcggaattca    300
aagaagcatt tatgttgttc gataaagacc atgatggacg gattactgag gcagaactag    360
gagtggtcat gagatcttg ggtcaaaggc ctactgaaac tgatttgcga ggtatggtta    420
aagaagtgga taaagatggc aatggtagta ttgagtttga tgaattcctg ctaatgatgg    480
ctagaaaact aaaagcagca gatggcgagg aagaaatgca ccaagctttt aaagtatttg    540
acaaaaatgg cgatggattc ataacatttg atgaactcaa acgtgttatg tgcagtatcg    600
gagaaaggct cactgatgaa gaaattgagg acatgataaa agaagcagat ttaaatggtg    660
ataaaaaaat tgattataaa gaatttatta caataataag ttctaagaaa taaaacgaat    720
tacggacttg gatgtacccct catatggcat tcgttcctca tctgcatctg tgtcattggc    780
tgctaagact ttacttaata ataaaccttg atcttctcta ctagaataaa atagctctgg    840
atcctaaagt aaaatataca gtataatttt aaaatagtcg tatacaaatt tttttttaaa    900
tattgagtgt acctcatcca ttccagcaag tttc                                 934

<210> SEQ ID NO 58
<211> LENGTH: 372
<212> TYPE: RNA
<213> ORGANISM: Acyrthosiphon pisum

<400> SEQUENCE: 58
ucaaguugcg gaauucaaag aagcauuuau guuguucgau aaagaccaug auggacggau     60
uacugaggca gaacuaggag uggucaugag aucuuugggu caaaggccua cugaaacuga    120
uuugcgaggu augguuaaag aaguggauaa agauggcaau gguaguauug aguuugauga    180
auuccugcua augauggcua gaaaacuaaa agcagcagau ggcgaggaag aaaugcacca    240
agcuuuuaaa guauuugaca aaaauggcga uggauucaua acauuugaug aacucaaacg    300
uguuaugugc aguaucggag aaaggcucac ugaugaagaa auugaggaca ugauaaaaga    360
agcagauuua aa 372

<210> SEQ ID NO 59
<211> LENGTH: 2509
<212> TYPE: DNA
<213> ORGANISM: Acyrthosiphon pisum

<400> SEQUENCE: 59

| | | | | | |
|---|---|---|---|---|---|
| gattttcgt | ttaaataacc | cccccgggtt | tcggataaac | tcggtgtgcg | tgtggacgcc | 60 |
| gccgccgccg | cgtgagcgtt | atttcgctcg | ctgtgattac | gaacgctcgt | gcagtcgtcg | 120 |
| tcatgcagca | tctccgagac | ccggcgaaag | accatcagag | tacgtgaaca | ctgcacatca | 180 |
| cactccatcg | cgatatactt | atctgtagga | cgacacccctt | taccgaggac | acaatgatat | 240 |
| acacgttata | atactatcgt | acatcgtata | tattgtattc | ttatcatcta | atattatatt | 300 |
| atcacaatcg | ttatattgta | ttatagaatt | attgtatatc | gttttaattt | gacacgatac | 360 |
| gacatttggt | gttgagaatc | gcgcagagag | agaaagagag | agagaaaaag | agagaataga | 420 |
| tattttgatg | taaataatta | ttacaatata | atattgtatt | tgaaaataga | aacagataat | 480 |
| tggtcgttga | ggcagttctc | accttttttaa | gatatacata | ttatattata | tataaacagt | 540 |
| attttgtttt | actcctttga | gtgaacattt | cgtttaacta | taccacaatt | tattaatatt | 600 |
| atataatatc | tatcatggac | ggtaaaatat | catcggtatt | cgaaaaatac | ttttcacctt | 660 |
| caccgctggt | gaaccaaata | aggaattttg | tcaatcggca | aatagacgag | caaacgccac | 720 |
| aaaacgtaag | cacacaacca | accgctgtag | cgaaacttca | cagtaataat | gtagtgaacg | 780 |
| gcaccactcc | gaaacccatc | acaagcaacg | aaaaaccaac | ggaagtccaa | gtacatccac | 840 |
| aacccactca | gcctgccgat | agaaacttag | tgcacgttac | taaagcacag | atgaaagaat | 900 |
| ttcaagaagc | atttaggtta | tttgataaag | acggtgacgg | cagcatcact | aaagaggaat | 960 |
| tgggtcgagt | tatgcggagt | cttggacagt | ttgctagaga | agaagaattg | gagacaatgt | 1020 |
| tacaagaagt | cgacatcgat | ggcgatggag | cgttcagttt | tcaagagttt | gtagaaattg | 1080 |
| tgtacaatat | gggtggtaca | gcagaaaaga | cggcggacca | agaggaaaaa | gagctccgag | 1140 |
| acgcatttag | ggtatttgac | aaacataacc | gaggatatat | aagtgcgtcg | gacttgagag | 1200 |
| ctgtccttca | atgtttgggt | gaagatttgt | cagaagaaga | aatcgaggat | atgatcaagg | 1260 |
| aagtagacgt | ggacggagat | ggaagaatcg | attttttacga | atttgtgaat | gcccttggag | 1320 |
| aaccaggaga | tgattatgat | gaaaacgacg | aagatgaaga | agatatttat | ccccaattgg | 1380 |
| acattcaaac | ataacttata | aacaattaca | cgttttagta | tgatgcgata | acaagttcag | 1440 |
| ttaaaattga | attatcaaaa | atgataacaa | tatttttgt | aaacttaggt | taaaatgtta | 1500 |
| aaaacttacc | cattttgtaa | tttctatcag | gaataaacac | accaatatct | gtttttttt | 1560 |
| tgccaactaa | tgatctctaa | taagtaaaac | atatttact | ttaatatcaa | tgtactactg | 1620 |
| tagtattgtt | aagtaattta | tgtcattttc | aatgtttaat | gtataaatta | atcatttaat | 1680 |
| ggtacaatca | gtaattcacc | ttaagaccca | attatttatt | aaaaacatat | tatatcatta | 1740 |
| atttacttaa | tgtatacatt | ttagtcaaaa | acattcagt | tatatgttat | aagtcgttat | 1800 |
| aactatttat | ttaagaaact | ataaaaaatt | attatttatt | ataatagttt | acgtatctat | 1860 |
| ttacttccat | ggaaggtatt | tataaataga | aaatgttaag | gtaacttaat | taaaacaata | 1920 |
| attatgaaca | gtatttttta | ctttaaaaaa | attacataat | tatattgtca | gtattctttc | 1980 |
| aaatacaatt | aattcaaatt | tgtgaaattg | tccattcctc | ctttatgctt | tgtgaactaa | 2040 |
| atttaaatac | attaagaacc | agagtacaat | taaaggaaat | agtcagctgc | gtgttttttt | 2100 |

```
gttggcattc ctcggttttc ttgtggtgct gcctcaaata ttgtaaaatc tctttgaagt    2160
gtttcactga gttccaatat tgccgcaacg ttaccacatc tattatttac aattagtatt    2220
aacaattaaa taacagcatt aataaataaa tagtataatg taattttttag agtagtattt    2280 accgataaca atagttgggt gctgaccaaa cagtaagcac ggtttcatca aaatgccatt    2340
tatatccttc catgactagt tgatgagctc gacaaataat atctatatca tttgtagtat    2400
taaactggga gacaacatca gaaccaaata ggtatccagc accccgagga ctcacacccc    2460
atccctgagt atctaaaata attgtgtatg ttaaaaatct attttttttt              2509
```

<210> SEQ ID NO 60
<211> LENGTH: 294
<212> TYPE: RNA
<213> ORGANISM: Acyrthosiphon pisum

<400> SEQUENCE: 60

```
acagaugaaa gaauuucaag aagcauuuag guuauuugau aaagacggug acggcagcau     60
cacuaaagag gaauuggguc gaguuaugcg gagucuugga caguuugcua gagaagaaga    120
auuggagaca auguuacaag aagucgacau cgauggcgau ggagcguuca guuuucaaga    180
guuuguagaa auuguguaca auaugggugg uacagcagaa aagacggcgg accaagagga    240
aaaagagcuc cgagacgcau uuaggguauu ugacaaacau aaccgaggau auau          294
```

<210> SEQ ID NO 61
<211> LENGTH: 477
<212> TYPE: DNA
<213> ORGANISM: Pediculus humanus

<400> SEQUENCE: 61

```
atggccgacg aaacgacgac ggaattaccg gaggaaaatc tttcggttga aaaaatcgca     60
gaattccgcg aagcttttcaa cctttttcgac aaagatggcg acggtaacat aacgaccaaa   120
gaattgggta cttgcatgag gtctctcggg cagaatccga cggaagcgga aatcgcggag    180
ctgatttgcg aagtagacgt agagggaaca ggtttaatcg atttcacatc gttcgttttg    240
ataatggcta aaaagataaa agacgtcgac aacgaggaag aactcagaga gcttttttaga   300 atattcgata aggaaggtaa cggattcata accgcatccg agctcaggca cataatgatg    360
aacttgggtg aaaaattaac ggaagaagaa tgcgacgaaa tgattaggga gcggatgtc    420 atgggtgacg gaaatatcaa ttacgaagaa ttcgtcacca tgatgatgtc aaagtga      477
```

<210> SEQ ID NO 62
<211> LENGTH: 379
<212> TYPE: RNA
<213> ORGANISM: Pediculus humanus

<400> SEQUENCE: 62

```
aaaaaucgca gaauuccgcg aagcuuucaa ccuuuucgac aaagauggcg acgguaacau     60
aacgaccaaa gaauugggua cuugcaugag gucucucggg cagaauccga cggaagcgga    120
aaucgcggag cugauuugcg aaguagacgu agagggaaca gguuuaaucg auuucacauc    180
guucguuuug auaauggcua aaaagauaaa agacgucgac aacgaggaag aacucagaga    240
agcuuuuaga auauucgaua aggaagguaa cggauucaua accgcauccg agcucaggca    300
cauaaugaug aacuuggugu gaaaaauuaac ggaagaagaa ugcgacgaaa ugauuaggga    360
agcggauguc auggguguac                                                379
```

<210> SEQ ID NO 63
<211> LENGTH: 537
<212> TYPE: DNA
<213> ORGANISM: Pediculus humanus

<400> SEQUENCE: 63

| | | | | | | |
|---|---|---|---|---|---|---|
| atggatgcta | ggaatgaagt | ttacaacacc | gaatataatc | gtttaagaaa | attgacgtgt | 60 |
| agaacggaaa | ttaaattatc | ttgctctgaa | tatggtctta | cggaggaaca | agtcgctgaa | 120 |
| tttaagaag | cttttatgct | ttttgacaaa | gatgaagatg | gacaaataac | aatggccgaa | 180 |
| ttaggagtcg | ttatgagatc | tttgggacaa | cgtccgacag | aaacggaatt | aagagacatg | 240 |
| gttaaagagg | ttgatcaaga | tggaaatggt | acaatcgaat | tcaatgaatt | tttacaaatg | 300 |
| atggcaaaaa | aaatgaaagg | agctgatggt | gaagaagaac | ttcgagaagc | attcagggtg | 360 |
| tttgataaaa | ataacgatgg | actcatttca | tccattgaac | ttcgacatgt | catgacaaat | 420 |
| ttaggtgaga | aactttcaga | cgaagaagtt | gatgatatga | taaagaagc | agatttagat | 480 |
| ggagatggta | tggttaacta | caatgaattt | gtaacgatat | taacatcaaa | aaattaa | 537 |

<210> SEQ ID NO 64
<211> LENGTH: 417
<212> TYPE: RNA
<213> ORGANISM: Pediculus humanus

<400> SEQUENCE: 64

| | | | | | | |
|---|---|---|---|---|---|---|
| acaagucgcu | gaauuuaaag | aagcuuuuau | gcuuuugac | aaagaugaag | auggacaaau | 60 |
| aacaauggcc | gaauuaggag | ucguuaugag | aucuuuggga | caacguccga | cagaaacgga | 120 |
| auuaagagac | augguuaaag | agguugauca | agauggaaau | gguacaaucg | aauucaauga | 180 |
| auuuuuacaa | augauggcaa | aaaaaaugaa | aggagcugau | ggugaagaag | aacuucgaga | 240 |
| agcauucagg | guguuugaua | aaauaacga | uggacucauu | ucauccauug | aacuucgaca | 300 |
| ugucaugaca | aauuuaggug | agaaacuuuc | agacgaagaa | guugaugaua | ugauaaaaga | 360 |
| agcagauuua | gauggagaug | guaugguuaa | cuacaaugaa | uuuguaacga | uauuaac | 417 |

<210> SEQ ID NO 65
<211> LENGTH: 648
<212> TYPE: DNA
<213> ORGANISM: Pediculus humanus

<400> SEQUENCE: 65

| | | | | | | |
|---|---|---|---|---|---|---|
| atgactacga | aacataatat | atctggaaga | atacgggacg | aaccagggg | acaaagggaa | 60 |
| aaaaatggaa | atgtaaccgg | tcgaacaata | acatatccaa | caacagggaa | caaaagaaat | 120 |
| attgataaca | tgacgaaaaa | taacatatca | aaatcgcaaa | tgaaggaatt | tcgagaagct | 180 |
| tttcgacttt | ttgacaaaga | tggtgatggt | agtataactc | aagaagaact | tggaagagtt | 240 |
| atgagatctt | taggacaatt | tgccagagaa | gaagaactac | aagaaatgct | taaggaagtt | 300 |
| gatatagatg | gagatggaaa | ttttagcttt | gaagaatttg | ttgaaatcgt | atcaaatatg | 360 |
| ggaggtgcag | caactgaaaa | aacagctgat | gaagaagaga | agaacttag | agatgctttt | 420 |
| agagtatttg | ataaacataa | tcgaggtttt | ataagtgctt | ctgatcttcg | agctgttttg | 480 |
| caatgtctgg | gtgaagaatt | atcagaagaa | gaaaaaatga | taagagaagt | tgatgtggat | 540 |
| ggagatggta | gaattgattt | tttcgaattt | gttcgagctt | tgggtacaca | ctacaggcaa | 600 |
| aatttctttt | tcaggtttct | atccattat | attattagca | cagtttga | | 648 |

<210> SEQ ID NO 66
<211> LENGTH: 449
<212> TYPE: RNA
<213> ORGANISM: Pediculus humanus

<400> SEQUENCE: 66

| aucgcaaaug aaggaauuuc gagaagcuuu ucgacuuuuu gacaaagaug gugaugguag | 60 |
| uauaacucaa gaagaacuug gaagaguuau gagaucuuua ggacaauuug ccagagaaga | 120 |
| agaacuacaa gaaaugcuua aggaaguuga uauagaugga gauggaaauu uuagcuuga | 180 |
| agaauuuguu gaaaucguau caaauauggg aggugcagca acugaaaaaa cagcugauga | 240 |
| agaagagaaa gaacuuagag augcuuuuag aguauuugau aaacauaauc gagguuuuau | 300 |
| aagugcuucu gaucuucgag cuguuuugca augucggu gaagaauuau cagaagaaga | 360 |
| aaaaaugaua agagaaguug augguggaugg agaugguaga auugauuuu ucgaauuugu | 420 |
| ucgagcuuug gguacacacu acaggcaaa | 449 |

<210> SEQ ID NO 67
<211> LENGTH: 648
<212> TYPE: DNA
<213> ORGANISM: Pediculus humanus

<400> SEQUENCE: 67

| atgatgaaaa acaaaactga cagcagtctc ggagctgagc attcagattt gaaacattcg | 60 |
| acgagtgaaa ccgaagaact ccaatcctcg gaactcgaag tgataaaaga tgaagagcct | 120 |
| caaatagatc tgagacagtt tctgacgaaa gaacaagtgc aagaattcaa agaattttc | 180 |
| caggcttacg atgtcaacaa cgaagataaa atcccggtca aagccatcgg aatcattttg | 240 |
| agaaacatgg gattgaatcc gtccaaggcg attctcaaga aatgacaaa ggaaatcgat | 300 |
| ccggataaaa acggttacgt ggatttcgaa atgttttac atcccatggc acgaatgata | 360 |
| cacgaagtcc cggaaaatca cgaggacata atcgcagcat tcaaagtttt cgacgaagac | 420 |
| gacgaaggtt tcgtatccgt taaagctttg accgaatacc tcacgaacct gggcgaagat | 480 |
| ttggaagatt tcgaaattga taatttgatt aaaatggcgg atcccaaagg cacgggccga | 540 |
| gtctactacg aaggattcgt cgagaaaatt ttcggaatcg taagaaacgg gaaaaaaaag | 600 |
| aaaaatctca agggaaaaa gggaaaaaaa cgaaaaaaaa atgaatga | 648 |

<210> SEQ ID NO 68
<211> LENGTH: 451
<212> TYPE: RNA
<213> ORGANISM: Pediculus humanus

<400> SEQUENCE: 68

| ucaaauagau cugagacagu ucugacgaaa gaacaagug caagaauuca aaagaauuuu | 60 |
| ccaggcuuac gaugucaaca acgaagauaa aaucccgguc aaagccaucg gaaucauuuu | 120 |
| gagaaacaug ggauugaauc cguccaaggc gauucucaag agaaugacaa aggaaaucga | 180 |
| uccggauaaa aacgguuacg uggauuucga augguuuua caucccaugg cacgaaugau | 240 |
| acacgaaguc ccggaaaauc acgaggacau aaucgcagca ucaaaguuu cgacgaaga | 300 |
| cgacgaaggu uucguauccg uuaaagcuuu gaccgaauac cucacgaacc ugggcgaaga | 360 |
| uuuggaagau uucgaaauug auaauuugau uaaaauggcg gaucccaaag gcacgggccg | 420 |
| agucuacuac gaaggauucg ucgagaaaau u | 451 |

<210> SEQ ID NO 69

```
<211> LENGTH: 1546
<212> TYPE: RNA
<213> ORGANISM: Varroa destructor

<400> SEQUENCE: 69
guuuagccca uuuucgcgcu gugucugucg gcgacugcgg aaguacugag cuagcugagu    60
cguggugcuu agaaggcagu ggcagugagu ggcaucagcg guaauaagug agggacaaca   120
gccggagagu cgucgguu gguaggucgg uucguugccg auuaaugccc cacaugugag    180
uuacgugcgg ugcuuguucc gcugugcauu ggacguuaca uacagagagu caggguguagu   240 uuauuuuaga cgaaaaacua ccagcacuac cugauacagc gacccaacgu agagagggaa   300
agagaaagag cuguuguuuc gcuagguuag uucugaacaa uuggauugau ucgcaaaugu   360
acgcuuguac ggcuaacggu ugaacggacu ugcaaacug cggauagugc gugaacuagc   420
agacaacaua uccaauaacu aacuacacgg uuauuauuga uacaaacacc uaguucagac   480
agacaauuuc gguugucuuu guggcacua uaaggaguaa gugauauugu uuuuguuua    540 ucagucggcc uaguauugc ggugcacuua cggauaacga gagaggcagu acaaaggcaa   600
cucgauucac uaucguucac gggcgcuaau acagcgaaau auuaauaggc aaagcaagca   660
agccagccgg ccaagcccaa accccgggcg aaacgcagau accaacagcg cugaagugcg   720
uggcaaacga caacgggaca guagggcaua agcuagacag cauauagcuu uucuaaccau   780
ggcugaucag cuaacugagg aacagaucgc cgaguucaaa gaggcguuua gccuguuuga   840
caaggacgga gauggcacga ucacgacaaa ggagcucggu acgguaaugc gaucucucgg   900
ccagaacccc acugaggcug aacugcagga caugaucaac gaggucgacg ccgacgcuc    960 cggaacgaua gauuucccug aguuccucac aaugauggca agaaagauga aggacaccga  1020
cucggaggag gagauccgag aggcguuccg cguauucgac aaggauggca acgguuucau  1080
uucggcggcc gagcucaggc acguuaugac caaccuuggc gagaagcuua cggacgagga  1140
gguagaugag augauucggg aggcagauau ugacggugau ggucagguca acuacgagga  1200
guucgucacc augaugacgu ccaaguaaau auaugauaau guuggcuguc ucguguaaug  1260
ucgugagaaa gaaagcgcgc gcgaaagaaa gagagaaagg aauagaaaac auauaaauagc  1320 uuguuguuaa agcaacgcaa caacaagcug uaagcaacaa acaauauuua cgaaguauac  1380
gauaaugaaa gucgacaggg aagcaagcac ggauauauau gaaaacuaag cgaaaugacg  1440
ucgucaucau caccagcagc agcagcagca gcagcagcag cagcagcagc accaccacca  1500
ccaccaucac gaccaccacc accaccacca ccaucgcgac caccac               1546

<210> SEQ ID NO 70
<211> LENGTH: 1136
<212> TYPE: RNA
<213> ORGANISM: Varroa destructor

<400> SEQUENCE: 70
guucggcucg gggacuagcu gaucggucgg uguguauugu uggcuauugg caaagaccgu    60
uguugagugg gcucgcugca cugagcguuu aaaucgggug aaaucguugg caauggcgga   120
ucagcugacc gaggagcaaa ucgccgaauu caaggaggcu uucagccugu ucgauaaaga   180
cggugauggc acaauuacga ccaaggaacu agggaccguc augcgguccc ucggccagaa   240
cccuacugag gcugagccuuc aagacaugau caacgaggu cgacgacgug uaacggcac    300 uauugacuuu ccagaguuuc ucacgaugau ggcgcguaaa augaaggaca ccgacuccga   360
ggaggagauc cggaagcuu uuagggguuu ugauaaagac ggaaauggcu ucauuucggc   420
```

-continued

```
ugcagagcug aggcacguaa ugaccaaccu uggcgaaaag cucacggacg aggaagugga    480
cgagaugauc cgcgaggcgg auaucgacgg cgacggacga gucaacuacg aggaguucgu    540
cacgaugaug acaucaaaau gaagggcuca cuauugcgcg ggaaaagcag cccaacaaag    600
aaaccuagag ugcgaaagcg agaacguuaa acacgaugau augcuaauga uaauacauac    660
gacuagagga cagaaagaca gacagacaga cugagcagac gaacgggcaa guugaagaaa    720
agccgaguug aacuggcuaa ccguuggggua ucauucaua uucgauaguu acagacaaca    780
acaugaaaaa cgacagcaac aauccgcaac aaacacacgg agauugcaca caaugagggu    840
aaacugaaca uggugcagcg gaaguuggau ggcagcggua cacagugcug cuacugcugc    900
ugcugcaaau gcuaacacuc aauaaugaua auaauaauua uaauuauaga aauaugauua    960
uguuguccaa aagagaaaca aacaacacaa acaaagcuau uaaaaaucug aauaaaagcu   1020
aagaagaaau caaguagcag ucgacauggg gaguggcaaa cgauaagagu ccacagaaaa   1080
cugaagcggc cgaaagaaaa cacgaggcaa aaggcaaugu auucauuaag acgagg       1136
```

<210> SEQ ID NO 71
<211> LENGTH: 150
<212> TYPE: RNA
<213> ORGANISM: Artificial Sequence
<220> FEATURE:
<223> OTHER INFORMATION: Synthetic Sequence

<400> SEQUENCE: 71

```
guuuagccca uuuucgcgcu gugucugucg gcgacugcgg aaguacugag cuagcugagu     60
cguggugcuu agaaggcagu ggcagugagu ggcaucagcg guaauaagug agggacaaca    120
gccggagagu cgugucgguu gguaggucgg                                     150
```

<210> SEQ ID NO 72
<211> LENGTH: 150
<212> TYPE: RNA
<213> ORGANISM: Artificial Sequence
<220> FEATURE:
<223> OTHER INFORMATION: Synthetic Sequence

<400> SEQUENCE: 72

```
uucguugccg auuaaugccc cacaugugag uuacgugcgg ugcuuguucc gcugugcauu     60
ggacguuaca uacagagagu cagguguagu uuauuuuaga cgaaaaacua ccagcacuac    120
cugauacagc gacccaacgu agagagggaa                                     150
```

<210> SEQ ID NO 73
<211> LENGTH: 150
<212> TYPE: RNA
<213> ORGANISM: Artificial Sequence
<220> FEATURE:
<223> OTHER INFORMATION: synthetic sequence

<400> SEQUENCE: 73

```
agagaaagag cuguuguuuc gcuagguuag uucugaacaa uuggauugau ucgcaaaugu     60
acgcuuguac ggcuaacggu ugaacggacu gugcaaacug cggauagugc gugaacuagc    120
agacaacaua uccaauaacu aacuacacgg                                     150
```

<210> SEQ ID NO 74
<211> LENGTH: 150
<212> TYPE: RNA
<213> ORGANISM: Artificial Sequence
<220> FEATURE:

<223> OTHER INFORMATION: synthetic sequence

<400> SEQUENCE: 74
uuauuauuga uacaaacacc uaguucagac agacaauuuc gguuugcuuu guuggcacua      60
uaaggaguaa gugauauugu uuuuuguuua ucagucggcc aguauuguc ggugcacuua      120 cggauaacag gagaggcagu acaaaggcaa                                      150

<210> SEQ ID NO 75
<211> LENGTH: 150
<212> TYPE: RNA
<213> ORGANISM: Artificial Sequence
<220> FEATURE:
<223> OTHER INFORMATION: synthetic sequence

<400> SEQUENCE: 75
cucgauucac uaucguucac gggcgcuaau acagcgaaau auuaauaggc aaagcaagca      60
agccagccgg ccaagcccaa acccgggcg aaacgcagau accaacagcg cugaagugcg       120
uggcaaacga caacgggaca guagggcaua                                      150

<210> SEQ ID NO 76
<211> LENGTH: 150
<212> TYPE: RNA
<213> ORGANISM: Artificial Sequence
<220> FEATURE:
<223> OTHER INFORMATION: synthetic sequence

<400> SEQUENCE: 76
agcuagacag cauauagcuu uucuaaccau ggcugaucag cuaacugagg aacagaucgc      60
cgaguucaaa gaggcguuua gccuguuuga caaggacgga gauggcacga ucacgacaaa      120
ggagcucggu acgguaaugc gaucucucgg                                      150

<210> SEQ ID NO 77
<211> LENGTH: 150
<212> TYPE: RNA
<213> ORGANISM: Artificial Sequence
<220> FEATURE:
<223> OTHER INFORMATION: synthetic sequence

<400> SEQUENCE: 77 ccagaaccc acugaggcug aacugcagga caugaucaac gaggucgacg ccgacggcuc       60
cggaacgaua gauuucccug aguccucac aaugauggca agaaagauga aggacaccga       120
cucggaggag gagauccgag aggcguuccg                                      150

<210> SEQ ID NO 78
<211> LENGTH: 150
<212> TYPE: RNA
<213> ORGANISM: Artificial Sequence
<220> FEATURE:
<223> OTHER INFORMATION: synthetic sequence

<400> SEQUENCE: 78
cguauucgac aaggauggca acgguuucau uucggcggcc gagcucaggc acguuaugac      60
caaccuuggc gagaagcuua cggacgagga gguagaugag augauucggg aggcagauau      120
ugacggugau ggucagguca acuacgagga                                      150

<210> SEQ ID NO 79
<211> LENGTH: 150
<212> TYPE: RNA
<213> ORGANISM: Artificial Sequence
<220> FEATURE:
<223> OTHER INFORMATION: synthetic sequence

<400> SEQUENCE: 79
guucgucacc augaugacgu ccaaguaaau auaugauaau guuggcuguc ucguguaaug    60
ucgugagaaa gaaagcgcgc gcgaaagaaa gagagaaagg aauagaaaac uauaaauagc   120
uuguuguuaa agcaacgcaa caacaagcug                                   150

<210> SEQ ID NO 80
<211> LENGTH: 150
<212> TYPE: RNA
<213> ORGANISM: Artificial Sequence
<220> FEATURE:
<223> OTHER INFORMATION: synthetic sequence

<400> SEQUENCE: 80
uaagcaacaa acaauauuua cgaaguauac gauaaugaaa gucgacaggg aagcaagcac    60
ggauauauau gaaaacuaag cgaaaugacg ucgucaucau caccagcagc agcagcagca   120
gcagcagcag cagcagcagc accaccacca                                   150

<210> SEQ ID NO 81
<211> LENGTH: 150
<212> TYPE: RNA
<213> ORGANISM: Artificial Sequence
<220> FEATURE:
<223> OTHER INFORMATION: synthetic sequence

<400> SEQUENCE: 81
guucggcucg gggacuagcu gaucggucgg uguguauugu uggcuauugg caaagaccgu    60
uguugagugg gcucgcugca cugagcguuu aaaucgguug aaaucguugg caauggcgga   120
ucagcugacc gaggagcaaa ucgccgaauu                                   150

<210> SEQ ID NO 82
<211> LENGTH: 150
<212> TYPE: RNA
<213> ORGANISM: Artificial Sequence
<220> FEATURE:
<223> OTHER INFORMATION: synthetic sequence

<400> SEQUENCE: 82
caaggaggcu uucagccugu ucgauaaaga cggugauggc acaauuacga ccaaggaacu    60
agggaccguc augcgguccc ucggccagaa cccuacugag gcugagcuuc aagacaugau   120
caacgagguc gacgcugacg guaacggcac                                   150

<210> SEQ ID NO 83
<211> LENGTH: 150
<212> TYPE: RNA
<213> ORGANISM: Artificial Sequence
<220> FEATURE:
<223> OTHER INFORMATION: synthetic sequence

<400> SEQUENCE: 83
uauugacuuu ccagaguuuc ucacgaugau ggcgcguaaa augaaggaca ccgacuccga    60
ggaggagauc cgggaagcuu uuagggu uuu ugauaaagac ggaauggcu ucauuucggc   120 ugcagagcug aggcacguaa ugaccaaccu                                   150

<210> SEQ ID NO 84
<211> LENGTH: 150
<212> TYPE: RNA

```
<213> ORGANISM: Artificial Sequence
<220> FEATURE:
<223> OTHER INFORMATION: synthetic sequence

<400> SEQUENCE: 84
uggcgaaaag cucacggacg aggaagugga cgagaugauc cgcgaggcgg auaucgacgg    60
cgacggacag gucaacuacg aggaguucgu cacgaugaug acaucaaaau gaagggcuca   120
cuauugcgcg ggaaaagcag cccaacaaag                                   150

<210> SEQ ID NO 85
<211> LENGTH: 150
<212> TYPE: RNA
<213> ORGANISM: Artificial Sequence
<220> FEATURE:
<223> OTHER INFORMATION: synthetic sequence

<400> SEQUENCE: 85
aaaccuagag ugcgaaagcg agaacguuaa acacgaugau augcuaauga uaauacauac    60
gacuagagga cagaaagaca gacagacaga cugagcagac gaacgggcaa guugaagaaa   120
agccgaguug aacuggcuaa ccguugggua                                   150

<210> SEQ ID NO 86
<211> LENGTH: 150
<212> TYPE: RNA
<213> ORGANISM: Artificial Sequence
<220> FEATURE:
<223> OTHER INFORMATION: synthetic sequence

<400> SEQUENCE: 86
cucauucaua uucgauaguu acagacaaca acaugaaaaa cgacagcaac aauccgcaac    60
aaacacacgg agauugcaca caaugagggu aaacugaaca uggugcagcg gaaguuggau   120
ggcagcggua cacagugcug cuacugcugc                                   150

<210> SEQ ID NO 87
<211> LENGTH: 150
<212> TYPE: RNA
<213> ORGANISM: Artificial Sequence
<220> FEATURE:
<223> OTHER INFORMATION: synthetic sequence

<400> SEQUENCE: 87
ugcugcaaau gcuaacacuc aauaaugaua auaauaauua uaauuauaga aauaugauua    60
uguuguccaa aagagaaaca aacaacacaa acaaagcuau uaaaaaucug aauaaaagcu   120
aagaagaaau caaguagcag ucgacauggg                                   150

<210> SEQ ID NO 88
<211> LENGTH: 156
<212> TYPE: RNA
<213> ORGANISM: Artificial Sequence
<220> FEATURE:
<223> OTHER INFORMATION: synthetic sequence

<400> SEQUENCE: 88
ggcaacgguu ucauuucggc ggccgagcuc aggcacguua ugaccaaccu uggcgagaag    60
cuuacggacg aggagguaga ugagaugauu cgggaggcag auauugacgg ugauggucag   120
gucaacuacg aggaguucgu caccaugaug acgucc                             156

<210> SEQ ID NO 89
<211> LENGTH: 257
```

```
<212> TYPE: RNA
<213> ORGANISM: Artificial Sequence
<220> FEATURE:
<223> OTHER INFORMATION: synthetic sequence

<400> SEQUENCE: 89
ggcggaucag cugaccgagg agcaaaucgc cgaauucaag gaggcuuuca gccuguucga      60
uaaagacggu gauggcacaa uuacgaccaa ggaacuaggg accgucaugc ggucccucgg     120
ccagaacccu acugaggcug agcuucaaga caugaucaac gaggucgacg cugacgguaa     180
cggcacuauu gacuuccag aguuucucac gaugauggcg cguaaaauga aggacaccga      240
cuccgaggag gagaucc                                                    257

<210> SEQ ID NO 90
<211> LENGTH: 420
<212> TYPE: RNA
<213> ORGANISM: Artificial Sequence
<220> FEATURE:
<223> OTHER INFORMATION: synthetic sequence

<400> SEQUENCE: 90
ggaacagauc gccgaguuca aagaggcguu uagccuguuu gacaaggacg gagauggcac      60
gaucacgaca aaggagcucg guacgguaau gcgaucucuc ggccagaacc cacugaggcu     120
gaacugcagg acaugaucaa cgaggucgac gccgacggcu ccggaacgau agauuucccu     180
gaguuccuca caaugaugca agaaagauga aggacaccga cucggaggag gagaucgaga     240
ggcguuccgc guauucgaca aggaugcaac gguuucauuu cggcggccga gcucaggcac     300
guuaugacca accuuggcga gaagcuuacg gacgaggagg uagaugagau gauucgggag     360
gcagauauug acggugaugg ucaggucaac uacgaggagu cgucaccau gaugacgucc      420

<210> SEQ ID NO 91
<211> LENGTH: 372
<212> TYPE: RNA
<213> ORGANISM: Artificial Sequence
<220> FEATURE:
<223> OTHER INFORMATION: synthetic sequence

<400> SEQUENCE: 91
ggaacagauc gccgaguuca aagaggcguu uagccuguuu gacaaggacg gagauggcac      60
gaucacgaca aaggagcucg guacgguaau gcgaucucuc ggccagaacc cacugaggcu     120
gaacugcagg acaugaucaa cgaggucgac gccgacggcu ccggaacgau agauuucccu     180
gaguuccuca caaugaugca agaaagauga aggacaccga cucggaggag gagaucgaga     240
ggcguuccgc guauucgaca aggaugcaac gguuucauuu cggcggccga gcucaggcac     300
guuaugacca accuuggcga gaagcuuacg gacgaggagg uagaugagau gauucgggag     360
gcagauauug ac                                                         372

<210> SEQ ID NO 92
<211> LENGTH: 477
<212> TYPE: RNA
<213> ORGANISM: Artificial Sequence
<220> FEATURE:
<223> OTHER INFORMATION: synthetic sequence

<400> SEQUENCE: 92
ggcggaucag cugaccgagg agcaaaucgc cgaauucaag gaggcuuuca gccuguucga      60
uaaagacggu gauggcacaa uuacgaccaa ggaacuaggg accgucaugc ggucccucgg     120
```

-continued

```
ccagaacccu acugaggcug agcuucaaga caugaucaac gaggucgacg cugacgguaa    180
cggcacuauu gacuuuccag aguuucucac gaugauggcg cguaaaauga aggacaccga    240
cuccgaggag ggauccggga agcuuuuagg guuuuugaua aagacggaaa uggcuucauu    300
ucggcugcag agcugaggca cguaaugacc aaccuuggcg aaaagcucac ggacgaggaa    360
guggacgaga ugauccgcga ggcggauauc gacggcgacg gacaggucaa cuacgaggag    420
uucgucacga ugaugacauc aaaaugaagg gcucacuauu gcgcgggaaa agcagcc      477
```

<210> SEQ ID NO 93
<211> LENGTH: 373
<212> TYPE: DNA
<213> ORGANISM: Artificial Sequence
<220> FEATURE:
<223> OTHER INFORMATION: synthetic sequence

<400> SEQUENCE: 93

```
ggagatcgcc gagttcaaag aggcgtttag cctgtttgac aaggacggag atggcacgat    60
cacgacaaag gagctcggta cggtaatgcg atctctcggc cagaacccca ctgaggctga   120
actgcaggac atgatcaacg aggtcgacgc cgacggctcc ggaacgatag atttccctga   180
gttcctcaca atgatggcaa gaaagatgaa ggacaccgac tcggaggagg agatccgaga   240
ggcgttccgc gtattcgaca aggatggcaa cggtttcatt tcggcggccg agctcaggca   300
cgttatgacc aaccttggcg agaagcttac ggacgaggag gtagatgaga tgattcggga   360
ggcagatatt gac                                                       373
```

<210> SEQ ID NO 94
<211> LENGTH: 376
<212> TYPE: RNA
<213> ORGANISM: Artificial sequence
<220> FEATURE:
<223> OTHER INFORMATION: synthetic sequence

<400> SEQUENCE: 94

```
ggaacagauc gccgaguuca aagaggcguu uagccuguuu gacaaggacg gagauggcac    60
gaucacgaca aaggagcucg guacgguaau gcgaucucuc ggccagaacc ccacugaggc   120
ugaacugcag gacaugauca acgaggucga cgccgacggc uccggaacga uagauuuccc   180
ugaguuccuc acaaugaugg caagaaaagau gaaggacacc gacucggagg aggagauccg   240
agaggcguuc cgcguauucg acaaggaugg caacgguuuc auuucggcgg ccgagcucag   300
gcacguuaug accaaccuug gcgagaagcu uacggacgag gagguagaug augauucg     360 ggaggcagau auugac                                                    376
```